(12) United States Patent
Stemmer et al.

(10) Patent No.: US 6,500,617 B1
(45) Date of Patent: Dec. 31, 2002

(54) OPTIMIZATION OF PEST RESISTANCE GENES USING DNA SHUFFLING

(75) Inventors: Willem P. C. Stemmer, Los Gatos; Linda A. Castle, Mountain View; Takashi Yamamoto, Fremont, all of CA (US)

(73) Assignee: Maxygen, Inc., Redwood City, CA (US)

( * ) Notice: Subject to any disclaimer, the term of this patent is extended or adjusted under 35 U.S.C. 154(b) by 0 days.

(21) Appl. No.: 09/296,886

(22) Filed: Apr. 22, 1999

Related U.S. Application Data

(60) Provisional application No. 60/094,462, filed on Jul. 28, 1998, and provisional application No. 60/122,054, filed on May 1, 1998.

(51) Int. Cl.[7] .......................... C12Q 1/68; C12P 21/06; C07H 21/02
(52) U.S. Cl. ...................... 435/6; 435/69.1; 435/320.1; 435/410; 435/418; 435/DIG. 1; 435/DIG. 2; 435/DIG. 3; 435/DIG. 4; 435/DIG. 5; 435/DIG. 14; 435/DIG. 15; 435/DIG. 17; 536/23.1; 536/23.7
(58) Field of Search .......................... 435/6, 69.1, 410, 435/418, 320.1, DIG. 1, DIG. 2, DIG. 5, DIG. 14, DIG. 15, DIG. 17; 536/23.1, 23.7, 23.71

(56) References Cited

U.S. PATENT DOCUMENTS

| | | | |
|---|---|---|---|
| 4,448,885 A | 5/1984 | Schnepf et al. | |
| 4,467,036 A | 8/1984 | Schnepf et al. | |
| 4,766,203 A | 8/1988 | Krieg | |
| 4,771,131 A | 9/1988 | Herrnstadt et al. | |
| 4,797,276 A | 1/1989 | Herrnstadt et al. | |
| 4,849,217 A | 7/1989 | Soares et al. | |
| 4,853,331 A | 8/1989 | Herrnstadt et al. | |
| 4,918,006 A | 4/1990 | Ellar et al. | |
| 4,948,734 A | 8/1990 | Edwards et al. | |
| 5,151,363 A | 9/1992 | Payne | |
| 5,218,104 A | 6/1993 | Hilder et al. | |
| 5,306,863 A | 4/1994 | Hilder et al. | |
| 5,512,463 A | 4/1996 | Stemmer | |
| 5,514,588 A | 5/1996 | Varadaraj | |
| 5,605,793 A | 2/1997 | Stemmer | |
| 5,629,469 A | 5/1997 | Deluca-Flaherty et al. | |
| 5,633,446 A | 5/1997 | Cornclissen et al. | |
| 5,635,480 A | 6/1997 | Payne et al. | |
| 5,640,804 A | 6/1997 | Driver et al. | |
| 5,651,965 A | 7/1997 | Payne | |
| 5,659,123 A | 8/1997 | Van Rie et al. | |
| 5,662,897 A | 9/1997 | Miller et al. | |
| 5,683,691 A | 11/1997 | Peferoen et al. | |
| 5,743,477 A | 4/1998 | Walsh et al. | |
| 5,763,239 A | 6/1998 | Short et al. | |
| 5,789,228 A | 8/1998 | Lam et al. | |
| 5,811,238 A | 9/1998 | Stemmer et al. | |
| 5,814,473 A | 9/1998 | Warren et al. | |
| 5,824,469 A | 10/1998 | Horwitz et al. | |
| 5,824,864 A | 10/1998 | Fox et al. | |
| 5,830,696 A | 11/1998 | Short | |
| 5,830,721 A | 11/1998 | Stemmer et al. | |
| 5,834,252 A | 11/1998 | Stemmer et al. | |
| 5,837,458 A | 11/1998 | Minshull | |
| 5,866,363 A | 2/1999 | Pieczenik | |
| 5,874,288 A | 2/1999 | Thompson et al. | |
| 5,876,997 A | 3/1999 | Kretz | |
| 5,882,668 A | 3/1999 | Garnaat et al. | |
| 5,882,851 A | 3/1999 | Koch et al. | |
| 5,919,658 A | 7/1999 | Ni et al. | |
| 5,925,749 A | 7/1999 | Mathur et al. | |
| 5,928,905 A | 7/1999 | Stemmer et al. | |
| 5,939,250 A | 8/1999 | Short | |
| 5,939,300 A | 8/1999 | Robertson et al. | |
| 5,942,430 A | 8/1999 | Robertson et al. | |
| 5,948,666 A | 9/1999 | Callen et al. | |
| 5,958,672 A | 9/1999 | Short | |
| 5,958,751 A | 9/1999 | Murphy et al. | |
| 5,962,258 A | 10/1999 | Mathur et al. | |
| 5,962,283 A | 10/1999 | Warren et al. | |
| 5,965,408 A | 10/1999 | Short | |
| 5,976,862 A | 11/1999 | Kauffman et al. | |
| 5,985,646 A | 11/1999 | Murphy et al. | |
| 6,001,574 A | 12/1999 | Short et al. | |
| 6,004,788 A | 12/1999 | Short | |
| 6,030,779 A | 2/2000 | Short | |
| 6,054,267 A | 4/2000 | Short | |
| 6,057,103 A | 5/2000 | Short | |
| 6,057,491 A | 5/2000 | Cigan et al. | |
| 6,060,594 A | * 5/2000 | English et al. | ........... 536/23.71 |
| 6,077,824 A | * 6/2000 | English et al. | ................ 514/12 |
| 6,090,931 A | 7/2000 | Edwards et al. | |
| 6,096,548 A | 8/2000 | Stemmer | |
| 6,117,679 A | 9/2000 | Stemmer | |
| 6,132,970 A | 10/2000 | Stemmer | |
| 6,165,793 A | 12/2000 | Stemmer | |
| 6,168,919 B1 | 1/2001 | Short | |
| 6,171,820 B1 | 1/2001 | Short | |
| 6,174,673 B1 | 1/2001 | Short et al. | |
| 6,180,406 B1 | 1/2001 | Stemmer | |

FOREIGN PATENT DOCUMENTS

| | | |
|---|---|---|
| AU | 36568/89 A | 6/1989 |
| EP | 0149165 | 3/1990 |
| EP | 0213818 | 2/1991 |

(List continued on next page.)

OTHER PUBLICATIONS

Barcelo and Lazzari, (1995) Methods Mol. Biol. 49:113–123.

(List continued on next page.)

Primary Examiner—Padmashri Ponnaluri
(74) Attorney, Agent, or Firm—Norman J. Kruse; Christopher M. Holman

(57) ABSTRACT

This invention provides methods of obtaining pest resistance genes that are improved over naturally occurring genes for use in conferring upon plants resistance to pests. The methods involve the use of DNA shuffling of pest resistance genes to produce libraries of recombinant pest resistance genes, which are then screened to identify those that exhibit the improved property or properties of interest.

26 Claims, 5 Drawing Sheets

FOREIGN PATENT DOCUMENTS

| | | |
|---|---|---|
| EP | 0193259 | 12/1991 |
| EP | 0911396 A2 | 4/1999 |
| EP | 0911396 A3 | 5/1999 |
| EP | 0934999 A1 | 8/1999 |
| WO | 94/25579 | 11/1994 |
| WO | 95/22625 | 8/1995 |
| WO | 97/07205 | 2/1997 |
| WO | 97/20078 | 6/1997 |
| WO | 97/21806 | 6/1997 |
| WO | 97/25410 | 7/1997 |
| WO | 97/35957 | 10/1997 |
| WO | 97/35966 | 10/1997 |
| WO | 97/44361 | 11/1997 |
| WO | 97/48416 | 12/1997 |
| WO | 97/48717 | 12/1997 |
| WO | 97/48794 | 12/1997 |
| WO | 98/00526 | 1/1998 |
| WO | 98/01581 | 1/1998 |
| WO | 98/13485 | 4/1998 |
| WO | 98/13487 | 4/1998 |
| WO | 98/24799 | 6/1998 |
| WO | 98/27230 | 6/1998 |
| WO | 98/28416 | 7/1998 |
| WO | 98/31837 | 7/1998 |
| WO | 98/36080 | 8/1998 |
| WO | 98/39471 | 9/1998 |
| WO | 98/41622 | 9/1998 |
| WO | 98/41623 | 9/1998 |
| WO | 98/41653 | 9/1998 |
| WO | 98/42832 | 10/1998 |
| WO | 98/48034 | 10/1998 |
| WO | 98/54327 | 12/1998 |
| WO | 98/58085 | 12/1998 |
| WO | 99/07837 | 2/1999 |
| WO | 99/08539 | 2/1999 |
| WO | 99/10472 | 3/1999 |
| WO | 99/10539 | 3/1999 |
| WO | 99/19518 | 4/1999 |
| WO | 99/23107 | 5/1999 |
| WO | 99/23236 | 5/1999 |
| WO | 99/21979 | 6/1999 |
| WO | 99/31248 | 6/1999 |
| WO | 99/41368 | 8/1999 |
| WO | 99/41369 | 8/1999 |
| WO | 99/41383 | 8/1999 |
| WO | 99/41402 | 8/1999 |
| WO | 99/45154 | 9/1999 |
| WO | 99/57128 | 11/1999 |
| WO | 99/65927 | 12/1999 |
| WO | 00/08159 | 2/2000 |
| WO | 00/42560 | 7/2000 |
| WO | 00/42561 | 7/2000 |
| WO | 00/53744 | 9/2000 |
| WO | 00/58517 | 10/2000 |

OTHER PUBLICATIONS

Peferoen, (1997) *Advances in Insect Control*, Chapter 2, pp. 21–48.

Purcell, (1997) *Advances in Insect Control*, Chapter 6, pp. 95–108.

Reeck et al. (1997) *Advances in Pest Control*, Ch. 10, pp. 157–183.

Abe, K., et al., "Molecular Cloning of a Cysteine Proteinase Inhibitor of Rice (Oryzacystatin)" *J. of Biological Chem.*, (1987) 262:167–16797.

Chen, M.S., et al., "Rice Cystatin: Bacterial Expression, Purification, Cysteine Proteinase Inhibitory Activity, and Insect Growth Suppressing Activity of a Truncated Form of the Protein" *Protein Expression and Purification*, (1992) 3:41–49.

Kondo, H., et al., "Gene Organization of Oryzacystatin–II, a New Cystatin Superfamily Member of Plant Origin, is Closely Related to that of Oryzacystatin–I but Different from Those of Animal Cystatins" (1991) *FEBS*, 278(1):87–90.

PCT International Preliminary Examination Report (PCT Article 36 and Rule 70, Form PCT/IPEA/409) for International application PCT/US99/08473 filed Apr. 22, 1999, dated Feb. 7, 2000.

Chang, C., et al. (1999) "Evolution of a cytokine using DNA family shuffling." *Nature Biotechnology* 17:793–797.

Christians, F.C. et al., (1999) "Directed evolution of thymidine kinase for AZT phosphorylation using DNA family shuffling." *Nature Biotechnology* 17:259–264.

Crameri et al., (1993) "10(20)–Fold aptamer library amplification without gel purification," *Nuc. Acids Res.* 21(18):4410.

Crameri, A. & Stemmer W.P.C. (1995) "Combinatorial multiple cassette mutagenesis creates all the permutations of mutant and wildtype cassettes." *Biotechniques* 18:194–195.

Crameri, A. et al., (1997) "Molecular evolution of an arsenate detoxification pathway by DNA shuffling." *Nature Biotechnology* 15:436–438.

Crameri, A. et al. (1998) "DNA shuffling of a family of genes from diverse species accelerates directed evolution." *Nature* 391:288–291.

Gates, C.M. et al., (1996) "Affinity selective isolation of ligands from peptide libraries through display on a lac repressor headpiece dimer" *Journal of Molecular Biology* 255:373–386.

Minshull, J., Stemmer, W.P.C. (1999) "Protein evolution by molecular breeding." *Current Opinion in Chemical Biology* 3:284–290.

Ness, J. et al., (1999) "DNA shuffling of subgenominc sequences of subtilisin." *Nature Biotechnology* 17:893–896.

Patten, P.A. et al., (1997) "Application of DNA Shuffling to Pharmaceuticals and Vaccines." *Current Opinion in Biotechnology* 8:724–733.

Stemmer, W.P.C. (1996) "Sexual PCR and Assembly PCR." In: *The Encyclopedia of Molecular Biology*. VCH Publishers, New York. pp. 447–457.

Stemmer, W.P.C. & Soong, N.W. (1999) "Molecular breeding of viruses for targeting and other clinical properties." *Tumor Targeting* 4:59–62.

Zhang, J. et al., (1997) "Directed evolution of an effective fucosidase from a galactosidase by DNA shuffling and screening." *Proceedings of the National Academy of Sciences, USA* 94:4504–4509.

Assano, et al., "Cloning of Novel Enterontoxin Genes from *Bacillus cereus* and *Bacillus thuringiensis*" *Appl. and Envi. Micor.* (1997) 1054–1057.

Beegle, C., Invitation paper (C.P. Alexander Fund): History of *Bacillus theringiensis* Berliner Research and Development. *Can. Ent.* 124:587–616.

Bosch et al., "Recombinant *Bacillus thuringiensis* Crystal Proteins with New Properties: Possibilities for Resistance Management" *Bio/Technology* vol. 12 (1994) p. 915–918.

Chak, et al., "Expression of the Crystal Protein Gene under the Control of the a–Amylase Promoter in *Bacillus thuringiensis* Strains" *Applied & Envir. Micob.* (1194) p. 2304–2310.

Davidson and Yamamoto, Isolation and Assay of the Toxic Component from the Crystals of *Bacillus thuringiensis* var. *israelensis Current Microbiology* vol. 11 (1984) pp. 171–174.

DeMaagd, et al. "Domain III Substitution in *Bacillus thuringiensis* Delta–Endotoxin CrylA(b) Results in Superior Toxicity . . . " *Applied & Enviro. Micorb.* (1996) p. 1537–1543.

DeMaagd, et al. "Identification of *Bacillus thuringiensis* Delta–Endotoxin CrylC Domain III Amino Acid . . . " *Applied & Enviro. Micorb.* (1999) p. 4369–4374.

Estruch et al., "Transgenic plants: An emerging approach to pest control" *Nature Biology* vol. 15, (1997) p. 137–141.

Hussain, Syed–Rehan, et al. (1996) "Substitution of Residues on the Proximal Side Cry1A *Bacillus thuringiensis* δ–Endotoxins Affects Irreversible Binding to *Manduca sexta* Midgut Membrane." *Biochemical and Biophysical Research Communications* 223:8–14.

Iizuk and Yamamoto, "Serological Properties of the Mosquitocidal Protein of *Bacillus thuringiensis* and the morphology of its parasporal crystal" *J. Fac. Agr. Hokkaido Univ.* vol. 62 pt. 1, 1984.

Iizuk and Yamamoto "Possible location of the mosquitocidal *Bacillus thuringiensis* subsp. kurstaki" *FEMS Micorb. Letters* 19 (1983) 187–192.

Ignacimuthu, 1996. Biotechnological Perspectives in Chemical Ecology of Insects—pp. 276–283, "Transgenics and Insect Resistance: Role of Protease Inhibitors".

Jellis, C. et al. (1989) "Molecular Biology of *Bacillus thurigenisis* and Potential Benefits to Agriculture." *Israel Journal of Entomology* 23:189–199.

Jongsma, et al., "Phage display of a double–headed proteinase inhibitor: analysis of the binding domains of potato proteinase inhibitor II" *Mol. Bredding* 1:181–191 (1995).

Jongsma et al., "Characterization and Partial Purification of Gut Proteinases of *Spodoptera exigua* Hunmer" *Insect Biochem. Molc. Biol.* vol. 26, No. 2 p. 185–196 (1996).

Jongsma et al., "Adaptation of *Spodoptera exigua* larvae to plant proteinase inhibitors by induction of gut proteinase activity insensitive to inhibition" *Proc. Natl Acd. Sci.* v. 92, 8041–45.

Jongsma, et al., "Combatting inhibitor–insensitive proteases of insect pests" *Tibtech* (1996) vol. 14.

Kalman, et al., "Field Trials of Genetically Engineered *Bacillus thurnigenisis*" *Bacillus thurnigenisis Biotechnology and Environmental Benefits* vol. 1 297–311 (1995).

Kalman et al., "Enhancing production of insecticidal proteins in *Bacillus thurnigenisis* strains carrying . . . " *Applied and Enviro. Micob.* (1995) p. 3063–3068.

Kalman et al., "Cloning of a Novel crylC–Type gene from a strain of *Bacillus thurnigenisis* subsp. *galleriae*" *Applied and Eniro. Micro.* (1993) p. 1131–1137.

Keeton et al., "Ligand specificity and affinity of BT–R1, the *Bacillus thurigenisis* Cry1A Toxin receptor . . . " *Applied and Enviro. Mico.* (1997) p. 3419–3425.

Kwa, et al., "Toxicity and Binding Properties of the *Bacillus thurnigenisis* Delta–Endotoxin Cry1C to Cultured Insect Cells" *J. of Invertebrate Pathology* 71, 121–137 (1998).

Kwak, In–Seok et al. (1995) "Exploration of Receptor Binding of *Bacillus thuringiensis* Toxins" *Mem Inst Oswaldo, Rio de Janeiro* 90(1):75–79.

Lee, Mi Kyong (1996) Involvement of Two Amino Acid Residues in the Loop Region of *Bacillus thuringiensis* Cry1Ab Toxin in Toxicity and Binding to *Lymantria dispar. Biochemical and Biophysical Research Communications* 229:139–146.

Lee, Mi Kyong et al., (1995) Domain III Exchanges of *Bacillus thurngiensis* Cryia Toxins Affect Binding to Different Gypsy Moth Midgut Receptors. *Biochemical and Biophysical Research Communications* 216:306–312.

Lu, Hong, et al., (1994) Identification of Amino Acid Residues of *Bacillus thuringiensis* δ–Endotoxin CrylAa Associated with Membrane Binding and Toxicity to *Bombyx mori*. *Journal of Bacteriology* 176(17):5554–5559.

Okunuki, et al., "Structural changes of cytochrome oxidase dependent on its redox state" Dept. of Bol., Faculty of Science, Univ. of Osaka, Japan pp. 171–177, 1972.

Powell et al., "Recent advances in Structure and function research on *Bacillus thurnigenisis* crystal proteins" *Bacillus thurnigenisis Biotechnology and Environmental Benefits* vol. 1 1–20.

Rajamohan, Francis, et al. (1995) "Single Amino Acid Changes in Domain II of *Bacillus thurigiensis* CrylAb δ–Endotoxin Affect Irreversible Binding to *Manduca sexta* Midgut Membrane Vesicles." *Journal of Bacteriology* 177(9):2276–2282.

Rajamohan, Francis, et al. (1996) "Mutations of Domain II, Loop 3, of *Bacillus thurigiensis* CrylAa and CrylAb δ–Endotoxins Suggest Loop 3 is Involved in Initial Binding to Lepidopteran Midguts" *Journal of Biological Chemistry* 271(41): 25220–25226.

Rajamohan, Francis, et al. (1996) "Protein engineering of *Bacillus thurigiensis* δ–endotoxins: Mutations at domain II of CrylAb enhance receptor affinity and toxicity toward gypsy moth larvae." *Proc. Natl. Acad. Sci. USA* 93:14338–14343.

Rajamohan, Francis, et al. (1996) "Role of Domain II, Loop 2 Residues of *Bacillus thuringigiensis* CrylAb δ–Endotoxin in Reversible and Irreversible Binding to *Manduca sexta* and *Heliothis viroscens*." *Journal of Biological Chemistry* 271(5):2390–2396.

Sasaki, et al., "Insecticidal activity of the protein encoded by the cryV gene of *Bacillus thurnigenisis kurstaki* INA–02" *Current Microbiology* vol. 32, (1996) p. 195–200.

Soderlund, "Molecular mechanisims of resistance to agrochemicals" *13 Chemistry of Plant Protection* (1997) 21–56.

Tanada, et al., "Liocalization of a synergistic factor of a granulosis virus by its esterase activity in the larval midgut of the armyworm, *Pseudaletia unipuncta*"*Micobios* 37 87–93 (1983).

Tabashenik "Seeking the root of insect resistance to transgenic plants" *Proc. Natl. Acad. Sci. USA* 94 (1997) 3488–3490.

Wolfersberger, M.G., et al. (1996) "Site–Directed Mutations in the Third Domain of *Bacillus thuringiensis* δ–Endotoxin CrylAa Affect Its Ability To Increase the Permeability of *Bombyx mori* Midgut Brush Border Membrane Vesicles." *Applied and Environmental Microbiology* 62(1):279–282.

Wu, Sheng–Jiun and Dean, Donald H. (1996) "Functional Significance of Loops in the Receptor Binding Domain of *Bacillus thuringiensis* CrtIIIA δ–Endotoxin." *J. Mol. Biol.* 255:628–640.

Wu, Sheng–Jiun, et al. (1995) "Exploration of the Mode of Action *Bacillus thuringienesis* Toxin by Site–directed Mutagensis." T–Y Feng et al. (eds.), *Bacillus thuringiensis Biotechnology and Environmental Benefits*, vol. 1, 51–67, Hua Shiang Yuan Publishing Co., Taipei, Taiwan.

Yamamoto, T. and Dean, D.H. (2000) "Insecticidal proteins produces by bacteria pathogenic to agricultural pests." J.F. Charles et al (eds.) *Entomopathogenic Bacteria: From Laboratory to Field Applications*, 81–100, Kluwer Academic Publishers, Netherlands.

Yamamoto, et al., "Acylamines Enhance the infection of a Baculovirus of the Armyworm, *Pseudaletia unipuncta* (Noctuide, Leidoptera)" *J. of Invertebrate Pathology* 35, 265–268, 1980.

Yamamoto, et al., "Assembly of Occlusion–Body proteins around the enveloped virion of an inscet baculovirus" *J. of Ultrastructure Research* 75, 127–130 (1981).

Yamamoto, et al., "*Bacillus thuringigiensis* crystal proteins: recent advances in understanding its insecticidal activity" *Advanced Engineered Pesticides* 1993.

Yamamoto, et al., "Biochemical properties of viral envelopes of insect baculoviruses and their role in infectivity" *J. of Invertebrate Pathology* 32, 202–211 (1978).

Yamamoto, et al., "Capsule componenets of two strains of a granulosis virus of the armyworm (*Pseudaletia unipuncta*): Purification . . . " *J. Gen. Virol.* (1979) 45, 371–381.

Yamamoto, et al., "Comparative analysis of the enveloped virions of two granulosis viruses of the armyworm, *Pseudaletia unipuncta*" *Virology* 94, 71–81 (1979).

Yamamoto, et al., "Environmental release of genetically engineered *Bacillus thuringiensis*" *Reviews in Toxicology* 2 (1998) 157–166.

Yamamoto, et al., "Expression of three genes coding for 135–kilodalton entomocidal proteins in *Bacillus thuringiensis kurstaki*" *Current Microbiology* vol. 17, (1988) 5–12.

Yamamoto, "Identification of entomocidal toxins of *Bacillus thuringiensis* by high–performance liquid chromatography" *Analytical Chemistry of Bacillus thuringiensis* 46–60.

Yamamoto, "Identification of entomocidal toxins of *Bacillus thuringiensis* by high–performance liquid chromatography" *J. of General Microbiology* (1983) 129, 2595–2603.

Yamamoto, et al., "Immunological properties of entomocidal protein of *Bacillus thuringiensis* and its insecticidal activity" *J. of Invertebrate Pathology* 41, 122–130 (1983).

Yamamoto, et al., "Insecticidal proteins produced by bacteria pathogenic to agricultural pests" *Entomophathogenic Bacteria: From Lab. to Field Application*, 81–100 Chapter 2.2.

Yamamoto, et al., "Isolation of a protein from the parasporal crystal of *Bacillus thuringiensis* var. kurstaki toxic . . . " *Biochm. & Bioph. Research Comm.* v. 103, No. 2, 1981, p. 414–421.

Yamamoto, et al., "Location of Heme a in Cytochrome a*" *J. Biochem.* 73, 1049–1059 (1973).

Yamamoto, et al., "Location of Heme a in Cytochrome a*" *J. Biochem.* 74, 473–479 (1973).

Yamamoto, et al., "Mosquitocidal protein of *Bacillus thuringiensis* subsp. *israelensis*: Identification and partial isolation of the protein" *Current Micobiology* v. 9, (1983) 279–284.

Yamamoto, et al., "Nucleotide sequence of the gene coding for a 1300kDa Mosquitocidal protein of *Bacillus thuringiensis israelensis*"*Gene* 66, 107–120.

Yamamoto, et al., "Phospholipid, an enhancing component in the synergistic factor of a granulosis virus of the armyworm, *Pseudaletia unipuncta*" *J. of Invertebrate Pathology* 31, (1978), 48–56.

Yamamoto, et al., "Physicochemical properties and location of capsule components, on particular the synergistic factor . . . " *Virology* 107, 434–440 (1980).

Yamamoto, et al., Protein components of two strains of granulosis virus of the armyworm, *Pseudaletia unipuncta* (Lepidoptera, Noctuidae) *J. of Invertebrate Pathology* 32, 158–170 (1978).

Yamamoto, et al., "The polypeptide composition of bovine cytochrome oxidase and its "Proteinase–treated" derivative" *J. Biochem.* 75, 1081–1089 (1974).

Yamamoto, et al., "Possible Involvement of Phospholipids in the Infectivity of Baculoviruses" *J. of Invertebrate Pathology* 30, 279–281 (1977).

Yamamoto, et al., "Redox State of Cytochrome a and Its Sensitivity to Proteinases" *J. of Biochemistry* v. 67, No. 3, 1970, p. 505–506.

Yamamoto, et al., "Structural damages to the granulosis virus of the armyworm, *Pseudaletia unipuncta*, caused by sucrose density gradient centrifugation" *J. of Invertebrate Pathology* 34, 312–314, (1979).

Yamamoto, et al., "Structure and function of the insecticidal protein produced by *Bacillus thuringiensis*" 137–144.

Yamamoto, et al., Studies on Cytochrome a, "Preparation and some properties of proteinase–treated cytochrome a*" *J. Biochem.* 435–445 (1972).

Yamamoto, et al., "Two 2–dimensional electrophoreses: A combination of crossed immunoelectrophoresis and dodecyl . . . " *Experientia* 36 (1980) 816–817.

Yamamoto, et al."Two types of entomocidal toxins in the parasporal crystals of *thuringiensis israelensis kurstaki*" *Archives of Biochemistry and Biophysics* v. 227, No. 1, p. 233–241 (1983).

Abe et al., (1987) Molecular Cloning of Cysteine Proteinase Inhibitor of Rice (Oryzacystatin) *J. Biol. Chem* 262:16793–16797.

Carter et al., (1985) "Improved oligonucleotide site–directed mutagenesis using M13 vectors" *Nucl. Acids Res.* 13:4431–4443.

Carter, (1987) "Improved Oligonucleotide–Directed Mutagensis using M13 Vectors" *Methods in Enzymol.* 154: 382–403.

Crameri et al., "Improved Green Fluorescent Protein by Molecular Evolution Using DNA Shuffling" *Nature Biotechnology* 14: 315–319.

Crameri et al. (1996) "Construction And Evolution Of Antibody–Phage Libraries By DNA Shuffling" *Nature Medicine* 2(1):100–103.

Crickmore et al., (1996) Genes Microbiol. Res.

Cwirla et al., (1990) "Peptides on phage: A vast library of peptides for identifying ligands" *Proc. Nat'l Acad. Sci. USA* 87: 6378–6382.

De Cleene and DeLey, (1981) "The Host Range of Infectious Hairy–Root" *Bot. Rev.* 47: 147–94.

Devlin et al., (1990) "Random Peptide Libraries: A Source of Specific Protein Binding Molecules" *Science* 249:404–406.

De Maagd et al., (1996) "Different Domains of *Bacillus thuringiensis* Endotoxins Can bind to Insect Midgut Proteins on Ligand Blots" *Appl. Environ. Microbiol.* 62: 2753–7.

Eghtedarzadeh and Henikoff, (1986) "Use of oligonucleotides to generate large deletions" *Nucl. Acid Res.* 14:5115.

Estruch et al. (1997) "Vip3A, a novel *Bacillus thuringiensis* vegetative insecticidal protein with a wide spectrum of activities against lepidopteran insects" *Proc. Nat'l. Acad. Sci. USA* 93:5389–5394.

Fraley et al., (1983) "Expression of bacterial genes in plant cells" *Proc. Nat'l Acad. Sci. USA* 80:4803.

Gatehouse et al. (1998) "Identifying Proteins with Insecticidal Activity: Use of Encoding genes to Produce Insect–Resistant Transgenic Crops" *Pest. Sci.* (1998) 52:165–175.

Grundstrom et al., (1985) "Oligonucleotide–directed mutagenesis by microschale 'shot-gun' gene synthesis" *Nucl. Acids Res.* 13: 3305–3316.

Hilder et al., (1993) "Transgenic Plants Conferring Insect Tolerance:Protease Inhibitor Approach" *Transgenic Plants*, vol. 1, Kung and Wu Eds., Academic Press, pp. 317–338.

Hofte and Whiteley, (1989) "Insecticidal Crystal Proteins of *Bacillus thurgiensis*" *Microbiol. Rev.* 53:242–255.

Horsch et al., (1984) "Inheritance of Functional Foreign Genes in Plants" *Science* 223: 496–498.

Jongsma, (1997) "The Adaption of Insects to Plant Protease Inhibitors" *J. Insect Physiol.* 43:885–895.

Kholsa et al., "Generation of polyketide libraries via combinatorial biosynthesis" *TIBTECH* 14, Sep. 1996.

Kramer et al., (1984) "Different Base/Base Mismatches Are Corrected with Different Efficiencies by the Methyl––Directed DNA Mismatch–Repair System of *E. coli*" *Cell* 38: 879–887.

Kumar et al., (1996) "The insecticidal proteins of *Bacillus thuringiensis*" *Adv. Appl. Microbiol.* 42:1–43.

Laskowski et al., (1980) "Protein Inhibitors of Proteinases" *Annu. Rev. Biochem.* 49: 593–626.

Main et al., (1995) "Electroporation Protocols for Agrobacterium" *Methods Mol. Biol.* 44:405–412).

Martens et al., (1990) "Insecticidal Activity of Bacterial Crystal Protein Expressed by a Recombinant Baculovirus in Insect Cells" *Appl. Environmental Microbiol.* 56:2764–2770.

Merryweather et al., (1990) "Construction of genetically engineered baculovirus insecticides containing the *Bacillus thuringiensis* subsp. *kurstaki* HD–73 delta endotixin"*J. Gen. Virol.* 71:1535–1544.

Nambiar et al., (1984) "Total Sythesis and Cloning of a Gene Coding for the Ribonuclease S. Protein" *Science* 223:1299–1301.

Ogiwara et al., (1995) "Nucleotide Sequence of the Gene Encoding Novel Delta–Endotoxin from *Bacillus thuringiensis* Serovar *japonensis* Strain Buidui Specfic to Scarabaeid Beetles" *Curr. Microbiol.* 30: 227–235.

Reddy et al., (1975) "Primary Structural analysis of Sulfhydryl Protease Inhibitors" *J. Biol. Chem* 250:1741–1750.

Ryan, (1990) "Protease Inhibitor in Plants: Genes for Improving Defenses Against Insects and Pathogens" *Annu. Rev. Phytopathol.* 28: 425–449.

Saito et al., (1992) "Transgenoc Medicinal Plants: Agrobacterium–Mediated Foreign Gene Transfer and Production of Secondary Metabolites" *J. Nat. Prod.* 55: 149–162.

Sakamar and Khorana, "Total synthesis and expression of a gene for the α–subunit of bovine rod outer segment guanine nucleotide–binding protein" (1985) *Nucl. Acids Res.* 14:6361–6372.

Sasaki et al., (1996) "Insecticidal Activity of the Protein Encoded by the cryV Gene of *Bacillus thurnigiensis kurstaki* INA–02" *Curr. Microbiol.* 31:195–200.

Schuler et al., (1998) "Insect–resistant transgenic plants" *Tibtech* 16: 168–175.

Scott & Smith, (1990) "Searching for Peptide Ligands with a Epitope Library" *Science* 249: 386–388.

Shen et al., (1997) "Studies on the Mode of Action of Cholesterol Oxidase on the Insect Midgut Membranes" *Arch. Insect Biochem. Physiol.* 34:429–442.

Shivaraj et al., (1981) "Natural plant enzyme inhibitors" *Biochem J.* 193:29–36.

Stahly et al., (1978) "Possible Origin and Funcion of the Parasporal Crystals in *Bacillus thuringiensis*" *Biochem. Biophys. Commun.* 84: 581–588.

Stemmer (1995) "Searching Sequence Space" *Bio/Technology* 13:549–553.

Stemmer, (1995) "The Evolution of Molecular Computation" *Science* 270:151.

Stemmer et al., (1995) "Single–step assembly of a gene and entire plasmid from large numbers of oligodeoxyribonucleotides" *Gene* 164: 49–53.

Stemmer et al. (1994) "Rapid Evolution of a Protein in vitro by DNA shuffling" *Nature* 370:389–391.

Stemmer et al., (1994) "DNA Shuffling by Random Fragmentation and Reassembly: in vitro Recombination for Molecular Evolution," *Proc. Natl. Acad. USA* 91:10747–10751.

Svendsen et al., (1986) "Complete Amino Acid Sequence of the α–Amylase/Subtilisin Inhbitor from Barley" *Carlsberg Res. Commun.*, 51: 43–50.

Tepfer et al., (1989) "Use of roots transformed by *Agrobacterium rhizogenes* in rhizosphere research: applications in studies of cadmium assimilation from sewage sludges" *Plant Mol. Biol.* 13: 295–302.

Tepfer and Casse–Delbart, (1987) "*Agrobacterium rhizogenes* as a vector for transforming higher plants" *Microbiol. Sci.* 4:24–28.

Van Rie et al., (1989) "Specificity if *Bacillus thurnigiensis*δ–endotoxins" *Eur. J. Biochem* 186:239–47.

Walkerpeach and Velton, (1994) "Agrobacterium–mediated gene transfer to plant cells: cointegrate and binary vector systems" *Plant Molecular Biology Manual*, B1:1–19.

Wells et al., (1986) "Importance of hydrogen–bond formation in stabilizing the transition state of subtilisin" *Phil. Trans. R. Soc. Lond.* A137:415–423.

Wells et al., (1985) "Cassette mutagenesis: an efficient method for generation of multiple mutations at defined sites" *Gene* 34:315–323.

Yu et al., (1997) The *Bacillus thuringiensis* Vegetative Insecticidal Protein Vip3A Lyses.

* cited by examiner

```
                    ┌─ Cry3ba  Mycogen
                 ┌──┤
                 │  └─ Cry3bb  Ecogen
              ┌──┤
              │  │  ┌─ Cry3aa  Abbott
              │  └──┤
              │     └─ Cry3aa  PGS
              │
              │     ┌─ Cry1ic  Zeneca
              │  ┌──┤
              │  │  └─ Cry1Ka  Korea
              ├──┤
              │  │     ┌─ Cry1ba  Cambridge
              │  │  ┌──┤
              │  └──┤  └─ Cry1bb  Ecogen
              │     ├─── Cry1ba  U Washington
              │     └─── Cry1ka  Korea
              │
              │     ┌─ Cry 14cc  Mycogen
              │  ┌──┤
              │  │  └─ Cry 14cc  Mycogen
              ├──┤
              │  │  ┌─ Cry 14cc  Mycogen
              │  └──┤
              │     └─ Cry 14cc  Mycogen
              │
              ├──── Cry 8cc  Mycogen/Kubota
              │
              ├──── Cry9cc  Hokkaido U
              │
              │     ┌─ Cry2ab  Ecogen
              │  ┌──┤
              ├──┤  └─ Cry2ab  Ecogen
              │  └──── Cry2ac Purdue U
              │
              ├──── Cry18ca  Germany
              │
              └──── Cry 14cc  Mycogen └────┴────┴────┴────
             60   70   80   90    % Identity
```

OPTIMIZATION OF PEST RESISTANCE GENES USING DNA SHUFFLING

CROSS-REFERENCE TO RELATED APPLICATIONS

This application claims the benefit of Ser. No. 09/071,816, filed May 1, 1998 (converted to provisional application Ser. No. 60/122,054), and provisional application No. 60/094,462, filed Jul. 28, 1998.

COPYRIGHT NOTIFICATION

Pursuant to 37 C.F.R. 1.71 (e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention pertains to the field of development of optimized genes that can render plants resistant to insects, nematodes, fungi, and other pests.

BACKGROUND OF THE INVENTION

Genes coding for proteins with insecticidal activities are currently used in agriculture to control specific pests (Asgrow Reports—Genetic Engineering for Pest Control—Len Copping, Chapters 2.1–2.4). For example, genes coding for *Bacillus thuringiensis* (Bt) crystal proteins have been incorporated stably in several crops and are widely used as insect control agents (*Pest. Sci.* (1998) 52:165–175, Asgrow Reports, Supra.). Several other examples of different genes coding for insecticidal activity are also known (Asgrow Reports, supra.). However, the greatest limitation to using many of these genes is lack of sufficient activity (potency) and/or lack of useful spectrum of activity. For example, even the most widely used family of genes coding of crystal proteins are limited with respect to the pests they control and potency vs. various economically important pests (Asgrow Reports, supra.). For example, Bt toxins are weak versus corn root worms and other coleopteran pests.

Thus, a need exists for toxins that exhibit improved properties against various plant pests, and for methods of obtaining such toxins. Surprisingly, the present invention provides a strategy for solving each of the problems outlined above, as well as providing a variety of other features which will become apparent upon complete review of the following material.

SUMMARY OF THE INVENTION

The invention provides methods of obtaining an optimized recombinant pest resistance gene which can confer resistance to a pest upon a plant in which the gene is expressed. The methods involve (1) recombining a plurality of forms of a nucleic acid which comprise segments derived from a gene which can confer upon a plant resistance to a pest, wherein the plurality of forms of the nucleic acid differ from each other in two or more nucleotides, to produce a library of recombinant pest resistance genes; and (2) screening the library to identify at least one optimized recombinant pest resistance gene that exhibits improved pest resistance capability compared to a non-recombinant pest resistance gene.

In some embodiments, the methods also involve (3) recombining at least one optimized recombinant pest resistance gene with a further form of the pest resistance gene, which is the same or different from one or more of the plurality of nucleic acid forms of (1), to produce a further library of recombinant pest resistance genes; (4) screening the further library to identify at least one further optimized recombinant pest resistance gene that exhibits a further improvement in pest resistance capability compared to a non-recombinant pest resistance gene; and (5) repeating (3) and (4), as necessary, until the further optimized recombinant vector module that exhibits a further improvement in pest resistance capability compared to a non-recombinant pest resistance gene.

The invention also provides libraries that contain a plurality of recombinant pest resistance genes, wherein each recombinant pest resistance gene contains different permutations of segments of a gene which can confer upon a plant resistance to the pest.

BRIEF DESCRIPTION OF THE DRAWINGS

FIG. 4 presents a dendogram that shows the similarity among various types of Cry1, Cry3, Cry7, Cry8, Cry 14, and Cry18 toxins.

Definitions

Figure 1:
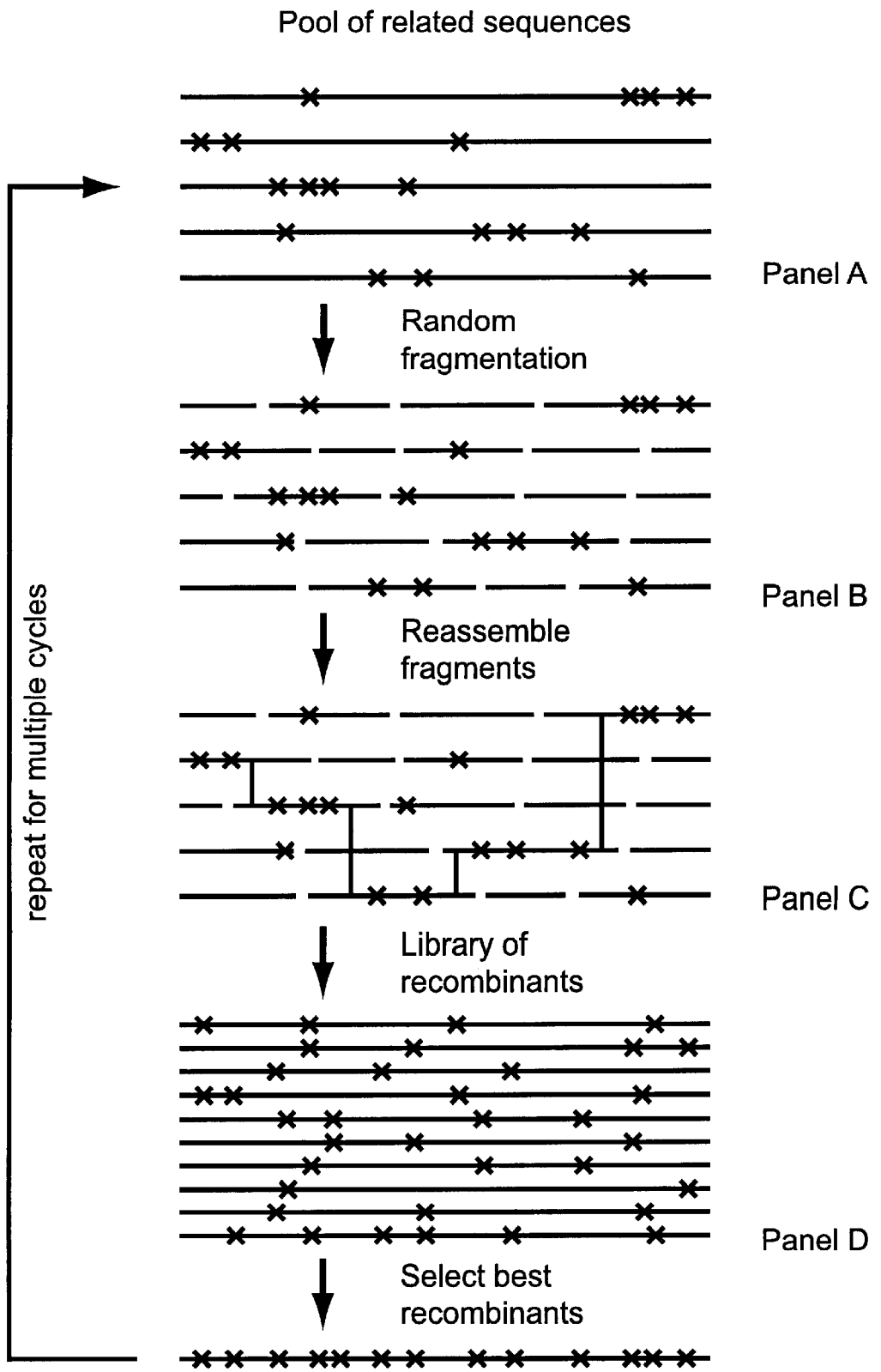
FIG. 1 shows a scheme for in vitro shuffling, "recursive sequence recombination," of genes.

The term "screening" describes what is, in general, a two-step process in which one first determines which cells do and do not express a screening marker and then physically separates the cells having the desired property. Selection is a form of screening in which identification and physical separation are achieved simultaneously by expression of a selection marker, which, in some genetic circumstances, allows cells expressing the marker to survive while other cells die (or vice versa). Screening markers include luciferase, beta-galactosidase, and green fluorescent protein. Selection markers include drug and toxin resistance genes. Although spontaneous selection can and does occur in the course of natural evolution, in the present methods selection is performed by man.

A "exogenous DNA segment," "heterologous sequence" or a "heterologous nucleic acid," as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of DNA shuffling. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

The term "gene" is used broadly to refer to any segment of DNA associated with a biological function. Thus, genes include coding sequences and/or the regulatory sequences required for their expression. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

By "an insecticidally effective part" of the a pest resistance gene is meant a DNA sequence encoding a polypeptide which has fewer amino acids than the respective full-length polypeptide encoded by the pest resistance gene, but which is still toxic to the target pest.

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to essentially one band in an electrophoretic gel. Particularly, it means that the nucleic acid or protein is at least about 50% pure, more preferably at least about 85% pure, and most preferably at least about 99% pure.

The term "naturally-occurring" is used to describe an object that can be found in nature as distinct from being artificially produced by man. For example, a polypeptide or polynucleotide sequence that is present in an organism (including viruses) that can be isolated from a source in nature and which has not been intentionally modified by man in the laboratory is naturally-occurring.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19: 5081; Ohtsuka et al. (1985) *J. Biol. Chem.* 260: 2605–2608; Cassol et al. (1992); Rossolini et al. (1994) *Mol. Cell. Probes* 8: 91–98). The term nucleic acid is used interchangeably with gene, cDNA, and mRNA encoded by a gene.

"Nucleic acid derived from a gene" refers to a nucleic acid for whose synthesis the gene, or a subsequence thereof, has ultimately served as a template. Thus, an mRNA, a cDNA reverse transcribed from an mRNA, an RNA transcribed froth that cDNA, a DNA amplified from the cDNA, an RNA transcribed from the amplified DNA, etc., are all derived from the gene and detection of such derived products is indicative of the presence and/or abundance of the original gene and/or gene transcript in a sample.

A nucleic acid is "operably linked" when it is placed into a functional relationship with another nucleic acid sequence. For instance, a promoter or enhancer is operably linked to a coding sequence if it increases the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A specific binding affinity between two molecules, for example, a ligand and a receptor, means a preferential binding of one molecule for another in a mixture of molecules. The binding of the molecules can be considered specific if the binding affinity is about $1\times10^4$ $M^{-1}$ to about $1\times10^6$ $M^{-1}$ or greater.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence to which test sequences are compared.

When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul el al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff(1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul (1993) *Proc. Nat'l. Acad Sci. USA* 90:5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to," refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization conditions" and "stringent hybridization wash conditions" in the context of nucleic acid hybridization experiments such as Southern and northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, infra., for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

A further indication that two nucleic acid sequences or polypeptides are substantially identical is that the polypeptide encoded by the first nucleic acid is immunologically cross reactive with, or specifically binds to, the polypeptide encoded by the second nucleic acid. Thus, a polypeptide is typically substantially identical to a second polypeptide, for example, where the two peptides differ only by conservative substitutions.

The phrase "specifically (or selectively) binds to an antibody" or "specifically (or selectively) immunoreactive with," when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised to the protein with the amino acid sequence encoded by any of the polynucleotides of the invention can be selected to obtain antibodies specifically immunoreactive with that protein and not with other proteins except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See Harlow and Lane (1988) *Antibodies, A Laboratory Manual*, Cold Spring Harbor Publications, New York "Harlow and Lane"), for a description of immunoassay formats and conditions that can be used to determine specific immunoreactivity. Typically a specific or selective reaction will be at least twice background signal or noise and more typically more than 10 to 100 times background.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I), Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton (1984) Proteins, W. H. Freeman and Company. In addition, individual substitutions, deletions or additions which alter, add or delete a single amino acid or a small percentage of amino acids in an encoded sequence are also "conservatively modified variations."

Two nucleic acids "correspond" when they have the same sequence, or when one nucleic acid is a subsequence of the other, or when one sequence is derived, by natural or artificial manipulation from the other. A nucleic acid corresponds to a protein when it encodes the protein or a substantial fragment of the protein (typically a fragment of at least about 5% of the protein).

A "subsequence" refers to a sequence of nucleic acids or amino acids that comprise a part of a longer sequence of nucleic acids or amino acids (e.g., polypeptide) respectively.

Nucleic acids are "elongated" when additional nucleotides (or other analogous molecules) are incorporated into the nucleic acid. Most commonly, this is performed with a polymerase (e.g., a DNA polymerase), e.g., a polymerase which adds sequences at the 3' terminus of the nucleic acid.

Two nucleic acids are "recombined" when sequences from each of the two nucleic acids are combined in a progeny nucleic acid. Two sequences are "directly" recombined when both of the nucleic acids are substrates for recombination. Two sequences are "indirectly recombined" when the sequences are recombined using an intermediate such as a cross-over oligonucleotide. For indirect recombination, no more than one of the sequences is an actual substrate for recombination, and in some cases, neither sequence is a substrate for recombination.

DETAILED DESCRIPTION

I. Introduction

The present invention provides methods for evolving, i.e., modifying, a nucleic acid for the acquisition of, or an improvement in, a property or characteristic useful in conferring upon plants resistance to pests, including, but not limited to, insects, nematodes, fungi, and arachnids. The methods involve using DNA shuffling to obtain recombinant pest resistance genes that, when present in or on a plant, enhance the plant's defenses against a pest. The invention provides significant advantages over previously used methods for optimization of pest resistance genes. For example, DNA shuffling can result in optimization of a desirable property even in the absence of a detailed understanding of the mechanism by which the particular property is mediated. Sequence recombination can be achieved in many different formats and permutations of formats, as described in further detail below. These formats share some common principles.

The substrates for this modification, or evolution, vary in different applications, as does the property sought to be acquired or improved. Examples of candidate substrates for acquisition of a property or improvement in a property include genes that encode insecticidal proteins. The methods require at least two variant forms of a starting substrate. The variant forms of candidate substrates can show substantial sequence or secondary structural similarity with each other, but they should also differ in at least two positions. The initial diversity between forms can be the result of natural variation, e.g., the different variant forms (homologs) are obtained from different individuals or strains of an organism (including geographic variants) or constitute related sequences from the same organism (e.g., allelic variations).

Alternatively, the initial diversity can be induced, e.g., the second variant form can be generated by error-prone transcription, such as an error-prone PCR or use of a polymerase which lacks proof-reading activity (see, Liao (1990) Gene 88:107–111), of the first variant form, or, by replication of the first form in a mutator strain (mutator host cells are discussed in further detail below). The initial diversity between substrates is greatly augmented in subsequent steps of recombination.

The properties or characteristics that can be sought to be acquired or improved vary widely, and, of course depend on the choice of substrate. For example, for pest resistance genes, properties that one can improve include, but are not limited to, increased range of pests against which a particular resistance gene is effective, increased potency against a pest, delay or elimination of the ability of pests to develop resistance to the gene product, increased expression level of the resistance gene, increased resistance to protease degradation and to destabilizing conditions such as low or high pH, and reduced toxicity to the host plant. At least two variant forms of a nucleic acid which can confer pest resistance are recombined to produce a library of recombinant pest resistance genes. The library is then screened to identify at least one recombinant pest resistance gene that is optimized for the particular property or properties of interest. The variant forms of candidate pest resistance genes can have substantial sequence or secondary structural similarity with each other, but they should also differ in at least two positions. The initial diversity between forms can be the result of natural variation, e.g., the different variant forms (homologs) are obtained from different individuals or strains of an organism (including geographic variants; termed "family shuffling") or constitute related sequences from the same organism (e.g., allelic variations). Alternatively, the initial diversity can be induced, e.g., the second variant form can be generated by error-prone transcription, such as an error-prone PCR or use of a polymerase which lacks proof-reading activity (see, Liao (1990) Gene 88:107–111), of the first variant form, or, by replication of the first form in a mutator strain (mutator host cells are discussed in further detail below).

Often, improvements are achieved after one round of recombination and selection. However, recursive sequence recombination can be employed to achieve still further improvements in a desired property. Recursive sequence recombination entails successive cycles of recombination to generate molecular diversity. That is, one creates a family of nucleic acid molecules showing some sequence identity to each other but differing in the presence of mutations. In any given cycle, recombination can occur in vivo or in vitro, intracellularly or extracellularly. Furthermore, diversity resulting from recombination can be augmented in any cycle by applying prior methods of mutagenesis (e.g., error-prone PCR or cassette mutagenesis) to either the substrates or products for recombination. In some instances, a new or improved property or characteristic can be achieved after only a single cycle of in vivo or in vitro recombination, as when using different, variant forms of the sequence, such as homologs from different individuals or strains of an organism, or related sequences from the same organism, as allelic variations.

A recombination cycle is usually followed by at least one cycle of screening or selection for molecules having a desired property or characteristic. If a recombination cycle is performed in vitro, the products of recombination, i.e., recombinant segments, are sometimes introduced into cells before the screening step. Recombinant segments can also be linked to an appropriate vector or other regulatory sequences before screening. Alternatively, products of recombination generated in vitro are sometimes packaged as viruses before screening. If recombination is performed in vivo, recombination products can sometimes be screened in the cells in which recombination occurred. In other applications, recombinant segments are extracted from the cells, and optionally packaged as viruses, before screening.

The nature of screening or selection depends on what property or characteristic is to be acquired or the property or characteristic for which improvement is sought, and many examples are discussed below. It is not usually necessary to understand the molecular basis by which particular products of recombination (recombinant segments) have acquired new or improved properties or characteristics relative to the starting substrates. For example, a pest resistance gene can have many component sequences each having a different intended role (e.g., coding sequence, regulatory sequences, targeting sequences, stability-conferring sequences, and sequences affecting integration). Each of these component sequences can be varied and recombined simultaneously. Screening/selection can then be performed, for example, for recombinant segments that have increased ability to confer pest resistance upon a plant without the need to attribute such improvement to any of the individual component sequences of the vector.

Depending on the particular screening protocol used for a desired property, initial round(s) of screening can sometimes be performed using bacterial cells due to high transfection efficiencies and ease of culture. Later rounds, and other types of screening which are not amenable to screening in bacterial cells, are performed in plant cells to optimize recombinant segments for use in an environment close to that of their intended use. Final rounds of screening can be performed in the precise cell type of intended use (e.g., a cell which is present in a plant). In some methods, use of a recombinant pest resistance gene can itself be used as a round of screening. That is, recombinant pest resistance genes that are successfully taken up and/or expressed by the intended target cells are recovered from those target cells and used to confer resistance upon other plants. The recombinant pest resistance genes that are recovered from the first target cells are enriched for genes that have evolved, i.e., have been modified by recursive sequence recombination, toward improved or new properties or characteristics for specific uptake and integration of the gene, effectiveness against the pest, stability, and the like.

The screening or selection step identifies a subpopulation of recombinant segments that have evolved toward acquisition of a new or improved desired property or properties useful in conferring pest resistance upon plants. Depending on the screen, the recombinant segments can be identified as components of cells, components of viruses or in free form. More than one round of screening or selection can be performed after each round of recombination.

If further improvement in a property is desired, at least one and usually a collection of recombinant segments surviving a first round of screening/selection are subject to a further round of recombination. These recombinant segments can be recombined with each other or with exogenous segments representing the original substrates or further variants thereof Again, recombination can proceed in vitro or in vivo. If the previous screening step identifies desired recombinant segments as components of cells, the components can be subjected to further recombination in vivo, or can be subjected to further recombination in vitro, or can be isolated before performing a round of in vitro recombination. Conversely, if the previous screening step identifies desired recombinant segments in naked form or as components of viruses, these segments can be introduced into cells to perform a round of in vivo recombination. The second round of recombination, irrespective how performed, generates further recombinant segments which encompass additional diversity than is present in recombinant segments resulting from previous rounds.

The second round of recombination can be followed by a further round of screening/selection according to the principles discussed above for the first round. The stringency of screening/selection can be increased between rounds. Also, the nature of the screen and the property being screened for can vary between rounds if improvement in more than one property is desired or if acquiring more than one new property is desired. Additional rounds of recombination and screening can then be performed until the recombinant segments have sufficiently evolved to acquire the desired new or improved property or function.

The practice of this invention involves the construction of recombinant nucleic acids and the expression of genes in transfected host cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Sambrook et al. (1989) *Molecular Cloning: A Laboratory Manual,* 2nd Ed., Vols. 1–3, Cold Spring Harbor Laboratory ("Sambrook"); Berger and Kimmel, *Guide to Molecular Cloning Techniques, Methods in Enzymology* volume 152 Academic Press, Inc., San Diego, Calif. ("Berger"); and *Current Protocols in Molecular Biology,* F. M. Ausubel et al., eds., Current Protocols, a joint venture between Greene Publishing Associates, Inc. and John Wiley & Sons, Inc., (1994 Supplement) ("Ausubel").

II. Formats for Sequence Recombination

The methods of the invention entail performing recombination ("shuffling") and screening or selection to "evolve" individual genes, whole plasmids or viruses, multigene clusters, or even whole genomes (Stemmer (1995) *Bio/Technology* 13:549–553). Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to natural pairwise recombination events (e.g., as occur during sexual replication). Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

A number of publications by the inventors and their co-workers describe DNA shuffling. Stemmer et al. (1994) "Rapid Evolution of a Protein" *Nature* 370:389–391; Stemmer (1994) "DNA Shuffling by Random Fragmentation and Reassembly: in vitro Recombination for Molecular Evolution," *Proc. Natl. Acad. USA* 91:10747–10751; Stemmer U.S. Pat. No. 5,603,793 METHODS FOR IN VITRO RECOMBINATION; Stemmer et al. U.S. Pat. No. 5,830,721 DNA MUTAGENESIS BY RANDOM FRAGMENTATION AND REASSEMBLY and Stemmer et al. U.S. Pat. No. 5,811,238 METHODS FOR GENERATING POLYNUCLEOTIDES HAVING DESIRED CHARACTERISTICS BY ITERATIVE SELECTION AND RECOMBINATION describe e.g., in vitro protein shuffling methods, e.g., by repeated cycles of mutagenesis, shuffling and selection as well as a variety of methods of generating libraries of displayed peptides and antibodies and a variety of DNA reassembly techniques following DNA fragmentation, and their application to mutagenesis in vitro and in vivo.

Applications of DNA shuffling technology have also been developed by the inventors and their co-workers. In addition to the publications noted above, Minshull et al., U.S. Pat. No. 5,837,458 METHODS AND COMPOSITIONS FOR CELLULAR AND METABOLIC ENGINEERING provides for the evolution of new metabolic pathways and the enhancement of bio-processing through recursive shuffling techniques. Crameri et al. (1996), "Construction And Evolution Of Antibody-Phage Libraries By DNA Shuffling" *Nature Medicine* 2(1): 100–103 describe antibody shuffling for antibody phage libraries. Additional details regarding DNA Shuffling can also be found in WO95/22625, WO97/20078, WO96/33207, WO97/33957, WO98/27230, WO97/35966, WO98/31837, WO98/13487, WO98/13485 and WO989/42832.

A number of the publications of the inventors and their co-workers, as well as other investigators in the art also describe techniques which facilitate DNA shuffling, e.g., by providing for reassembly of genes from small fragments of genes, or even oligonucleotides encoding gene fragments. For example, in addition to the publications noted above, Stemmer et al. (1998) U.S. Pat. No. 5,834,252 END COMPLEMENTARY POLYMERASE REACTION describe processes for amplifying and detecting a target sequence (e.g., in a mixture of nucleic acids), as well as for assembling large polynucleotides from fragments.

Creation of Recombinant Libraries

The invention involves creating recombinant libraries of polynucleotides that are then screened to identify those library members that exhibit a desired property, e.g., which encode insecticidal activity. The recombinant libraries can be created using any of the various methods herein, as well as many others which would be apparent to one of skill.

Methods for obtaining recombinant polynucleotides and/or for obtaining diversity in nucleic acids used as the substrates for DNA shuffling as described below include, for example, homologous recombination (PCT/US98/05223; Publ. No. WO98/42727); oligonucleotide-directed mutagenesis (for review see, Smith, *Ann. Rev. Genet.* 19: 423–462 (1985); Botstein and Shortle, *Science* 229: 1193–1201 (1985); Carter, *Biochem. J* 237: 1–7 (1986); Kunkel, "The efficiency of oligonucleotide directed mutagenesis" in *Nucleic acids & Molecular Biology,* Eckstein and Lilley, eds., Springer Verlag, Berlin (1987)). Included among these methods are oligonucleotide-directed mutagenesis (Zoller and Smith, *Nucl. Acids Res.* 10: 6487–6500 (1982), *Methods in Enzyrnol.* 100: 468–500 (1983), and *Methods in Enzymol.* 154: 329–350 (1987)) phosphothioate-modified DNA mutagenesis (Taylor et al., *Nucl. Acids Res.* 13: 8749–8764 (1985); Taylor et al., *Nucl. Acids Res.* 13: 8765–8787 (1985); Nakamaye and Eckstein, *Nucl. Acids Res.* 14: 9679–9698 (1986); Sayers et al., *Nucl. Acids Res.* 16: 791–802 (1988); Sayers et al., *Nucl. Acids Res.* 16: 803–814 (1988)), mutagenesis using uracil-containing templates (Kunkel, *Proc. Nat'l. Acad. Sci. USA* 82: 488–492 (1985)

and Kunkel et al., *Methods in Enzymol.* 154: 367–382)); mutagenesis using gapped duplex DNA (Kramer et al., *Nucl. Acids Res.* 12: 9441–9456 (1984); Kramer and Fritz, *Methods in Enzymol.* 154: 350–367 (1987); Kramer et al., *Nucl. Acids Res.* 16: 7207 (1988)); and Fritz et al., *Nucl. Acids Res.* 16: 6987–6999 (1988)). Additional suitable methods include point mismatch repair (Kramer et al., *Cell* 38: 879–887 (1984)), mutagenesis using repair-deficient host strains (Carter et al, *Nucl. Acids Res.* 13: 4431–4443 (1985); Carter, *Methods in Enzymol.* 154: 382–403 (1987)), deletion mutagenesis (Eghtedarzadeh and Henikoff, *Nucl. Acids Res.* 14: 5115 (1986)), restriction-selection and restriction-purification (Wells et al., *Phil. Trans. R. Soc. Lond.* A 317: 415–423 (1986)), mutagenesis by total gene synthesis (Nambiar et al., *Science* 223: 1299–1301 (1984); Sakamar and Khorana, *Nucl. Acids Res.* 14: 6361–6372 (1988); Wells et al., *Gene* 34: 315–323 (1985); and Grundström et al., *Nucl. Acids Res.* 13: 3305–3316 (1985). Kits for mutagenesis are commercially available (e.g., Bio-Rad, Amersham International, Anglian Biotechnology).

In a presently preferred embodiment, the recombinant libraries are prepared using DNA shuffling. The shuffling and screening or selection can be used to "evolve" individual genes, whole plasmids or viruses, multigene clusters, or even whole genomes (Stemmer (1995) *Bio/Technology* 13:549–553).

Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to traditional, pairwise recombination events. Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

Exemplary formats and examples for sequence recombination, sometimes referred to as DNA shuffling, evolution, or molecular breeding, have been described by the present inventors and co-workers in the following co-pending applications, patents, and publications: U.S. Pat. No. 5,605,793, issued Feb. 25, 1997, Ser. No. PCT/US95/02127, filed, Feb. 17, 1995, U.S. Pat. No. 5,834,252, issued Nov. 10, 1998, U.S. Pat. No. 5,830,721, issued Nov. 3, 1998, U.S. Pat. No. 5,811,238, issued Sep. 22, 1998, U.S. Pat. No. 6,117,679, issued Sep. 12, 2000, Ser. No. 08/621,430, filed Mar. 25, 1996, Ser. No. PCT/US96/05480, filed Apr. 18, 1996, U.S. Pat. No. 5,837,458, issued Nov. 17, 1998, U.S. Pat. No. 5,928,905, issued Jul. 27, 1999, Ser. No. 08/721,824, filed Sep. 27, 1996, Ser. No. PCT/US97/17300, filed Sep. 26, 1997, and Ser. No. PCT/US97/24239, filed Dec. 17, 1997, Stemmer, *Science* 270:1510 (1995); Stemmer et al., *Gene* 164:49–53(1995); Stemmer, *Bio/Technology* 13:549–553 (1995); Stemmer, *Proc. Natl. Acad. Sci. U.S.A.* 91:10747–10751(1994); Stemmer *Nature* 370:389–391 (1994); Crameri et al., *Nature Medicine* 2(1):1–3 (1996); Crameri et al., *Nature Biotechnology* 14:315–319 (1996), each of which is incorporated by reference in its entirety for all purposes.

Additional Shuffling Format Information

The methods of the invention entail performing recombination ("shuffling") and screening or selection to "evolve" individual genes, whole plasmids or viruses, multigene clusters, or even whole genomes (Stemmer (1995) *Bio/Technology* 13:549–553). Reiterative cycles of recombination and screening/selection can be performed to further evolve the nucleic acids of interest. Such techniques do not require the extensive analysis and computation required by conventional methods for polypeptide engineering. Shuffling allows the recombination of large numbers of mutations in a minimum number of selection cycles, in contrast to traditional, pairwise recombination events. Thus, the sequence recombination techniques described herein provide particular advantages in that they provide recombination between mutations in any or all of these, thereby providing a very fast way of exploring the manner in which different combinations of mutations can affect a desired result. In some instances, however, structural and/or functional information is available which, although not required for sequence recombination, provides opportunities for modification of the technique.

Exemplary formats and examples for sequence recombination, sometimes referred to as DNA shuffling, evolution, or molecular breeding, have been described by the present inventors and co-workers in the following patents and patent applications: U.S. Pat. No. 5,605,793; PCT Application WO 95/22625 (Ser. No. PCT/US95/02126), filed Feb. 17 1995; U.S. Pat. No. 5,834,252, issued Nov. 10, 1998; U.S. Ser. No. 08/621,430, filed Mar. 25, 1996; PCT Application WO 97/20078 (Ser. No. PCT/US96/05480), filed Apr. 18, 1996; PCT Application WO 97/35966, filed Mar. 20, 1997; U.S. Pat. No. 5,928,905, issued Jul. 27, 1999; U.S. Ser. No. 08/721,824, filed Sep. 27, 1996; PCT Application WO 98/13487, filed Sep. 26, 1887; Stemmer, *Science* 270:1510 (1995); Stemmer et al., *Gene* 164:49–53 (1995); Stemmer, *Bio/Technology* 13:549–553 (1995); Stemmer, *Proc. Natl. Acad. Sci. U.S.A.* 91:10747–10751 (1994); Stemmer, *Nature* 370:389–391 (1994); Crameri et al., *Nature Medicine* 2(1):1–3 (1996); Crameri et al., *Nature Biotechnology* 14:315–319 (1996), each of which is incorporated by reference in its entirety for all purposes.

The breeding procedure starts with at least two substrates that generally show substantial sequence identity to each other (i.e., at least about 30%, 50%, 70%, 80% or 90% sequence identity), but differ from each other at certain positions. The difference can be any type of mutation, for example, substitutions, insertions and deletions. Often, different segments differ from each other in perhaps 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second as a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily such as the *Bacillus thuringiensis* toxin family). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the sequence recombination formats provided herein to generate a diverse library of recombinant DNA segments. Such a library can vary widely in size from having fewer than 10 to more than $10^5$, $10^9$, or $10^{12}$ members. In some embodiments, the starting segments and the recombinant libraries generated will include full-length coding sequences and any essential regulatory sequences, such as a promoter and polyadenylation sequence, required for expression. In other embodiments, the recombinant DNA segments in the library can be inserted into a common vector providing sequences necessary for expression before performing screening/selection.

A. Use of Restriction Enzyme Sites to Recombine Mutations

In some situations it is advantageous to use restriction enzyme sites in nucleic acids to direct the recombination of mutations in a nucleic acid sequence of interest. These techniques are particularly preferred in the evolution of fragments that cannot readily be shuffled by existing methods due to the presence of repeated DNA or other problematic primary sequence motifs. These situations also include recombination formats in which it is preferred to retain certain sequences unmutated. The use of restriction enzyme sites is also preferred for shuffling large fragments (typically greater than 10 kb), such as gene clusters that cannot be readily shuffled and "PCR-amplified" because of their size. Although fragments up to 50 kb have been reported to be amplified by PCR (Barnes, *Proc. Natl. Acad. Sci. U.S.A.* 91:2216–2220 (1994)), it can be problematic for fragments over 10 kb, and thus alternative methods for shuffling in the range of 10–50 kb and beyond are preferred. Preferably, the restriction endonucleases used are of the Class II type (Sambrook et al., *Molecular Cloning*, CSH Press, 1987) and of these, preferably those which generate nonpalindromic sticky end overhangs such as Alwn I, Sfi I or BstXl. These enzymes generate nonpalindromic ends that allow for efficient ordered reassembly with DNA ligase. Typically, restriction enzyme (or endonuclease) sites are identified by conventional restriction enzyme mapping techniques (Sambrook et al., supra.), by analysis of sequence information for that gene, or by introduction of desired restriction sites into a nucleic acid sequence by synthesis (i.e. by incorporation of silent mutations).

The DNA substrate molecules to be digested can either be from in vivo replicated DNA, such as a plasmid preparation, or from PCR amplified nucleic acid fragments harboring the restriction enzyme recognition sites of interest, preferably near the ends of the fragment. Typically, at least two variants of a gene of interest, each having one or more mutations, are digested with at least one restriction enzyme determined to cut within the nucleic acid sequence of interest. The restriction fragments are then joined with DNA ligase to generate full length genes having shuffled regions. The number of regions shuffled will depend on the number of cuts within the nucleic acid sequence of interest. The shuffled molecules can be introduced into cells as described above and screened or selected for a desired property as described herein. Nucleic acid can then be isolated from pools (libraries) or clones having desired properties and subjected to the same procedure until a desired degree of improvement is obtained.

In some embodiments, at least one DNA substrate molecule or fragment thereof is isolated and subjected to mutagenesis. In some embodiments, the pool or library of religated restriction fragments are subjected to mutagenesis before the digestion-ligation process is repeated. "Mutagenesis" as used herein comprises such techniques known in the art as PCR mutagenesis, oligonucleotide-directed mutagenesis, site-directed mutagenesis, etc., and recursive sequence recombination by any of the techniques described herein.

B. Reassembly PCR

A further technique for recombining mutations in a nucleic acid sequence utilizes "reassembly PCR". This method can be used to assemble multiple segments that have been separately evolved into a full length nucleic acid template such as a gene. This technique is performed when a pool of advantageous mutants is known from previous work or has been identified by screening mutants that may have been created by any mutagenesis technique known in the art, such as PCR mutagenesis, cassette mutagenesis, doped oligo mutagenesis, chemical mutagenesis, or propagation of the DNA template in vivo in mutator strains. Boundaries defining segments of a nucleic acid sequence of interest preferably lie in intergenic regions, introns, or areas of a gene not likely to have mutations of interest. Preferably, oligonucleotide primers (oligos) are synthesized for PCR amplification of segments of the nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols such as those discussed herein to assemble randomly fragmented genes. In brief, in an assembly protocol the PCR products are first purified away from the primers, by, for example, gel electrophoresis or size exclusion chromatography. Purified products are mixed together and subjected to about 1–10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments, the resulting reassembled genes are subjected to mutagenesis before the process is repeated.

In a further embodiment, the PCR primers for amplification of segments of the nucleic acid sequence of interest are used to introduce variation into the gene of interest as follows. Mutations at sites of interest in a nucleic acid sequence are identified by screening or selection, by sequencing homologues of the nucleic acid sequence, and so on. Oligonucleotide PCR primers are then synthesized which encode wild type or mutant information at sites of interest. These primers are then used in PCR mutagenesis to generate libraries of full length genes encoding permutations of wild type and mutant information at the designated positions. This technique is typically advantageous in cases where the screening or selection process is expensive, cumbersome, or impractical relative to the cost of sequencing the genes of mutants of interest and synthesizing mutagenic oligonucleotides.

C. Site Directed Mutagenesis (SDM) with Oligonucleotides Encoding Homologue Mutations Followed by Shuffling In some embodiments of the invention, sequence information from one or more substrate sequences is added to a given "parental" sequence of interest, with subsequent recombination between rounds of screening or selection. Typically, this is done with site-directed mutagenesis performed by techniques well known in the art (Sambrook et al., supra.) with one substrate as template and oligonucleotides encoding single or multiple mutations from other substrate sequences, e.g. homologous genes. After screening or selection for an improved phenotype of interest, the selected recombinant(s) can be further evolved using RSR techniques described herein. After screening or selection, site-directed mutagenesis can be done again with another collection of oligonucleotides encoding homologue mutations, and the above process repeated until the desired properties are obtained.

When the difference between two homologues is one or more single point mutations in a codon, degenerate oligonucleotides can be used that encode the sequences in both homologues. One oligonucleotide can include many such degenerate codons and still allow one to exhaustively search all permutations over that block of sequence.

When the homologue sequence space is very large, it can be advantageous to restrict the search to certain variants. Thus, for example, computer modeling tools (Lathrop et al. (1996) *J. Mol. Biol.*, 255: 641–665) can be used to model each homologue mutation onto the target protein and discard any mutations that are predicted to grossly disrupt structure and function.

D. In Vitro DNA Shuffling Formats

One embodiment for shuffling DNA sequences in vitro is illustrated in FIG. 1. The initial substrates for recombination are a pool of related sequences, e.g., different, variant forms, as homologs from different individuals, strains, or species of an organism, or related sequences from the same organism, as allelic variations. The X's in FIG. 1, panel A, show where the sequences diverge. The sequences can be DNA or RNA and can be of various lengths depending on the size of the gene or DNA fragment to be recombined or reassembled. Preferably the sequences are from 50 base pairs (bp) to 50 kilobases (kb).

The pool of related substrates are converted into overlapping fragments, e.g., from about 5 bp to 5 kb or more, as shown in FIG. 1, panel B. Often, for example, the size of the fragments is from about 10 bp to 1000 bp, and sometimes the size of the DNA fragments is from about 100 bp to 500 bp. The conversion can be effected by a number of different methods, such as DNase I or RNase digestion, random shearing or partial restriction enzyme digestion. For discussions of protocols for the isolation, manipulation, enzymatic digestion, and the like of nucleic acids, see, for example, Sambrook et al. and Ausubel, both supra. The concentration of nucleic acid fragments of a particular length and sequence is often less than 0.1% or 1% by weight of the total nucleic acid. The number of different specific nucleic acid fragments in the mixture is usually at least about 100, 500 or 1000.

The mixed population of nucleic acid fragments are converted to at least partially single-stranded form using a variety of techniques, including, for example, heating, chemical denaturation, use of DNA binding proteins, and the like. Conversion can be effected by heating to about 80° C. to 100° C., more preferably from 90° C. to 96° C., to form single-stranded nucleic acid fragments and then reannealing. Conversion can also be effected by treatment with single-stranded DNA binding protein (see Wold (1997) *Annu. Rev. Biochem.* 66:61–92) or recA protein (see, e.g., Kiianitsa (1997) *Proc. Natl. Acad. Sci. USA* 94:7837–7840). Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol (PEG), other volume-excluding reagents or salt. The salt concentration is preferably from 0 mM to 200 mM, more preferably the salt concentration is from 10 mM to 100 mM. The salt may be KCl or NaCl. The concentration of PEG is preferably from 0% to 20%, more preferably from 5% to 10%. The fragments that reanneal can be from different substrates as shown in FIG. 1, panel C. The annealed nucleic acid fragments are incubated in the presence of a nucleic acid polymerase, such as Taq or Klenow, and dNTP's (ie. dATP, dCTP, dGTP and dTTP). If regions of sequence identity are large, Taq polymerase can be used with an annealing temperature of between 45–65° C. If the areas of identity are small, Klenow polymerase can be used with an annealing temperature of between 20–30° C. The polymerase can be added to the random nucleic acid fragments prior to annealing, simultaneously with annealing or after annealing.

The process of denaturation, renaturation and incubation in the presence of polymerase of overlapping fragments to generate a collection of polynucleotides containing different permutations of fragments is sometimes referred to as shuffling of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb, as shown in FIG. 1, panel D. The population represents variants of the starting substrates showing substantial sequence identity thereto but also diverging at several positions. The population has many more members than the starting substrates. The population of fragments resulting from shuffling is used to transform host cells, optionally after cloning into a vector.

In one embodiment utilizing in vitro shuffling, subsequences of recombination substrates can be generated by amplifying the full-length sequences under conditions which produce a substantial fraction, typically at least 20 percent or more, of incompletely extended amplification products. Another embodiment uses random primers to prime the entire template DNA to generate less than full length amplification products. The amplification products, including the incompletely extended amplification products are denatured and subjected to at least one additional cycle of reannealing and amplification. This variation, in which at least one cycle of reannealing and amplification provides a substantial fraction of incompletely extended products, is termed "stuttering." In the subsequent amplification round, the partially extended (less than full length) products reanneal to and prime extension on different sequence-related template species. In another embodiment, the conversion of substrates to fragments can be effected by partial PCR amplification of substrates.

In another embodiment, a mixture of fragments is spiked with one or more oligonucleotides. The oligonucleotides can be designed to include precharacterized mutations of a wildtype sequence, or sites of natural variations between individuals or species. The oligonucleotides also include sufficient sequence or structural homology flanking such mutations or variations to allow annealing with the wildtype fragments. Annealing temperatures can be adjusted depending on the length of homology.

In a further embodiment, recombination occurs in at least one cycle by template switching, such as when a DNA fragment derived from one template primes on the homologous position of a related but different template. Template switching can be induced by addition of recA (see, Kiianitsa (1997) supra), rad51(see, Namsaraev (1997) *Mol. Cell. Biol.* 17:5359–5368), rad55 (see, Clever (1997)*EMBO J.* 16:2535–2544), rad57 (see, Sung (1997) *Genes Dev.* 11:1111–1121) or other polymerases (e.g., viral polymerases, reverse transcriptase) to the amplification mixture. Template switching can also be increased by increasing the DNA template concentration.

Another embodiment utilizes at least one cycle of amplification, which can be conducted using a collection of overlapping single-stranded DNA fragments of related sequence, and different lengths. Fragments can be prepared using a single stranded DNA phage, such as M13 (see, Wang (1997) *Biochemistry* 36:9486–9492). Each fragment can hybridize to and prime polynucleotide chain extension of a second fragment from the collection, thus forming sequence-recombined polynucleotides. In a further variation, ssDNA fragments of variable length can be generated from a single primer by Pfu, Taq, Vent, Deep Vent, UlTma DNA polymerase or other DNA polymerases on a first DNA template (see, Cline (1996) *Nucleic Acids Res.* 24:3546–3551). The single stranded DNA fragments are used as primers for a second, Kunkel-type template, consisting of a uracil-containing circular ssDNA. This results in multiple substitutions of the first template into the second. See, Levichkin (1995) *Mol. Biology* 29:572–577; Jung (1992) *Gene* 121:17–24.

In some embodiments of the invention, shuffled nucleic acids obtained by use of the recursive recombination methods of the invention, are put into a cell and/or organism for screening. Shuffled insect resistance genes can be introduced into, for example, bacterial cells, yeast cells, or plant cells for initial screening. Bacillus species (such as *B. subtilis* and *E. coli* are two examples of suitable bacterial cells into which one can insert and express shuffled insect resistance genes. The shuffled genes can be introduced into bacterial or yeast cells either by integration into the chromosomal DNA or as plasmids. Shuffled genes can also be introduced into plant cells for screening purposes. Thus, a transgene of interest can be modified using the recursive sequence recombination methods of the invention in vitro and reinserted into the cell for in vivo/in situ selection for the new or improved property.

E. In Vivo DNA Shuffling Formats

In some embodiments of the invention, DNA substrate molecules are introduced into cells, wherein the cellular machinery directs their recombination. For example, a library of mutants is constructed and screened or selected for mutants with improved phenotypes by any of the techniques described herein. The DNA substrate molecules encoding the best candidates are recovered by any of the techniques described herein, then fragmented and used to transfect a plant host and screened or selected for improved function. If further improvement is desired, the DNA substrate molecules are recovered from the plant host cell, such as by PCR, and the process is repeated until a desired level of improvement is obtained. In some embodiments, the fragments are denatured and reannealed prior to transfection, coated with recombination stimulating proteins such as recA, or co-transfected with a selectable marker such as Neo$^R$ to allow the positive selection for cells receiving recombined versions of the gene of interest. Methods for in vivo shuffling are described in, for example, PCT application WO 98/13487.

The efficiency of in vivo shuffling can be enhanced by increasing the copy number of a gene of interest in the host cells. For example, the majority of bacterial cells in stationary phase cultures grown in rich media contain two, four or eight genomes. In minimal medium the cells contain one or two genomes. The number of genomes per bacterial cell thus depends on the growth rate of the cell as it enters stationary phase. This is because rapidly growing cells contain multiple replication forks, resulting in several genomes in the cells after termination. The number of genomes is strain dependent, although all strains tested have more than one chromosome in stationary phase. The number of genomes in stationary phase cells decreases with time. This appears to be due to fragmentation and degradation of entire chromosomes, similar to apoptosis in mammalian cells. This fragmentation of genomes in cells containing multiple genome copies results in massive recombination and mutagenesis. The presence of multiple genome copies in such cells results in a higher frequency of homologous recombination in these cells, both between copies of a gene in different genomes within the cell, and between a genome within the cell and a transfected fragment. The increased frequency of recombination allows one to evolve a gene evolved more quickly to acquire optimized characteristics.

In nature, the existence of multiple genomic copies in a cell type would usually not be advantageous due to the greater nutritional requirements needed to maintain this copy number. However, artificial conditions can be devised to select for high copy number. Modified cells having recombinant genomes are grown in rich media (in which conditions, multicopy number should not be a disadvantage) and exposed to a mutagen, such as ultraviolet or gamma irradiation or a chemical mutagen, e.g., mitomycin, nitrous acid, photoactivated psoralens, alone or in combination, which induces DNA breaks amenable to repair by recombination. These conditions select for cells having multicopy number due to the greater efficiency with which mutations can be excised. Modified cells surviving exposure to mutagen are enriched for cells with multiple genome copies. If desired, selected cells can be individually analyzed for genome copy number (e.g., by quantitative hybridization with appropriate controls). For example, individual cells can be sorted using a cell sorter for those cells containing more DNA, e.g., using DNA specific fluorescent compounds or sorting for increased size using light dispersion. Some or all of the collection of cells surviving selection are tested for the presence of a gene that is optimized for the desired property.

F. Whole Genome Shuffling

In one embodiment, the selection methods herein are utilized in a "whole genome shuffling" format. An extensive guide to the many forms of whole genome shuffling is found in the pioneering application to the inventors and their co-workers entitled "EVOLUTION OF WHOLE CELLS AND ORGANISMS BY RECURSIVE SEQUENCE RECOMBINATION," filed Jul. 15, 1998 by del Cardayre et al. (U.S. Ser. No. 09/116188) now U.S. Pat. No. 6,326,204.

In brief, whole genome shuffling makes no presuppositions at all regarding what nucleic acids may confer a desired property. Instead, entire genomes (e.g., from a genomic library, or isolated from an organism) are shuffled in cells and selection protocols applied to the cells.

An application of recursive whole genome shuffling is the evolution of plant cells, and transgenic plants derived from the same, to acquire desirable insecticidal protein production properties. The substrates for recombination can be, e.g., whole genomic libraries, fractions thereof or focused libraries containing variants of gene(s) known or suspected to confer tolerance to one of the above agents. Frequently, library fragments are obtained from a different species to the plant being evolved. Regardless of the precise shuffling methodology used, the selection methods described above for insecticidal protein selection, including selection for any of the desirable traits noted herein can be performed.

The DNA fragments are introduced into plant tissues, cultured plant cells or plant protoplasts by standard methods including electroporation (From et al., *Proc. Natl. Acad. Sci. USA* 82, 5824 (1985), infection by viral vectors such as cauliflower mosaic virus (CaMV) (Hohn et al., *Molecular Biology of Plant Tumors*, (Academic Press, New York, 1982) pp. 549–560; Howell, U.S. Pat. No. 4,407,956), high velocity ballistic penetration by small particles with the nucleic acid either within the matrix of small beads or particles, or on the surface (Klein et al., *Nature* 327, 70–73 (1987)), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al., *Science* 233, 496–498 (1984); Fraley et al., *Proc. Natl. Acad. Sci. USA* 80, 4803 (1983)).

Diversity can also be generated by genetic exchange between plant protoplasts. Procedures for formation and fusion of plant protoplasts are described by Takahashi et al., U.S. Pat. No. 4,677,066; Akagi et al., U.S. Pat. No. 5,360,725; Shimamoto et al., U.S. Pat. No. 5,250,433; Cheney et al., U.S. Pat. No. 5,426,040.

After a suitable period of incubation to allow recombination to occur and for expression of recombinant genes, the plant cells are assayed for insecticidal protein, and suitable plant cells are collected. Some or all of these plant cells can be subject to a further round of recombination and screening. Eventually, plant cells having the required degree of insecticidal activity are obtained.

These cells can then be cultured into transgenic plants. Plant regeneration from cultured protoplasts is described in Evans et al., "Protoplast Isolation and Culture," *Handbook of Plant Cell Cultures* 1, 124–176 (MacMillan Publishing Co., New York, 1983); Davey, "Recent Developments in the Culture and Regeneration of Plant Protoplasts," *Protoplasts*, (1983) pp. 12–29, (Birkhauser, Basal 1983); Dale, "Protoplast Culture and Plant Regeneration of Cereals and Other Recalcitrant Crops," *Protoplasts* (1983) pp. 31–41, (Birkhauser, Basel 1983); Binding, "Regeneration of Plants," *Plant Protoplasts*, pp. 21–73, (CRC Press, Boca Raton, 1985) and other references available to persons of skill. Additional details regarding plant regeneration from cells are also found below.

In a variation of the above method, one or more preliminary rounds of recombination and screening can be performed in bacterial cells according to the same general strategy as described for plant cells. More rapid evolution can be achieved in bacterial cells due to their greater growth rate and the greater efficiency with which DNA can be introduced into such cells. After one or more rounds of recombination/screening, a DNA fragment library is recovered from bacteria and transformed into the plants. The library can either be a complete library or a focused library. A focused library can be produced by amplification from primers specific for plant sequences, particularly plant sequences known or suspected to have a role in conferring a insect resistance or a related property.

Plant genome shuffling allows recursive cycles to be used for the introduction and recombination of genes or pathways that confer improved properties to desired plant species. Any plant species, including weeds and wild cultivars, showing a desired trait, such as insect resistance, can be used as the source of DNA that is introduced into the crop or horticultural host plant species.

Genomic DNA prepared from the source plant is fragmented (e.g. by DNaseI, restriction enzymes, or mechanically) and cloned into a vector suitable for making plant genomic libraries, such as pGA482 (An. G., 1995, Methods Mol. Biol. 44:47–58). This vector contains the *A. tumefaciens* left and right borders needed for gene transfer to plant cells and antibiotic markers for selection in *E. coli*, Agrobacterium, and plant cells. A multicloning site is provided for insertion of the genomic fragments. A cos sequence is present for the efficient packaging of DNA into bacteriophage lambda heads for transfection of the primary library into *E. coli*. The vector accepts DNA fragments of 25–40 kb.

The primary library can also be directly electroporated into an *A. tumefaciens* or *A. rhizogenes* strain that is used to infect and transform host plant cells (Main, G D et al., 1995, Methods Mol. Biol. 44:405–412). Alternatively, DNA can be introduced by electroporation or PEG-mediated uptake into protoplasts of the recipient plant species (Bilang et al. (1994) *Plant Mol. Biol Manual*, Kluwer Academic Publishers, A1: 1–16) or by particle bombardment of cells or tissues (Christou, ibid, A2: 1–15). If necessary, antibiotic markers in the T-DNA region can be eliminated, as long as selection for the trait is possible, so that the final plant products contain no antibiotic genes.

Stably transformed whole cells acquiring the trait are selected on solid or liquid media. If the trait in question cannot be selected for directly, transformed cells can be selected with antibiotics and allowed to form callus or regenerated to whole plants and then screened for the desired property.

The second and further cycles consist of isolating genomic DNA from each transgenic line and introducing it into one or more of the other transgenic lines. In each round, transformed cells are selected or screened, typically in an incremental fashion (increasing dosages, etc.). To speed the process of using multiple cycles of transformation, plant regeneration can be eliminated until the last round. Callus tissue generated from the protoplasts or transformed tissues can serve as a source of genomic DNA and new host cells. After the final round, fertile plants are regenerated and the progeny are selected for homozygosity of the inserted DNAs. Ultimately, a new plant is created that carries multiple inserts which additively or synergistically combine to confer high levels of the desired trait.

In addition, the introduced DNA that confers the desired trait can be traced because it is flanked by known sequences in the vector. Either PCR or plasmid rescue is used to isolate the sequences and characterize them in more detail. Long PCR (Foord, O S and Rose, E A, 1995, *PCR Primer: A Laboratory Manual*, CSHL Press, pp 63–77) of the full 25–40 kb insert is achieved with the proper reagents and techniques using as primers the T-DNA border sequences. If the vector is modified to contain the *E. coli* origin of replication and an antibiotic marker between the T-DNA borders, a rare cutting restriction enzyme, such as NotI or SfiI, that cuts only at the ends of the inserted DNA is used to create fragments containing the source plant DNA that are then self-ligated and transformed into *E. coli* where they replicate as plasmids. The total DNA or subfragment of it that is responsible for the transferred trait can be subjected to in vitro evolution by DNA shuffling. The shuffled library is then introduced into host plant cells and screened for improvement of the trait. In this way, single and multigene traits can be transferred from one species to another and optimized for higher expression or activity leading to whole organism improvement.

G. Oligonucleotide and in Silico Shuffling Formats

In addition to the formats for shuffling noted above, at least two additional related formats are useful in the practice of the present invention. The first, referred to as "in silico" shuffling utilizes computer algorithms to perform virtual shuffling using genetic operators in a computer. As applied to the present invention, gene sequence strings corresponding to insect resistance are recombined in a computer system and desirable products are made, e.g., by reassembly PCR of synthetic oligonucleotides. In silico shuffling is described in detail in Selifonov and Stemmer in "METHODS FOR MAKING CHARACTER STRINGS, POLYNUCLEOTIDES & POLYPEPTIDES HAVING DESIRED CHARACTERISTICS" filed Feb. 5, 1999, U.S. Ser. No. 60/118854.

The second useful format is referred to as "oligonucleotide mediated shuffling" in which oligonucleotides corresponding to a family of related homologous nucleic acids (e.g., as applied to the present invention, interspecific or allelic variants of a insect resistance nucleic acid) are recombined to produce selectable nucleic acids. This format is described in detail in Crameri et al. "OLIGONUCLEOTIDE MEDIATED NUCLEIC ACID RECOMBINATION" filed Feb. 5, 1999, U.S. Ser. No. 60/118,813.

In brief, a family of homologous nucleic acid sequences are first aligned, e.g. using available computer software to select regions of identity/similarity and regions of diversity. A plurality (e.g., 2, 5, 10, 20, 50, 75, or 100 or more) oligonucleotides corresponding to at least one region of diversity are synthesized. These oligonucleotides can be shuffled directly, or can be recombined with one or more of the family of nucleic acids. There are several procedures available for shuffling homologous nucleic acids, such as by digesting the nucleic acids with a DNase, permitting recombination to occur and then regenerating full-length templates, i.e., as described in Stemmer (1998) DNA MUTAGENESIS BY RANDOM FRAGMENTATION AND REASSEMBLY U.S. Pat. No. 5,830,721). Thus, in one embodiment, a full-length nucleic acid which is identical to, or homologous with, at least one of the homologous nucleic acids is provided, cleaved with a DNase, and the resulting set of nucleic acid fragments are recombined with the plurality of family gene shuffling oligonucleotides.

Libraries of family gene shuffling oligonucleotides are also provided by oligonucleotide shuffling. For example, homologous genes of interest are aligned using a sequence alignment program such as BLAST, as described above. Nucleotides corresponding to amino acid variations between the homologs are noted. Oligos for synthetic gene shuffling are designed which comprise one (or more) nucleotide difference to any of the aligned homologous sequences, i.e., oligos are designed that are identical to a first nucleic acid, but which incorporate a residue at a position which corresponds to a residue of a nucleic acids homologous, but not identical to the first nucleic acid.

Typically, some or all of the oligonucleotides of a selected length (e.g., about 20, 30, 40, 50, 60, 70, 80, 90, or 100 or more nucleotides) which incorporate all possible nucleic acid variants are made. This includes X oligonucleotides per X sequence variations, where X is the number of different sequences at a locus. The X oligonucleotides are largely identical in sequence, except for the nucleotide(s) representing the variant nucleotide(s). Because of this similarity, it can be advantageous to utilize parallel or pooled synthesis strategies in which a single synthesis reaction or set of reagents is used to make common portions of each oligonucleotide. This can be performed e.g., by well-known solid-phase nucleic acid synthesis techniques, or utilizing array-based oligonucleotide synthetic methods.

Most preferably, the oligonucleotides have at least about 10 bases of sequence identity to either side of a region of variance to ensure reasonably efficient recombination. However, flanking regions with identical bases can have fewer identical bases (e.g., 5, 6, 7, 8, or 9) and can, of course, have larger regions of identity (e.g., 11, 12, 13, 14, 15, 16, 1,7 1,8 ,19, 20, 25, 30, 50, or more).

During gene assembly, oligonucleotides can be incubated together and reassembled using any of a variety of polymerase-mediated reassembly methods, e.g., as described herein and as known to one of skill. Selected oligonucleotides can be "spiked" in the recombination mixture at any selected concentration, thus causing preferential incorporation of desirable modifications.

III. Substrates for Evolution of Optimized Genes Useful in Crop Plants

The invention provides methods of obtaining pest resistance genes that are enhanced in their ability to confer upon plants resistance to pests. The methods involve the use of DNA shuffling to develop libraries of recombinant pest resistance genes, and the screening of these libraries to identify those recombinant genes that exhibit the desired improved properties. The methods are applicable to any nucleic acid that, when present in a plant, or on a plant, can confer resistance upon a pest. Several examples of such nucleic acids are discussed herein; these and others are described in, for example, *Advances in insect control: The role of transgenic plants*, Carozzi and Koziel, eds., Taylor & Francis, New York, 1997. Also provided are methods of obtaining other genes that are optimized for their ability to confer a beneficial effect upon plants. These genes include, for example, genes involved in herbicide selectivity and in nitrogen fixation.

A. Bacillus Toxins and Related Polypeptides

The invention provides methods of obtaining optimized recombinant Bt toxins. Certain species of the gram-positive soil bacterium Bacillus produce proteins that are toxic to insects, arachnids, and nematodes. These proteins include the crystal proteins, known as "Bt toxins," that are produced by *B. thuringiensis* and other Bacillus species. Bt toxins are typically polypeptides of about 130 kDa to 140 kDa or of about 70 kDa, which contain toxic fragments of 60+/−10 kDa (Hofte and Whiteley (1989) *Microbiol. Rev.* 53: 242–255). Bt toxins are highly specific and lack toxicity towards humans and other animals, and plants. Bt toxins are reviewed in, for example, Kumar et al. (1996) *Adv. Appl. Microbiol.* 42: 1–43 and Peferoen (1996) In *Advances in Insect Control*, supra., Chapter 2, pp. 21–48.

Bt toxins produced by different Bacillus species can be classified on the basis similarity of the nucleic acid and amino acid sequences, and also based on the pests against which the toxins are effective (Hofte and Whiteley, supra.; Ogiwara et al. (1995) *Curr. Microbiol.* 30: 227–235). Insecticidal Bt toxins, for example, are active against one or more of the Lepidoptera, Diptera, Coleoptera, or Phthiraptera (Kumar et al., supra.). Bt genes have been classified into at least six major classes: cryI (Lepidoptera specific), cryII (Lepidoptera and Diptera specific), cryIII (Coleoptera specific), cryIV (Diptera specific), cryV, and cryVI (Hofte and Whiteley, supra.; Feitelson et al. (1992) *Biotechnol.* 10: 271–276). Subgroups have also been proposed based on differences in insecticidal spectra, such as cryIC, cryIIA, and cryIIB (Kumar et al., supra.). Another classification is based on amino acid identity of full-length products of Bt toxin genes (Crickmore et al. (1996) *Genes Microbiol. Res.;* Kumar et al., supra.). According to this scheme, Bt toxins are divided into several homology groups, with Cry1, -3, -4, -7, -8, -9, and -10 forming the largest group, Cry2, Cry11, and Cry18 forming the second group, Cry5, -12, -13, and -14 the third group, and the Cyt proteins the fourth group. Cry6, -15, and -16 are unique proteins under this classification scheme. Classification of Bt crystal protein genes, including dendograms showing evolutionary relationships, is also described in Yamamoto and Powell (1993) In *Advanced Engineered Pesticides*, Kim, Ed., Marcel Dekker, pp. 3–42.

The methods of the invention involve performing DNA shuffling using nucleic acids that encode Bt toxins as the substrates. Numerous nucleic acid sequences that encode Bt toxins have been characterized. See, e.g., U.S. Pat. Nos. 5,683,691, 5,633,446, 5,651,965, 5,635,480, 4,766,203, 4,448,885, 4,467,036, 4,797,276, 4,853,331, 4,918,006, 4,849,217, 5,151,363, 4,948,734, and 4,771,131; and European patent publications 0,149,162, 0,213,818 and 193259. Many additional Bt toxin genes are provided in GenBank and other databases. At least some Bt toxins are encoded by plasmid-borne genes (Stahly et al. (1978) *Biochem. Biophys. Res. Commun.* 84: 581–588; Debaboc et al. (1977) *Genetika* 13: 496–501.

Figure 2:
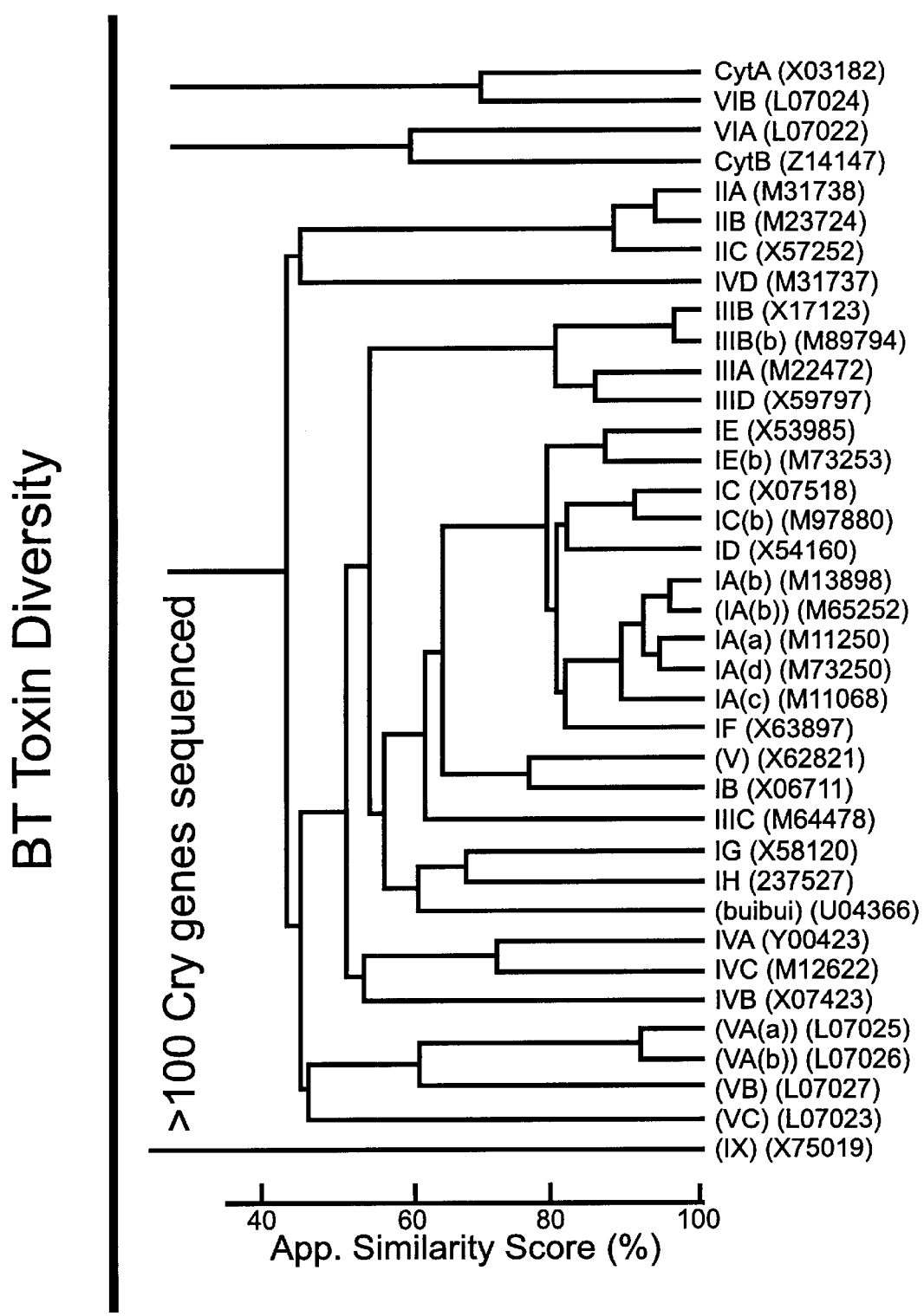
FIG. 2 shows a dendogram of *Bacillus thuringiensis* toxin genes.

Libraries of the recombinant Bt toxin genes are prepared by DNA shuffling. In preferred embodiments, the substrates for DNA shuffling are derived from Bt toxin families. FIG. 2 provides a dendogram showing relationships among many Bt toxin genes. A list of Bt holotype toxins, together with database accession numbers, is provided in Table 1. A list of these and other Bt toxin genes is provided in Table 2.

TABLE 1

List of *Bacillus thuringiensis* Holotype Toxins

| Name | Old Name | Acc Num |
|---|---|---|
| cry1Aa | cryIA(a) | M11250 |
| cry1Ab | cryIA(b) | M13898 |
| cry1Ac | cryIA(c) | M11068 |
| cry1Ad | cryIA(d) | M73250 |
| cry1Ae | cryIA(e) | M65252 |
| cry1Af | icp | U82003 |
| cry1Ag | | AF081248 |
| cry1Ba | cryIB | X06711 |
| cry1Bb | ET5 | L32020 |
| cry1Bc | PEG5 | Z46442 |
| cry1Bd | cryE1 | U70726 |
| cry1Ca | cryIC | X07518 |
| cry1Cb | cryIC(b) | M97880 |
| cry1Da | cryID | X54160 |
| cry1Db | PrtB | Z22511 |
| cry1Ea | cryIE | X53985 |
| cry1be | cryIE(b) | M73253 |
| cry1Fa | cryIF | M63897 |
| cry1Fb | PrtD | Z22512 |
| cry1Ga | PrtA | Z22510 |
| cry1Gb | cryH2 | U70725 |
| cry1Ha | PrtC | Z22513 |
| cry1Hb | | U35780 |
| cry1Ia | cryV | X62821 |
| cry1Ic | | AF056933 |
| cry1Ib | CryV465 | U07642 |
| cry1Ja | ET4 | L32019 |
| cry1Jb | ET1 | U31527 |
| cry1Jc | | 190730 |
| cry1Ka | | U28801 |
| cry2Aa | cryIIA | M31738 |
| cry2Ab | cryIIB | M23724 |
| cry2Ac | cryIIC | X57252 |
| cry3Aa | cryIIIA | M22472 |
| cry3Ba | CryIIIB2 | X17123 |
| cry3Bb | cryIIIBb | M89794 |
| cry3Ca | cryIIID | X59797 |
| cry4Aa | cryIVA | Y00423 |
| cry4Ba | cryIVB | X07423 |
| cry5Aa | cryVA(a) | L07025 |
| cry5Ab | cryVA(b) | L07026 |
| cry5Ac | | I34543 |
| cry5Ba | | U19725 |
| cry6Aa | cryVIA | L07022 |
| cry6Ba | cryVIB | L07024 |
| cry7Aa | cryIIIC | M64478 |
| cry7Ab | cryIIICb | U04367 |
| cry8Aa | cryIIIE | U04364 |
| cry8Ba | cryIIIG | U04365 |
| cry8Ca | cryIIIF | U04366 |
| cry9Aa | cryIG | X58120 |
| cry9Ba | cryIX | X75019 |
| cry9Ca | cryIH | Z37527 |
| cry9Da | | D85560 |
| cry9Ea | | AB011496 |
| cry10Aa | cryIVC | M12662 |
| cry11Aa | cryIVD | M31737 |
| cry11Ba | Jeg80 | X86902 |
| cry11Bb | | AF017416 |
| cry12Aa | cryVB | L07027 |
| cry13Aa | cryVC | L07023 |
| cry14Aa | cryVD | U13955 |
| cry15Aa | 34kDa | M76442 |
| cry16Aa | cbm71 | X94146 |
| cry17Aa | cbm72 | X99478 |
| cry18Aa | cryBP1 | X99049 |
| cry19Aa | Jeg65 | Y07603 |
| cry20Aa | | U82518 |
| cry21Aa | | I32932 |
| cry22Aa | | I34547 |
| cry23Aa | | AF03048 |
| cry24Aa | Jeg72 | U88188 |
| cry25Aa | Jeg74 | U88189 |
| cry26Aa | | AF122897 |
| cry27Aa | | AB023293 |
| cry28Aa | | AF132928 |
| cyt1Aa | cytA | X03182 |
| cyt1Ab | cytM | X98793 |
| cyt1Ba | | U37196 |
| cyt2Aa | cytB | Z14147 |
| cyt2Ba | cytB | U52043 |
| cyt2Bb | | U82519 |

TABLE 2

Bt toxin genes

| Name | Acc. No. | Reference | Year | Journal | Coding |
|---|---|---|---|---|---|
| cry1Aa1 | M11250 | Schnepf et al. | 1985 | JBC 260: 6264–6272 | 527–4054 |
| cry1Aa2 | M10917 | Shibano et al. | 1985 | Gene 34: 243–251 | 153–2955 |
| cry1Aa3 | D00348 | Shimizu et al. | 1988 | ABC 52: 1565–1573 | 73–3600 |
| cry1Aa4 | X13535 | Masson et al. | 1989 | NAR 17: 446–446 | 1–3528 |
| cry1Aa5 | D17518 | Udayasuriyan et al. | 1994 | BBB 58: 830–835 | 81–3608 |
| cry1Aa6 | U43605 | Masson et al. | 1994 | Mol Micro 14: 851–860 | 1–1860 |
| cry1Ab1 | M13898 | Wabiko et al. | 1986 | DNA 5: 305–314 | 142–3606 |
| cry1Ab2 | M12661 | Thorne et al. | 1986 | J. Bact 166: 801–811 | 155–3622 |
| cry1Ab3 | M15271 | Geiser et al. | 1986 | Gene 48: 109–118 | 156–3620 |
| cry1Ab4 | D00117 | Kondo et al. | 1987 | ABC 51: 455–463 | 163–3627 |
| cry1Ab5 | X04698 | Hofte et al. | 1986 | EJB 161: 273–280 | 141–3605 |
| cry1Ab6 | M37263 | Refford et al. | 1987 | J. Biotech 6: 307–322 | 73–3537 |
| cry1Ab7 | X13233 | Haider & Ellar | 1988 | NAR 16: 10927–10927 | 1–3465 |
| cry1Ab8 | M16463 | Oeda et al. | 1987 | Gene 53: 113–119 | 157–3624 |
| cry1Ab9 | X54939 | Chak & Jen | 1993 | PNSCRC 17: 7—14 | 73–3540 |
| cry1Ab10 | A29125 | Fischhoff el al. | 1987 | Bioltechnology 5: 807–813 | peptide seq |
| cry1Ac1 | M11068 | Adang et al. | 1985 | Gene 36: 289–300 | 388–3921 |
| cry1Ac2 | M35524 | Von Tersch et al. | 1991 | ABM 57: 349–358 | 239–3769 |
| cry1Ac3 | X54159 | Dardenne et al. | 1990 | NAR: 18: 5546–5546 | 339–2192 |
| cry1Ac4 | M73249 | Payne et al. | 1991 | U.S. Pat. No. 4990332 | 1–3534 |
| cry1Ac5 | M73248 | Payne et al. | 1992 | U.S. Pat. No. 5135867 | 1–3531 |
| cry1Ac6 | U43606 | Masson et al. | 1994 | Mol. Micro. 14: 851–860 | 1–1821 |
| cry1Ac7 | U87793 | Herrera et al. | 1994 | AEM 60: 682–690 | 976–4509 |
| cry1Ac8 | U87397 | Omolo et al. | 1997 | Curr. Micro. 34: 118–121 | 153–3686 |
| cry1Ac9 | U89872 | Gleave et al. | 1992 | NZJCHS 20: 27–36 | 388–3921 |
| cry1Ac10 | AJ002514 | Sun and Yu | 1997 | unpublished | 388–3921 |
| cry1Ad1 | M73250 | Payne & Sick | 1993 | U.S. Pat. No. 5246852 | 1–3537 |
| cry1Ae1 | M65252 | Lee & Aronson | 1991 | J Bact 173: 6635–6638 | 81–3623 |
| cry1Af1 | U82003 | Kang et al. | 1997 | unpublished | 172–2905 |
| cry1Ba1 | X06711 | Brizzard & Whiteley | 1988 | NAR 16: 2723–2724 | 1–3684 |
| cry1Ba2 | X95704 | Soetaert | 1996 | unpublished | 186–3869 |
| cry1Bb1 | L32020 | Donovan et al. | 1994 | U.S. Pat. No. 5322687 | 67–3753 |
| cry1Bc1 | Z46442 | Bishop et al. | 1994 | unpublished | 141–3839 |
| cry1Bd1 | U70726 | Chak | 1996 | unpublished | 842–4534 |
| cry1Ca1 | X07518 | Honee et al. | 1988 | NAR 16: 6240–6240 | 47–3613 |
| cry1Ca2 | X13620 | Sanchis et al. | 1989 | Mol Micro 3: 229–238 | 241–2711 |
| cry1Ca3 | M73251 | Payne & Sick | 1993 | U.S. Pat. No. 5246852 | 1–3570 |
| cry1Ca4 | A27642 | Van Mellaert et al. | 1990 | EP 0400246 | 234–3800 |
| cry1Ca5 | X96682 | Strizhov | 1996 | unpublished | 1–2268 |
| cry1Ca6 | X96683 | Suizhov | 1996 | unpublished | 1–2268 |
| cry1Ca7 | X96684 | Strizhov | 1996 | unpubiished | 1–2286 |
| cry1Cb1 | M97880 | Kalman et al. | 1993 | AEM 59: 1131–1137 | 296–3823 |
| cry1Da1 | X54160 | Hofte et al. | 1990 | NAR 18: 5545–5545 | 264–3758 |
| cry1Db1 | Z22511 | Lambert | 1993 | unpublished | 241–3720 |
| cry1Ea1 | X53985 | Visser et al. | 1990 | J Bact 172: 6783–6788 | 130–3642 |
| cry1Ea2 | X56144 | Bosse et al. | 1990 | NAR 18:7443-7443 | 1–3513 |
| cry1Ea3 | M73252 | Payne & Sick | 1991 | U.S. Pat. No. 5039523 | 1–3513 |
| cry1Ea4 | U94323 | Ibarra et al. | 1997 | unpublished | 388–3900 |
| cry1Eb1 | M73253 | Payne & Sick | 1993 | U.S. Pat. No. 5206166 | 1–3522 |
| cry1Fa1 | M63897 | Chambers et al. | 1991 | J Bact 173: 3966–3976 | 478–3999 |
| cry1Fa2 | M73254 | Payne & Sick | 1993 | U.S. Pat. No. 5188960 | 1–3525 |
| cry1Fb1 | Z22512 | Lambert | 1993 | unpublished | 483–4004 |
| cry1Fb2 | AB012288 | Masuda & Asano | 1998 | unpublished | 84–3587 |
| cry1Ga1 | Z22510 | Lambert | 1993 | unpublished | 67–3564 |
| cry1Ga2 | Y09326 | Shevelev et al. | 1997 | Febs Lett 404: 148–152 | 692–4210 |
| cry1Gb1 | U70725 | Chak | 1996 | unpublished | 532–4038 |
| cry1Ha1 | Z22513 | Lambert | 1993 | unpublished | 530–4045 |
| cry1Hb1 | U35780 | Koo et al. | 1995 | unpublished | 728–4195 |
| cry1Ia1 | X62821 | Tailor et al. | 1992 | Mol Micro 6: 1211–1217 | 355–2511 |
| cry1Ia2 | M98544 | Gleave et al. | 1993 | AEM 59: 1683–1687 | 1–2160 |
| cry1Ia3 | L36338 | Shin et al. | 1995 | AEM 61: 2402–2407 | 279–2435 |
| cry1Ia4 | L49391 | Kostichka et al. | 1996 | J Bact 178: 2141–2144 | 61–2217 |
| cry1Ia5 | Y08920 | Selvapandiyan | 1996 | unpublished | 524–2680 |
| cry1Ib1 | U07642 | Shin et al. | 1995 | AEM 61: 2402–2407 | 237–2393 |
| cry1Ja1 | L32019 | Donovan et al. | 1994 | U.S. Pat. No. 5322687 | 99–3519 |
| cry1Jb1 | U31527 | Von Tersch & Gonzalez | 1994 | U.S. Pat. No. 5356623 | 177–3686 |
| cry1Ka1 | U28801 | Koo et al. | 1995 | FEMS 134: 159–164 | 451–4098 |
| cry2Aa1 | M31738 | Donovan et al. | 1989 | JBC 264: 4740–4740 | 156–2054 |
| cry2Aa2 | M23723 | Widner & Whiteley | 1989 | J Bact 171: 965–974 | 1840–3738 |
| cry2Aa3 | D86064 | Sasaki et al. | 1997 | Curr Micro 35: 1–8 | 2007–3911 |
| cry2Aa4 | AF047038 | Misra et al. | 1998 | unpublished | 10–1909 |
| cry2Ab1 | M23724 | Widner & Whiteley | 1989 | J Bact 171: 965–974 | 1–1899 |
| cry2Ab2 | X55416 | Dankocsik et al. | 1990 | Mol Micro 4: 2087–2094 | 874–2775 |
| cry2Ac1 | X57252 | Wu et al. | 1991 | FEMS 81: 31–36 | 2125–3990 |
| cry3Aa1 | M22472 | Hermstadt et al. | 1987 | Gene 57: 37–46 | 25–1956 |

TABLE 2-continued

Bt toxin genes

| Name | Acc. No. | Reference | Year | Journal | Coding |
|---|---|---|---|---|---|
| cry3Aa2 | J02978 | Sekar et al. | 1987 | PNAS 84: 7036–7040 | 241–2175 |
| cry3Aa3 | Y00420 | Hofte et al. | 1987 | NAR 15: 7183–7183 | 566–2497 |
| cry3Aa4 | M30503 | McPherson et al. | 1988 | Bio/technology 6: 61–66 | 201–2135 |
| cry3Aa5 | M37207 | Donovan et al. | 1988 | MGG 214: 365–372 | 569–2500 |
| cry1Ic1 | AF056933 | Osman et al. | 1998 | unpublished | 1–2180 |
| cry3Aa6 | U10985 | Adams et al. | 1994 | Mol Micro 14: 381–389 | 569–2500 |
| cry3Ba1 | X17123 | Sick et al. | 1990 | NAR 18: 1305–1305 | 25–1977 |
| cry3Ba2 | A07234 | Peferoen et al. | 1990 | EP 0382990 | 342–2297 |
| cry3Bb1 | M89794 | Donovan et al. | 1992 | AEM 58: 3921–3927 | 202–2157 |
| cry3Bb2 | U31633 | Donovan et al. | 1995 | U.S. Pat. No. 5378625 | 144–2099 |
| cry3Ca1 | X59797 | Lambert et al. | 1992 | Gene 110: 131–132 | 232–2178 |
| cry4Aa1 | Y00423 | Ward & Ellar | 1987 | NAR 15: 7195–7195 | 1–3540 |
| cry4Aa2 | D00248 | Sen et al. | 1988 | ABC 52: 873–878 | 393–3935 |
| cry4Ba1 | X07423 | Chungjatpornchai et al. | 1988 | EJB 173: 9–16 | 157–3564 |
| cry4Ba2 | X07082 | Tungpradubkul et al. | 1988 | NAR 16: 1637–1638 | 151–3558 |
| cry4Ba3 | M20242 | Yamamoto et al. | 1988 | Gene 66: 107–120 | 526–3930 |
| cry4Ba4 | D00247 | Sen et al. | 1988 | ABC 52: 873–878 | 461–3865 |
| cry5Aa1 | L07025 | Sick et al. | 1994 | U.S. Pat. No. 5281530 | 1–4155 |
| cry5Ab1 | L07026 | Narva et al. | 1991 | EP 0462721 | 1–3867 |
| cry5Ac1 | I34543 | Payne et al. | 1997 | U.S. Pat. No. 5596071 | 1–3660 |
| cry5Ba1 | U19725 | Payne et al. | 1997 | U.S. Pat. No. 5596071 | 1–3735 |
| cry6Aa1 | L07022 | Narva et al. | 1993 | U.S. Pat. No. 5236843 | 1–1425 |
| cry6Ba1 | L07024 | Narva et al. | 1991 | EP 0462721 | 1–1185 |
| cry7Aa1 | M64478 | Lambert et al. | 1992 | AEM 58: 2536–2542 | 184–3597 |
| cry7Ab1 | U04367 | Payne & Fu | 1994 | U.S. Pat. No. 5286486 | 1–3414 |
| cry7Ab2 | U04368 | Payne & Fu | 1994 | U.S. Pat. No. 5286486 | 1–3414 |
| cry8Aa1 | U04364 | Foncerrada et al. | 1992 | EP 0498537 | 1–3471 |
| cry8Ba1 | U04365 | Michaels et al. | 1993 | WO 93115206 | 1–3507 |
| cry8Ca1 | U04366 | Ogiwara et al. | 1995 | Curr Micro 30: 227–235 | 1–3447 |
| cry9Aa1 | X58120 | Smulevitch et al. | 1991 | FEBS 293: 25–28 | 5807–9274 |
| cry9Aa2 | X58534 | Gleave et al. | 1992 | JGM 138: 55–62 | 385–3837 |
| cry9Ba1 | X75019 | Shevelev et al. | 1993 | FEBS 336: 79–82 | 26–3488 |
| cry9Ca1 | Z37527 | Lambert et al. | 1996 | AEM 62: 80–86 | 2096–5569 |
| cry9Da1 | D85560 | Asano et al. | 1997 | AEM 63: 1054–1057 | 47–3553 |
| cry9Da2 | AF042733 | Wasano & Ohba | 1998 | unpublished | <1–1937 |
| cry9Ea1 | AB011496 | Midoh and Oyama | 1998 | unpublished | 211–3663 |
| cry10Aa1 | M12662 | Thorne et al. | 1986 | J Bact 166: 801–811 | 941–2965 |
| cry11Aa1 | M31737 | Donovan et al. | 1988 | J Bact 170: 4732–4738 | 41–1969 |
| cry11Aa2 | M22860 | Adams et al. | 1989 | J Bact 171: 521–530 | <1–235 |
| cry11Ba1 | X86902 | Delecluse | 1995 | AEM 61: 4230–4235 | 64–2238 |
| cry11Bb1 | AF017416 | Orduz et al. | 1998 | Biochem. Biophys. Acta 1388: 267–272 | 97–2349 |
| cry12Aa1 | L07027 | Narva et al. | 1991 | EP 0462721 | 1–3771 |
| cry13Aa1 | L07023 | Narva et al. | 1992 | WO 92/19739 | 1–2409 |
| cry14Aa1 | U13955 | Narva et al. | 1994 | WO 94/16079 | 1–3558 |
| cry15Aa1 | M76442 | Brown & Whiteley | 1992 | J Bact 174: 549–557 | 1036–2055 |
| cry16Aa2 | X94146 | Barloy et al. | 1996 | J Bact 178: 3099–3105 | 158–1996 |
| cry17Aa1 | X99478 | Barloy et al. | 1997 | unpublished | 12–1865 |
| cry18Aa1 | X99049 | Zhang et al. | 1997 | J Bact 179: 4336–4341 | 743–2860 |
| cry19Aa1 | Y07603 | Rosso and Delecluse | 1996 | AEM 63: 4449–4455 | 719–2662 |
| Cry19Ba1 | D88381 | | | unpublished | |
| cry20Aa1 | U82518 | Lee & Gill | 1997 | AEM 63: 4664–4670 | 60–2318 |
| cry21Aa1 | I32932 | Payne et al. | 1996 | U.S. Pat. No. 5589382 | 1–3501 |
| cry22Aa1 | I34547 | Payne et al. | 1997 | U.S. Pat. No. 5596071 | 1–2169 |
| cyt1Aa1 | X03182 | Waalwijk et al. | 1985 | NAR 13: 8207–8217 | 140–886 |
| cyt1Aa2 | X04338 | Ward & Ellar | 1986 | JMB 191: 1–11 | 509–1255 |
| cyt1Aa3 | Y00135 | Earp & Ellar | 1987 | NAR 15: 3619–3619 | 36–782 |
| cry24Aa1 | U88188 | Kawalek | 1998 | unpublished | 1–>2024 |
| cry25Aa1 | U88189 | Kawalek | 1998 | unpublished | 1–2028 |
| cry26Aa | AF122897 | Wojtechowska et al. | 1999 | unpublished | 897–4388 |
| cry28Aa1 | AF132928 | Wojtechowska et al. | 1999 | unpublished | 1129–4458 |
| cyt1Aa4 | M35968 | Galjart et al. | 1987 | Curr Micro 16: 171–177 | 67–816 |
| cyt1Ab1 | X98793 | Thiery et al. | 1997 | AEM 63: 468–473 | 28–777 |
| cyt1Ba1 | U37196 | Payne et al. | 1995 | U.S. Pat. No. 5436002 | 1–795 |
| cyt2Aa1 | Z14147 | Koni & Ellar | 1993 | JMB 229: 319–327 | 270–1046 |
| cyt2Ba1 | U52043 | Guerchicoff et al. | 1997 | AEM 63: 2716–2721 | 287–655 |
| cyt2Ba2 | AF020789 | Guerchicoff et al. | 1997 | AEM 63: 2716–2721 | <1–>469 |
| cyt2Ba3 | AF022884 | Guerchicoff et al. | 1997 | AEM 63: 2716–2721 | <1–>469 |
| cyt2Ba4 | AF022885 | Guerchicoff et al. | 1997 | AEM 63: 2716–2721 | <1–>469 |
| cyt2Ba5 | AF022886 | Guerchicoff et al. | 1997 | AEM 63: 2716–2721 | <1–>471 |
| cyt2Ba6 | AF034926 | Guerchicoff et al. | 1997 | AEM 63: 2716–2721 | <1–>472 |
| cyt2Bb1 | U82519 | Cheong & Gill | 1997 | AEM 63: 3254–3260 | 416–1204 |
| 40kDa | M76442 | Brown and Whiteley | 1992 | J Bact 174: 549–557 | 45–971 |
| cryC35 | X92691 | Juarez-Perez et al. | 1995 | unpublished | 1–981 |
| cryTDK | D86346 | Hashimoto | 1996 | unpublished | 177–2645 |

TABLE 2-continued

Bt toxin genes

| Name | Acc. No. | Reference | Year | Journal | Coding |
| --- | --- | --- | --- | --- | --- |
| cryC53 | X98616 | Juarez-Perez et al. | 1996 | unpublished | 1–1005 |
| vip3A(a) | L48811 | Estruch et al. | 1996 | PNAS 93: 5389–5394 | 739–3105 |
| vip3A(b) | L48812 | Estruch et al. | 1996 | PNAS 93: 5389–5394 | 118–2484 |
| p21med | X98794 | Thiery et al. | 1997 | unpublished | 1–552 |
| vip1A | | Warren et al. | 1999 | U.S.Pat. 5872212 | |
| vip2A | | Warren et al. | 1999 | U.S.Pat. 5872212 | |

Expression of the shuffled genes can be achieved in E. coli or any bacilli by using an appropriate expression vector. Most, if not all, Bt toxin promoters associated with cry genes will function in E. coli as well as bacilli. An example of a suitable vector for use in E. coli host cells is described in Sasaki et al. (1996) Curr. Microbiol. 31: 195–200). For high expression in E. coli, a portion of the cry promoter between ApaI and NdeI sites is removed from the vector described by Sasaki et al. In presently preferred embodiments, the vector also includes coding sequences that, when linked in frame to the coding sequence of the shuffled gene, encode an easily detectable and/or immobilizable tag (e.g., multiple His residues).

The cry gene can be truncated to produce a pre-activated Cry protein. It was found in a number of cases that the truncated gene produces a protein that is substantially toxic to E. coli. In preferred embodiments, however, the truncated cry gene is expressed in a bacillus (e.g., Bacillus cereus or B. thuringiensis). A leader sequence can be added to the cry gene so that the protein is secreted into the culture medium. This approach makes the protein isolation process less time consuming.

Those recombinant genes that encode Bt toxins having improvements in one or more desired properties are identified as described herein. Screening methodologies for some of these properties are described in Kumar et al., supra.

The optimized recombinant Bt toxin genes can be used for the production of pesticidal proteins for direct application to plants, can be expressed in microorganisms that colonize plants, or can be introduced into transgenic plants. Bt genes have been expressed in at least twenty-six different plant species (Schuler et al. (1998) Tibtech 16: 168–175). Each of these modes of administration are discussed in more detail below.

B. Protease and α-Amylase Inhibitors

Additional pest resistance genes that can be optimized using the methods of the invention are those that encode protease inhibitors. Protease inhibitors can inhibit insect development (for review, see, e.g., Reeck et al. (1997) In Advances in Pest Control, supra., Chapter 10, pp. 157–183; Ryan (1990) Annu. Rev. Phytopathol. 28: 425–449) and often can kill insects and nematodes (see, Jongsma (1997) J. Insect Physiol. 43: 885–895). Protease inhibitors found in plant tissues are considered to be a part of plant defense mechanism against insect and nematode attack. A problem with the protease inhibitors for insect control is that insects can become resistant to the inhibitor (Jongsma and Bolter (1997) J. Insect. Physiol. 43, 885–895) described that insects change the composition of proteases in the digestive tract when an inhibitor is fed. It is very important to find/produce an inhibitor which inhibits a wide variety of insect proteases. In this example, we shall attempt to improve a plant cysteine inhibitor by DNA shuffling.

Protease inhibitor genes that are useful for shuffling include, those from all biological sources, including plants, animals, and microorganisms. Several nonhomologous families of protease inhibitors are known (Laskowski et al. (1980) Annu. Rev. Biochem. 49: 593–626), including at least ten families in plants (soybean trypsin inhibitor (Kunitz), Bowman-Birk inhibitor, potato inhibitor I, potato inhibitor II, squash inhibitor, Ragi 1–2/maize bifunctional inhibitor, carboxypeptidase A, B inhibitor, cysteine proteinase inhibitor (cystatins), aspartyl proteinase inhibitor, and barley trypsin inhibitor)(see, e.g., Ignacimuthu, In Biotechnological perspectives in chemical ecology of insects, T. Ananthakrishnan, ed., Science Publishers, Inc., pp. 277–283). Inhibitor families are known for each of the four mechanistic classes of proteolytic enzymes (serine, cysteine, aspartic, and metallo-proteases) (Ryan, supra.). Sequences of cysteine protease inhibitors are described in, for example, Reddy et al. (1975) J. Biol. Chem. 250: 1741–1750 and Abe etal. (1987) J. Biol. Chem. 262: 16793–16797. Serine protease inhibitors are described in, for example, U.S. Pat. No. 5,151,509.

Nucleic acids that encode α-amylase inhibitors, some of which are also bifunctional as protease inhibitors, are also suitable candidates for optimization using the DNA shuffling methods of the invention. Many of the α-amylase inhibitors exhibit amino acid similarity to four of the protease inhibitor families of plants (i.e., the Kunitz, Barley, Bowman-Birk and the Ragi/Maize bifunctional inhibitor families (see, e.g., Ryan et al., supra.). Sequences of Ragi α-amylase/protease inhibitors are described in, for example, Shivaraj et al. (1981) Biochem. J. 193: 29–36 and Svendsen et al. (1986) Carlsberg Res. Commun. 51: 43–50. See also, Schuler et al., supra.

Protease inhibitors of plant origin that have been engineered into other plant species are reviewed in, for example, Schuler et al. (1998) Tibtech 16: 168–175; Hilder et al. (1993) In Transgenic Plants, Vol. 1, Kung and Wu, Eds., Academic Press, pp. 317–338. Transgenic plants that carry a Manduca sexta protease inhibitor are described in U.S. Pat. No. 5,436,392. Nematode control using protease inhibitors is described in U.S. Pat. No. 5,494,813.

To identify recombinant genes that encode protease inhibitors having improved properties for use as pest resistance genes in plants, one can use assays such as those described herein. One suitable assay involves expressing the library of recombinant genes by phage display, after which panning is employed using a protease substrate. See, e.g., Jongsma et al. (1995) Molecular Breeding 1: 181–191.

C. Cholesterol Oxidase

Genes encoding polyphenol oxidases, including cholesterol oxidases, are another suitable substrate for use in the methods of the invention. Cholesterol oxidases are described in, for example, Shen et al. (1997) Arch. Insect Biochem. Physiol. 34: 429–442 and Purcell (1997) In Advances in Insect Control, Chapter 6, pp. 95–108, U.S. Pat. Nos. 5,665,560, and 5,602,017, and PCT application WO9425603, Genbank Accession Nos. 164550, E07692, E07691, E03850, E03828, E03827, U13981, and D00712.

D. Insecticidal Proteases

Additional targets for optimization using the DNA shuffling methods of the invention are genes that encode insecticidal proteases.

E. Vegetative Insecticidal Proteins

The DNA shuffling methods of the invention can also be applied to polynucleotides that encode vegetative insecticidal proteins (VIPs). VIPs are produced by some Bacillus species (including *thuringiensis* and *cereus*) during the vegetative growth phase. See, e.g., Warren (1 997) In *Advances in Insect Control*, supra., Chapter 7, pp. 109–121. The VIPs bear no similarity to the δ-endotoxins produced by *B. thuringiensis*.

VIPs that are effective against important corn pests, such as corn rootworm, include, for example, Vip1A(a) and Vip2A(a) (Warren, supra.). Vip3A is effective against a broad spectrum of lepidopteran insects (Estruch et al. (1996) *Proc. Nat'l. Acad Sci. USA* 93: 5389–5394; Yu et al. (1997) *Appl. Environ. Microbiol.* 63: 532–536).

F. Pathways for Insecticides

The invention also provides methods of applying DNA shuffling to obtain genes that encode pathways involved in the biosynthesis of natural products that have anti-pest activity. (1) Polyketides One approach that is particularly useful for shuffling of pathways such as those involved in biosynthesis of insecticides involves the use of restriction sites to recombine mutations. Polyketide clusters, e.g., spinosin, (Khosla et al., *TIBTECH* 14, September 1996) are typically 10 to 100 kb in length, specifying multiple large polypeptides which assemble into very large multienzyme complexes. Due to the modular nature of these complexes and the modular nature of the biosynthetic pathway, nucleic acids encoding protein modules can be exchanged between different polyketide clusters to generate novel and functional chimeric polyketides. The introduction of rare restriction endonuclease sites such as SfiI (eight base recognition, nonpalindromic overhangs) at nonessential sites between polypeptides or in introns engineered within polypeptides would provide "handles" with which to manipulate exchange of nucleic acid segments using the technique described above.

(2) Other Natural Products

Several examples are known of natural products that are potent insecticides. These products are elaborated by microorganisms, fungi or plants. There are several examples of natural plant and microbial products that are insecticidal. The genes involved in the biosynthesis of these products can be shuffled to increase the compound yield. The number of genes involved in the biosynthetic pathways specifying various natural products vary depending on the nature of the product. DNA shuffling can be applied to the entire set of genes coding for enzymes of a biochemical pathway for production of these natural products. As a result, many of these products can be produced at much higher concentrations either in a fermentor (for microorganisms) or inplanta. In other embodiments, the shuffled genes are selected for other improved properties, including, for example, increased toxicity and/or host range. These shuffled genes can be introduced in planta for in plant protection from insects.

G. Baculoviruses

Also suitable for use as substrates for DNA shuffling to generate recombinant nucleic acids which confer pest resistance are genes and genomes derived from insecticidal viruses, including baculoviruses. The use of baculoviruses as insecticides, as well as the identification of baculovirus genes that encode insecticidal proteins, is described in, for example, U.S. Pat. No. 5,662,897; see also, Miller, L. K. (1981) in *Genetic Engineering in the Plant Sciences*, Panopoulous (ed.), Praeger Publ., New York, pp. 203–224; Carstens, (1980) *Trends Biochem. Sci.* 52:107–110; Harrap and Payne (1979) in *Advances in Virus Research*, Vol. 25, Lawfer et al. (eds.), Academic Press, New York, pp. 273–355, *The Biology of Baculoviruses*, Vol. I and II, Granados and Federici (eds.), CRC Press, Boca Raton, Fla., 1986.).

The DNA shuffling and screening methods of the invention are useful for obtaining insecticidal viruses that have improved properties including, but not limited to, increased stability (including UV stability), greater infectivity and host range, greater virulence, and reduced time to kill a pest. The length of time between baculovirus ingestion and insect death can sometimes limit the efficacy of baculoviruses as pesticides, as the insect can continue to feed and damage crops during the time between application of the pesticide and insect death. By use of DNA shuffling and screening as described herein, one can obtain baculoviruses that are capable of killing the insects more quickly than naturally-occurring baculoviruses. Bioassays for determining the virulence and infectivity of baculoviruses are described in U.S. Pat. No. 5,662,897.

Baculoviruses are known to recombine in vivo. For example, Croizier et al. ((1980) *C. R. Acad. Sci. Paris Ser.* D290: 579–582) reported that AcNPV and *Galleria mellonella* virus recombined in Galleria larvae. More recently, Kondo and Maeda ((1 991) *J. Virol.* 65: 3625–3632) reported widening the host specificity of NPV by recombination in insect cells. DNA shuffling can expand and accelerate this process. For example, viral genome shuffling among several NPV species which have different host specificity can be used to increase the host spectrum. This is accomplished by obtaining NPV's such as *Autographa californica, Spodoptera frugiperda* and *Heliothis virescens* are obtained and isolating DNA from the viruses. These DNA samples are mixed and shuffled. Sf9 cells are transfected with shuffled and reassembled DNA, and the recombinant virus is isolated. Isolated virus samples are then tested for infectivity against insect species such as, for example, *Trichoplusia ni, Heliothis virescens* and *Spodoptera exigua*. A sublethal dose, which is determined with the wild-type virus against its original or related host (e.g., AcNPV vs *T ni*, SfNPV vs *S. exigua*), is used.

The insecticidal viruses that are obtained using the methods of the invention are useful for application to plants. Formulations and application methods are known to those of skill in the art. See, e.g., Couch and Ignoffo (1981) in *Microbial Control of pests and Plant Disease* 1970–1980, Burges (ed.), chapter 34, pp. 621–634; Corke and Rishbeth, Id., chapter 39, pp. 717–732; Brockwell (1980) in *Methods for Evaluating Nitrogen Fixation*, Bergersen (ed.) pp. 417–488; Burton (1982) in *Biological Nitrogen Fixation Technology for Tropical Agriculture*, Graham and Harris (eds.) pp. 105–114; and Roughley (1982) Id., pp. 115–127.

IV. Improved Properties of Pest Resistance Genes and Screening Methods

The libraries of recombinant pest resistance genes that are produced using the DNA shuffling methods described herein are screened to identify those that exhibit improved properties for use in protecting plants against pests. Included among properties for which the methods of the invention are useful for obtaining improved pest resistance genes are the following. By choice of an appropriate screening strategy, one can simultaneously or sequentially obtain genes that are optimized for more than one property. For example, by performing shuffling using as one substrate genes that encode highly potent toxins, and as another substrate genes that are not easily overcome by the development of resistance to the gene product by the target, one can obtain an optimized gene that combines the two properties of being highly potent and not susceptible to the development of target resistance.

The invention thus provides the shuffled polynucleotide sequence(s) that confer insect resistance on an agricultural organism, and the modified agricultural organisms themselves, produced by the method of polynucleotide sequence shuffling. The exact structures of said produced polynucleotide sequences and modified agricultural organisms are definable most readily by reference to the method by which they are generated. Thus, the invention includes a shuffled polynucleotide sequence conferring the desired phenotype, or a plurality thereof, produced by the methods described herein. The shuffled polynucleotides(s) produced thereby are easily distinguishable from naturally occurring genome sequences by virtue of their atypical modified or novel phenotype(s) which is/are normally not present in the population of naturally occurring agricultural organism. The shuffled polynucleotide sequence can be further distinguished from naturally-occurring plant, animal, or microbe genome sequences by reference to sequence databases and published sequence data, wherein the shuffled polynucleotide will generally comprise a constellation of mutations as compared to the reference data set which would be recognized by the skilled artisan as a polynucleotide sequence which is substantially improbable of having evolved by natural evolution or classical breeding.

A. Increased Potency against Target Pests

The methods of the invention are useful for obtaining pest resistance genes that exhibit increased potency against target pests. The shuffled insect resistance genes prepared as described above are screened for high insecticidal activity. Such genes can be identified by, for example, expressing members of a library of shuffled genes to identify those that encode a polypeptide that has an increased $EC_{50}$ (concentration resulting in 50% reduction in insect growth) and/or $LC_{50}$ (concentration resulting in 50% insect mortality).

In some embodiments, the invention involves shuffling a gene that encodes a toxin having a desired specificity, but relatively low cytotoxicity, with another toxin gene that has high cytotoxicity. An illustrative example is *Bacillus popilliae*, which is pathogenic to scarab beetles such as the Japanese beetle and produces an insecticidal protein known as Cry18Aa (Zhang et al. (1997) *J. Bact.* 179: 4336–4341). The insecticidal activity of this protein, however, is not sufficiently high for use to protect plants from beetle infestation. To improve the cytotoxicity of Cry18Aa, the gene that encodes this toxin is cloned and shuffled with one or more of its homologous genes from another Bacillus species. For example, one can shuffle the gene that encodes cry18Aa with the *B. thuringiensis* gene that encodes Cry2. Other genes that are homologous to cry18Aa can also be cloned and shuffled with cry18Aa. For example, one can screen a genomic library of several *B. thuringiensis* and *B. popilliae* strains using the cloned cry18Aa gene as a hybridization probe.

Once the shuffling is completed, the resulting library of shuffled toxin genes is screened to identify those that exhibit enhanced insecticidal activity. One way of performing this screening is to clone the protein coding region of the shuffled genes (for example, after PCR amplification) into an expression vector that is suitable for expressing the genes in a chosen host cell such as, for example, *E. coli*. In presently preferred embodiments, the vector includes coding sequences that, when linked in frame to the coding sequence of the shuffled gene, encode an easily detectable and/or immobilizable tag (e.g., multiple His residues). The vectors can be introduced into *E. coli*, as well as into other host cells such as a cry strain of *B. thuringiensis*. If desired, transformants can be subjected to a preliminary screen (e.g., by immunoassay) to identify those that produce the insecticidal protein. Those that are positive in the preliminary screen are then tested in a functional screen to identify shuffled genes that encode a toxin having the desired increase in activity.

A whole pest assay, which is often called an in vivo assay, can be used for determining toxicity. In these assays, the toxin polypeptides expressed from the shuffled genes are placed on pest diet and allowed to be consumed by the target pest. Preferably, the shuffled polypeptides are at least partially purified prior to the screening. For example, when *E. coli* is used as the host cell for expression of the shuffled polypeptides, the polypeptides are often produced as inclusion bodies. The inclusion bodies can be liberated using methods known to those of skill in the art. For example, the *E. coli* cells can be dissociated using a detergent such as B-PER Bacterial Protein Extraction Reagent (Pierce) according to the manufacturer's instructions. The detergent can be removed, e.g., by filtration, and the inclusion body dissolved in, for example, 0.02N NaOH. The pH of the solution is then neutralized, e.g., by addition of 100 mM Tris-HCl, pH 8. In presently preferred embodiments, the insecticidal protein encoded by the shuffled gene is purified. Conveniently, this can be accomplished using a 96- or more well filter plate that contains an affinity reagent (such as Ni-NTA agarose (Qiagen) for a polypeptide that has a histidine tag). Preferably, a sufficient number of host cells is subjected to extraction to ensure that the amount of polypeptide passed through the filter exceeds the capacity of the affinity reagent, regardless of the expression level of the particular polypeptide. Upon dissociation from the affinity reagent, each sample will then contain a roughly equal amount of protein.

The amount of polypeptide used in each whole pest test is a sublethal dose, as determined using the wild-type polypeptide encoded by the toxin gene used for the shuffling. Mortality of the pest is observed to assess the activity level of each polypeptide sample. To increase the efficiency of the screening assay, samples can be pooled and tested for activity. Pooled samples that show some pest mortality are separated into the individual pool components to identify those samples that are responsible for the mortality. Positive samples are selected for use, or for a second round of shuffling.

In preferred embodiments, however, the assays for detecting cell death or cell growth are conducted in a format that is more amenable to high-throughput screening. For example, an in vitro assay can be used. Such assays typically involve the use of cultured insect cells that are susceptible to the particular toxin being screened, and/or cells that express a receptor for the particular toxin, either naturally or as a result of expression of a heterologous gene. Thus, in addition to insect cells, mammalian (e.g., CHO cells), bacterial, and yeast cells are among those that are useful in the in vitro assays. In vitro bioassays which measure toxicity against cultured insect cells are described in, for example, Johnson (1994) *J. Invertebr. Pathol.* 63: 123–9. In a typical format, a plate having 96 or more wells is used. Toxins expressed by the library of shuffled genes are added to the wells and the effect on cell viability and/or proliferation is determined.

One such assay involves detection of the release of ATPase by cells that are killed by optimized toxins obtained using DNA shuffling. The level of ATPase that was released by the toxin can be measured at a very high sensitivity level with, for example, a luciferase assay.

Another assay involves detection of changes in cell morphology due to water uptake. When insect cells are intoxicated with Bt Cry protein, for example, the cell morphology changes substantially due to water intake. Since the Cry protein makes the cell highly permeable, the cells take up a large amount of water when left in a low osmotic solution. This morphological change can be detected by light scattering.

Dyes and labels that are useful for detecting cell death or cell growth are known to those of skill in the art. In these assays, cells are contacted with the toxin in, for example, a well of a microtiter plate, after which the cells are washed and the uptake or retention of the dye or label is measured using a plate reader or plate scintillation counter. Suitable dyes include, but are not limited to:

Alamar blue: The alamar blue assay incorporates a fluorometric/colorimetric growth indicator based on detection of metabolic activity. The system incorporates an oxidation-reduction (Redox) indicator that both fluoresces and changes color in response to chemical reduction of growth medium resulting from cell growth. An aliquot (e.g., 20 µl) of Alamar blue is added into each well in the last 8 hr of culture. The plate then is measured by absorbance (O.D. 570/600) or by fluorescence.

$^3$H-thymidine Incorporation: The protocol uses as its end-point the determination of cell proliferation by measuring the incorporation of $^3$H-thymidine into cellular DNA. An aliquot (e.g., 1 µCi) of radioactive label is added during the last 4 to 24 hr of the culture. A semiautomated cell harvesting apparatus can then be used to lyse the cells with water and precipitate the labeled DNA on glass fiber filters. The filter pads can then be dried and counted by standard liquid scintillation counting techniques.

Neutral red: Neutral red is a cationic azine dye used to stain cytoplasmic granules of cells. For example, at the end of the culture, an aliquot (e.g., 100 µl of 1: 500 dilution of 0.5% (w/v) neutral red (Sigma Chemical, St. Louis Mo.)) is added into each well. The cells are then incubated in 5% $CO_2$ at 37° C. for 2–4 hrs. The color is subtracted by 50% methanol (with 1% acetic acid), and absorbance is measured at 540 wavelength.

Trypan blue test of cell viability: The dye exclusion test is used to determine the number of viable cells present in a cell suspension. It is based on the principle that live cells possess intact cell membranes that exclude certain dye, whereas dead cells do not. In this test, a cell suspension is simply mixed with dye and then visually examined to determine whether cells take up or exclude dye. A viable cell will have a clear cytoplasm whereas a nonviable cell will have a blue cytoplasm. This assay can be carried out by, for example, centrifuging an aliquot of cell suspension for 5 min at 100 × g and discarding the supernatant. The cell pellet is resuspended in 1 ml PBS or serum-free medium. One part of 0.4% trypan blue is mixed with one part cell suspension (dilution of cells). The mixture is allowed to incubate about 3 min at room temperature. A drop of the trypan blue/cell mixture is then applied to a hemocytometer and observed under a binocular microscope.

One example of a suitable in vitro assay using cultured insect cells is for the Bt Cry1C protein. Sf9 (*Spodoptera frugiperda*) cells are used because this cell line is sensitive to Cry1C protein. Other insect cell lines, such as Heliothis and Trichoplusia spp. could also be used for Cry1C. Sf9 is not highly sensitive to Cry1A proteins. In the case of Cry1A and related proteins such as Cry1F and Cry1G, CF1 (*Choristonenra fumiferana*) cells can be used. CF1 cells are highly sensitive to Cry1A -type proteins. When the activated Cry1C protein was mixed with Sf9 cells, the Cry protein made the cell membrane highly permeable to small molecules such as water. When a dye such as trypan blue was added to the cell suspension, those cells which was killed by the Cry protein was stained with the dye. Thus, the insecticidal activity level was determined by image analysis.

Additional in vitro assays involve the use of receptors for the particular toxins. The target sites in insects for several insecticidal proteins, including the Bt Cry proteins, are midgut epithelial cells. The toxin protein finds a receptor on the cells and forms a specific receptor-Cry protein complex. After binding the receptor, the Cry protein goes into the cell membrane and forms a pore to make the cell membrane highly permeable. The cells thus lose the osmotic pressure regulation and are eventually killed. It appears that the receptor binding step, or affinity of the Cry protein to its receptor, is critical for the insecticidal activity level. High affinity of a Cry mutant to the receptor means high insecticidal activity. Thus, shuffled genes that encode toxins that exhibit enhanced potency against a pest can also be identified on the basis of affinity for a specific receptor for the toxin.

In one example of this type of screening assay, brush border membrane vesicles (BBMV; see, e.g., Lee et al. (1995) *Appl. Environ. Microbiol.* 61: 3836–42) are used. BBMV, which contain the receptor at a high concentration level, are isolated from insects, either from isolated midgut tissue or whole insect body. One advantage of using BBMV is that they can be prepared from almost any insects of interest. BBMV are typically prepared by simply homogenizing whole insects and repeating differential centrifugations, e.g., between 3000 and 12000 rpm. Since the BBMV fraction is heavier than other fractions, it can be easily isolated by centrifugation. In one embodiment of this type of screening method, radioactive shuffled toxin proteins are prepared by iodination. The radioactive proteins are then mixed with BBMV in 96-well plates and allowed to bind. The BBMV are washed by filtration to remove free (unbound proteins). Two sets of plates are prepared with identical sample sets. One set of plates is incubated for ten minutes and the other for two hours before 100× unlabeled wild-type protein is added. The short reaction time is to determine the extent of reversible receptor binding (i.e., measuring the receptor binding) and the long incubation time is to determine membrane insertion, which is not reversible. Thus, by using two different incubation periods, one can determine the mode of action of the protein. When the shuffled proteins are not highly active, the excess cold wild-type protein repels the shuffled proteins from binding on BBMV. BBMV are then filtered to remove the supernate, after which the amount of label present is measured. This allows determination of the amount of shuffled protein that is left on BBMV.

A competitive binding assay is one suitable format for identifying shuffled genes that encode toxins having increased affinity for a receptor. For example, a labeled (e.g., radioisotope labeled), non-mutated (wild-type) toxin protein is allowed to bind to am immobilized receptor (e.g., BBMV-bound receptors). After the excess (unbound) protein is washed away, a cold (unlabeled) toxin protein isolated from the DNA-shuffled mutant pool as described above is used to compete for binding with the non-mutated toxin proteins.

When the receptor affinity of a mutated toxin protein is higher than the non-mutated protein, the mutant replaces the receptor bound non-mutated protein. Therefore, the amount of label associated with the receptors is reduced. By measuring the amount of label associated with filtered BBMV, for example, the mutants which have the higher affinity to the receptor are identified. Those mutants with high receptor affinity can be confirmed as to elevated insecticidal activity by whole insect assay or cell assay as described above.

The receptor binding assay described above can be applied to insect cells. Keeton and Bulla ((1997) *Appl Environ. Microbiol.* 63: 3419–3425) demonstrated that a mammalian cell line expressing a "Bt toxin receptor" was sensitive to a class of Cry protein called Cry1A. The "receptor" gene used by Keeton and Bulla was said to be similar to cadherin and has a very limited application, because only a selected few Cry proteins are known to bind this receptor. Other receptors for Bt Cry proteins have been identified. Most of them were reported to be aminopeptidase N. However, aminopeptidase N has also a limited use due to its narrow specificity to the Cry proteins. For example, Cry1C does not recognize this receptor protein. However, by cloning a receptor gene specific to a Cry protein, which is being studied by DNA shuffling, into a cell line, a specific binding assay protocol can be developed. Receptors for many Bt toxins have been characterized (Cry1A toxin receptor from the tobacco hornworm *Manduca sexta* (Keeton et al. (1997) *Appl. Environ. Microbiol.* 63: 3419–25; Knight et al. (1994) *Mol. Microbiol.* 11: 429–36; Knight et al. (1995) *J. Biol Chem.* 270: 17765–70; Masson et al. (1995) *J. Biol. Chem.* 270: 20309–15; Vadlamudi et al. (1995) *J. Biol. Chem.* 270: 5490–4), gypsy moth (*Lymantria dispar*) (Rajamohan et al. (1996) *Proc. Nat'l Acad Sci. USA* 93:25, 1433843), *Heliothis virescens* (Luo et al. (1997) *Insect Biochem. Mol. Biol.* 27: 35–43 and Gill et al. (1995) *J. Biot Chem.* 270: 27277–82). For Bt toxins, biotinylated proteins can also be used in binding assays (Du et al. (1996) *Appl. Environ. Microbiol.* 62: 2932–9). Bt Cry proteins, when activated, can form a pore on liposomes which are made of phospholipids and a dye or radioactive isotope. The pore formation due to Cry proteins can be determined by monitoring leaked dye or radioisotope.

In other embodiments, screening is performed by expressing the recombinant pest resistance genes as fusion proteins that are displayed on the surface of, for example, a phage or other replicable genetic package. The use of phage-display technology to produce and screen libraries of polypeptides for binding to a selected target has been described. See, e.g., Cwirla et al. (1990) *Proc. Nat'l. Acad Sci. USA* 87: 6378–6382; Devlin et al. (1990) *Science* 249: 404–406; Scott & Smith (1990) *Science* 249: 386–388; Ladner et al., U.S. Pat. No. 5,571,698. Libraries of recombinant pest resistance genes can also be displayed from replicable genetic packages other than phage, such as eukaryotic viruses and bacteria. Phage display of a Bt CryIA(a) insecticidal toxin is discussed in Marzari et al. (1997) *FEBS Lett.* 411: 27–31. The phage display libraries can be screened by, for example, identifying those phage that display a recombinant polypeptide that has an enhanced affinity for an insect midgut, or for a receptor polypeptide that binds the toxin.

In an alternative embodiment, the phage display library is subjected to consumption by the target insects. DNA that encodes the recombinant pest resistance gene is then amplified from individual insects which die as a result of consuming the phage. For example, polymerase chain reaction can be employed using as primers two oligonucleotides that hybridize to an expression vector at positions which flank the inserted recombinant pest resistance gene.

Another screening method involves the use of transgenic "hairy roots" that are generated by *Agrobacterium rhizogenes*. This bacterium causes hairy root disease in many plants by transferring a portion of DNA from its Ri (root inducing) plasmid to infected plant cells (Zambryski et al. (1989) *Cell* 56:193–201). Genes present in the transferred DNA (T-DNA) alter the hormone balance in the plant cells causing them to produce roots. Unlike normal plant roots, the hairy roots are readily cultured indefinitely on simple medium such as Murashige and Skoog (MS: (1962) *Physiol. Plant.* 15: 473–497). Hairy roots can also be induced to regenerate into whole plants (Tepfer (1984) *Cell* 37: 959–967). There are no size requirements imposed on the T-DNA, which allows one to insert any gene of interest and have it transferred to the plant cells. This system allows one to rapidly produce hundreds or thousands of transgenic roots that express genes that have been created via in vitro shuffling. Root tissue is particularly useful for screening nematode resistance and rootworm resistance.

A schematic diagram of this screening process is shown in FIG. 4. A library of shuffled toxin genes is created as described above and ligated into a plasmid that contains an antibiotic resistance gene (e.g., for kanamycin), an *E. coli* origin of replication (for maintenance), and a region of the Ri T-DNA (Tepfer and Casse-Delbart (1987) *Microbiol. Sci.* 4: 24–28). The plasmid library can be introduced into *A. rhizogenes* cells by electroporation (Main et al. (1995) *Methods Mol. Biol.* 44:405–412) and the cells are plated on a suitable medium (e.g., MYA medium (8.0 g/L mannitol, 5.0 g/L yeast extract, 2.0 g/L ammonium sulphate, 0.5 g/L casamino acids and 5.0 g/L sodium chloride, pH 6.6) containing 25–200 µg/ml kanamycin or other selection reagent) and incubated at approximately 28° C. for several days. Only cells in which the plasmid has integrated into the endogenous Ri plasmid by homologous recombination in the T-DNA region survive selection because the plasmid can not freely replicate in *A. rhizogenes*. All of the colonies are washed from the plates and pooled for use as inocula on the plant tissues.

Plant tissues are then inoculated with the colonies. Many different dicot and monocot species, including Soybean (*Glycine max*), can be induced to form hairy roots by *A. rhizogenes* (De Cleene and De Ley (1981) *Bot. Rev.* 47:147–94). The plant tissues (e.g., seedlings) are typically surface-sterilized, after which hypocotyl segments are cut and inserted apical end down in solid MS medium in 24- or 48-well plates. A drop of the *A. rhizogenes* inoculum is applied to the end of the tissue section and the plates are incubated at 26–28° C. in the dark until roots appear (1–4 weeks). Untransformed plant cells will not produce roots on MS medium. Thus, roots that form are assumed to be transformed and need not be subjected to antibiotic selection. Preferably, however, the *A. rhizogenes* is killed by removing the roots from the petioles and culturing them on MS medium supplemented with 500 µg/ml carbenicillin or cefotaxime. Cultured hairy roots grow rapidly and can be subdivided several times to provide replicates for screening experiments.

Independently transformed root lines are infected with nematodes and assayed for cysts and nematode death, or they are provided to second or third instar larvae and screened for insecticidal activity (larval death). The best root lines that survive nematode or insect attack are chosen and the toxin genes are reisolated, e.g., by PCR with primers matching the plasmid sequence surrounding the cloning site at which the shuffled genes were inserted. In preferred embodiments, these genes are mixed, DNase treated, reassembled and shuffled. A second round of introduction into *A. rhizogenes* and infection of plant tissue is carried out. These cycles can be repeated until the desired level of pest resistance is acquired. The final evolved toxin gene is isolated and used to transform the desired plant cultivar in a manner conducive to regenerating fertile commercially viable plants.

The system is also useful for identifying genes that encode previously unknown toxins, or toxins for which the genes were not previously available. When the goal of the first round of screening is to identify a previously unknown toxin gene, a genomic library from the source organism can be made in the Ri plasmid. To facilitate cloning, linkers that contain an infrequently cleaved restriction site (e.g., NotI) are added to genomic fragments and cloned into the *E. coli* vector for delivery into *A. rhizogenes*. The remainder of the assay is as described except that the initial recovery of genes from surviving roots is followed by gene characterization and shuffling of all or part of the genomic sequences.

Insect pathogens from which it is desirable to obtain toxin genes include, for example, microbes such as *Bacillus thuringiensis\** (various insects), *Bacillus sphaericus\** (mosquito), *Bacillus popilliae\** (beetle), *Bacillus lentimorbus* (beetle), *Bacillus larvae* (bee), *Bacillus moritai* (house fly), *Clostridium brevifaciens\** (caterpillar), *Clostridium malacosomae\** (caterpillar), *Pseudomonas aeruginosa* (various insects incl. grasshopper), *Enterobactor cloacae* (locust), *Enterobactor aerogenes, Serratia marcescens* (various insects), *Serratia entomophila* (beetle), *Serratia liquefaciens* (various insects), *Proteus vulgaris* (grasshopper), *Xenorhabdus nematophilus\** (beetle), *Streptococcus faecalis* (various insects), *Rickettsiella popilliae\** (beetle), *Rickettsiella melolonthae\** (beetles, caterpillar), and Mycoplasma/Spiroplasma (* indicates pathogens presently known to produce insecticidal proteins others may produce the toxin).

Viral pathogens include, for example, Baculovirus (including Nuclear polyhedrosis virus, Granulosis virus, and Nonoccluded virus), Polydnavirus (including Ichnovirus and Bracovirus), Poxvirus, Ascovirus, Iridovirus, Nodavirus, PicoRNAvirus, Tetravirus, Reovirus (including Cytoplasmic polyhedrosis virus and Muscareovirus), Birnavirus, Rhabdovirus, Togavirus, Flavivirus, and Bunyavirus.

Fungal insect pathogens include, for example, Cordyceps spp., Strongwellsea spp., *Zoophthora anuiensis, Beauveria bassiana, Beauveria brongniartii, Paecilomyces fumosoroseus, Verticillium lecanii, Metarhizium flavoviride, Metarhizium anisopliae, Lagenidium gigantum, Nomuraea rileyi, Nomuraea cylindrosporae, Pandora neoaphidis, Pandora delphacis, Neozygitesfloridana, Hirsutella thompsonii, Nilaparvata lugens, Erynia neoaphidis,* and Massospora spp.

Nematodes that are pathogenic to insects include, for example, *Tetradonema plicans* (fly), *Mermis nigrescens* (grasshopper), *Romanomermis culicivorax* (mosquito), *Agramermis decaudata* (grasshopper), *Rhabditis insectivora* (beetle), Steinernema spp. (beetle, caterpillar) (symbiotic bacteria of these nematodes (e.g., *Xenorhabdus/ Photorhabdus* spp.) produce toxins, *Steinernema carpocapsae, Steinernema glaseri, Steinernema kusidai, Eudiplogaster aphodii* (beetle), *Deladenus siricidicola* (isp), Contortylenchus spp. (beetle), *Heterotylenchus autumnalis* (fly), and *Sphaerularia bombi* (bee).

Other applications of root lines transformed with shuffled libraries include uptake and utilization of solutes, nutrients, or chemicals (Tepfer et al. (1989) *Plant Mol. Biol.* 13: 295–302). Also fungal infections, Rhizobium nodule formation, and secondary metabolite formation can be screened using hairy roots (Tepfer and Casse-Delbart (1987) *MicrobioL Sci.* 4:24–28; Saito et al. (1 992) *J. Nat. Prod.* 55: 149–162).

There are several possible variations in the transgenic plant tissue screening method described here. First, *A. tumefaciens,* which is more widely used than *A. rhizogenes,* can deliver the shuffled gene library. Disarmed, binary versions of both strains (Walkerpeach and Velton (1994) *Plant Molecular Biology Manual,* B1:1–19) allow genes to be transferred with antibiotic markers in the absence of native T-DNA disease-causing genes to select for transformed cells that can be induced to form callus, roots, shoots or whole plants depending on the tissue type that the pest in question will attack. For cereal and grain producing plant species, other plant transformation methods such as particle gun bombardment (Barcelo and Lazzari (1995) *Methods Mol. Biol.* 49:113–123) can be used to create transgenic tissues for screening.

B. Increased Target Range

The invention also provides methods of using DNA shuffling to obtain pest resistance genes that are effective against a broader range of insects, nematodes, or other pests than a naturally occurring gene. For example, one can apply DNA shuffling to families of genes that code for toxins having different target specificities and screen for those that exhibit toxicity against a desired target pest against which a toxin encoded by a naturally occurring gene was less effective. Specific examples of genes that one can shuffle to obtain enhanced target range include, but are not limited to:

(i) Bt toxin genes can be shuffled to obtain higher activity vs. corn root worm and other coleopteran pests.

(ii) Bt toxin genes can also be shuffled to enhance activity vs. other specific pests belonging to different order like lepidoptera and diptera.

(iii) Bt toxin family of genes can also be shuffled to obtain new activity vs. insect pests that have developed resistance (*Nature Biotech,* September 1997—p. 816) to existing toxins.

(iv) Other genes coding for toxins such as cholesterol oxidase, protease inhibitors, lectins, etc. (*Asgrow Reports— Genetic Engineering for Pest Control,* Len Copping, Chapters 2.1–2.4), can be shuffled to enhance the potency as well as spectrum.

Screening to identify members of libraries of shuffled genes that encode toxins having increased toxin range include both in vivo and in vitro assay formats as described above. Again, in vitro assays are generally preferred because of their greater amenability to high throughput screening. Assays for insecticidal spectrum using larval insect midgut (see, e.g., Van Rie et al. (1989) *Eur. J. Biochem.* 186: 239–47). Receptors for the toxins, either expressed in cell lines, or as BBMV, can be used as described above.

Generally, cells or receptors that are not susceptible to, or do not strongly bind, a naturally occurring toxin of interest, are chosen for use in the assays. The library of recombinant toxins are tested to identify those that are active against the target cells, and/or that exhibit a high affinity for the target receptor.

C. Decreased Susceptibility to Development of Resistance by Pests

One problem that is often observed when using biopesticides is the target pest's development of resistance to the pesticide due to selective pressure on the pest populations (see, e.g., Kumar et al., supra.). The present invention provides methods of obtaining recombinant pest resistance genes that are less susceptible than naturally occurring genes to the development of resistance.

Selection for optimized recombinant insect resistance genes that are less susceptible to the pest becoming resistant can involve, for example, feeding diverse (e.g., members of a library of shuffled genes) to a breeding population of insects and determining for each clone how quickly resistance occurs. An alternative approach is to use 2 or more Bt toxins, preferably diverse Bt toxins so that resistance to both would be difficult to obtain. Different combinations of genes can be assayed as described above to determine the ease of development of resistance to both genes.

One example of a scheme for obtaining a Bt toxin that is less susceptible to the development of resistance is as follows. Diamondback moths easily develop resistance against Cry1A, a potent and widely used Bt toxin. These resistant moths are still sensitive to Cry1C because Cry1C binds to a receptor different from that for Cry1A's, but Cry1C is much less potent than Cry1A. One can use DNA shuffling as described herein to increase the potency of Cry1C so that it is more effective against the resistant insects. These screening tests can be done in *Spodotera frugiperda* Sf9 insect cells, since Sf9 cells are sensitive to Cry1C but not to Cry1A. The assays can be performed either on unmodified Sf9 cells or on other insect cell lines (such as Heliothis sp., *Trichoplusia ni* or Diabrotica sp. (corn rootworm)) which are transfected with the gene for the Cry1C receptor (see, e.g., de Maagd et al. (1996) *Appl. Environ. Microbiol.* 62: 2753–7).

D. Increased Expression Level

In another embodiment, the invention provides methods of increasing the expression levels of pest resistance genes. This can be accomplished through optimization of the genes themselves, for example, by altering the CG content of the genes to more closely match that of plants, or improving codon usage through use of the DNA shuffling methods of the invention.

Alternatively, increased expression can be achieved by using DNA shuffling to obtain improved promoters and other gene expression control signals. Usually, a pest resistance gene is operably linked to an additional sequence, such as a regulatory sequence, to ensure its expression. These regulatory sequences can include one or more of the following: an enhancer, a promoter, a signal peptide sequence, an intron and/or a polyadenylation sequence. The efficacy of a pest resistance gene often depends on the level of expression of an gene product by the plant or other host. An optimized promoter and/or other control sequence is likely to result in improved pest resistance. Moreover, it is sometimes desirable to have control over the type of cell in which a gene is expressed, and/or the timing of pest resistance gene expression. For example, the development of resistance to a pest resistance gene can be delayed or eliminated by using a promoter that is inducible or otherwise capable of directing expression of the resistance gene noncontinuously. The methods of the invention provide for optimization of these and other factors which are influenced by promoters and other control sequences.

Expression can effectively be improved by a variety of means, including increasing the rate of production of an expression product, decreasing the rate of degradation of the expression product or improving the capacity of the expression product to perform its intended function. The methods involve subjecting to DNA shuffling polynucleotides which are involved in control of gene expression. At least first and second forms of a nucleic acid that comprises a control sequence, which forms differ from each other in two or more nucleotides, are recombined as described above. The resulting library of recombinant control sequences are screened to identify at least one optimized recombinant control sequence that exhibits enhanced strength, inducibility, or specificity.

The substrates for recombination can be the full-length vectors, or fragments thereof, which include a coding sequence and/or regulatory sequences to which the coding sequence is operably linked. The substrates can include variants of any of the regulatory and/or coding sequence(s) present in the vector. If recombination is effected at the level of fragments, the recombinant segments should be reinserted into vectors before screening. If recombination proceeds in vitro, vectors containing the recombinant segments are usually introduced into cells before screening.

Cells containing the recombinant segments can be screened by detecting expression of the gene encoded by a selection marker. For purposes of selection and/or screening, a gene product expressed from a vector is sometimes an easily detected marker rather than a product having an actual therapeutic purpose, e.g., a green fluorescent protein (see, Crameri (1996) *Nature Biotechnol.* 14: 315–319) or a cell surface protein. For example, if this marker is green fluorescent protein, cells with the highest expression levels can be identified by flow cytometry-based cell sorting. If the marker is a cell surface protein, the cells are stained with a reagent having affinity for the protein, such as antibody, and again analyzed by flow cytometry-based cell sorting. Drug resistance genes can also provide a selectable marker. Alternatively, the gene product can be a fusion protein comprising any combination of detection and selection markers. Internal reference marker genes can be included on the vector to detect and compensate for variations in copy number or insertion site.

Recombinant segments from the cells showing highest expression of the marker gene can be used as some or all of the substrates in a further round of recombination and screening, if additional improvement is desired. The optimized control regions can then be used for the expression of pest resistance genes in transgenic plants, or in microorganisms that are applied to plants of interest, including microorganisms that can colonize the plants.

E. Increased Resistance to Protease Degradation

Insect midgut fluids contain proteases, so resistance to protease degradation is a desirable property of pest resistance gene products. The present invention provides methods of obtaining recombinant pest resistance genes that encode polypeptides that exhibit increased resistance to proteases. Typically, a library of recombinant genes is screened by expressing the gene products and testing to identify those that regain their integrity and pesticidal activity when placed in the presence of a protease. For example, pools of shuffled genes can be expressed, and the gene products incubated in the presence of insect midgut fluids or other media that contain relevant proteases. The integrity of the polypeptides can be determined by, for example, gel electrophoresis or by an appropriate bioassay. Those pools that contain protease-resistant gene products can be subdivided and retested to identify those library members that encode protease-resistant gene products.

F. Increased Stability in Environmental Conditions

Another property for which improvement is desirable is the ability of pest resistance gene products to withstand extremes of pH and other conditions that are prevalent at the sites of action in target pests. Midgut fluids of Coleoptera and Hemiptera, for example, are often at a relatively low pH (about pH 3–6), while those of most other insect guts are at a relatively high pH (about pH 8–11). Inactivation by exposure to ultraviolet light is a major problem that can limit the use of insect-pathogenic virus formulations, for example, as sprayable insecticides. After the insecticides are sprayed onto crops to protect them from insect damage, the virus is quickly inactivated by sunlight, particularly UV light.

Screening for these optimized shuffled genes can be performed in a similar manner to testing for protease resistance as described above. For example, pest resistance gene products are placed under conditions that are found at the site of action. Those library members that encode gene products having increased stability under the test conditions are identified.

To enhance the probability of obtaining genes that encode polypeptides having reduced UV light sensitivity, one can include in the shuffling reaction oligonucleotides that include codons for amino acids that are not highly sensitive to UV light. One suitable method to screen for UV resistant pathogenic virus formulations is as follows. In the case of *Autographa californica* nuclear polyhedrosis virus (AcNPV), the entire viral genome is shuffled. First, AcNPV is exposed to a dose of UV, which is set at a level for only 5% of virus survival. The virus that survive the UV treatment are plaque purified on Sf9 (*Spodoptera frugiperda*) cells, propagated in *Trichoplusia ni* (cabbage looper) and subjected to the second UV treatment. This process is repeated several times. The viral genome is isolated from the surviving population pool after several passages under UV. The UV-resistant viral DNA is mixed with DNA from wild-type virus and shuffled. Sf9 cells are transfected with reassembled DNA, and virus is isolated. After this UV-selection cycle, a several virus clones, which are UV resistant and show no other obvious changes in the phenotypes such as infectivity and speed of kill, are obtained.

G. Reduced Toxicity to a Host Plant

Shuffled genes that are prepared using the DNA shuffling methods of the invention can also be screened to identify those that exhibit reduced toxicity to a host plant compared to a naturally occurring gene. The genes can be introduced into plants or plant cells to identify those that are relatively nontoxic, or the gene products can be assayed for toxicity against plants or plant cells.

V. USES OF OPTIMIZED PEST RESISTANCE GENES

The optimized pest resistance genes produced using the methods of the invention find uses both in vitro and in vivo. For example, the genes having improved anti-pest activities can be used in vitro to study the mechanisms by which plants can be protected against pests, and for production of pesticides that can be applied to plants. The optimized pest resistance genes can be introduced into microorganisms that colonize plant surfaces, or can be introduced into plants themselves. In each case, expression of the pest resistance gene is capable of conferring upon the plant resistance to the pest.

A. Production of Pesticides

The optimized pest resistance genes can be used for the recombinant production of polypeptides that are useful as pesticides. Typically, an optimized gene is introduced into an expression cassette for high level expression in a desired host cell. A typical expression cassette contains a promoter operably linked to the desired DNA sequence. More than one optimized pest resistance gene can be expressed in a single prokaryotic cell by placing multiple transcriptional cassettes in a single expression vector, by constructing a gene that encodes a fusion protein consisting of more than one pest resistance gene, or by utilizing different selectable markers for each of the expression vectors which are employed in the cloning strategy.

Optimized pest resistance genes of the invention can be expressed in a variety of host cells, including *E. coli*, other bacterial hosts, yeast, and various higher eukaryotic cells such as the COS, CHO and HeLa cells lines and myeloma cell lines. Examples of useful bacteria include, but are not limited to, Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. The recombinant gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

In a preferred embodiment, the expression cassettes are useful for expression of pest resistance genes in prokaryotic host cells. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Either constitutive or regulated promoters can be used in the present invention. Regulated promoters can be advantageous because the host cells can be grown to high densities before expression of the pest resistance polypeptides is induced. High level expression of heterologous proteins slows cell growth in some situations. Regulated promoters especially suitable for use in *E. coli* include the bacteriophage lambda $P_L$ promoter, the hybrid trp-lac promoter (Amann et al., Gene (1983) 25: 167; de Boer et al., *Proc. Natl. Acad. Sci. USA* (1983) 80: 21, and the bacteriophage T7 promoter (Studier et al., *J. Mol. Biol.* (1986); Tabor et al., (1985). These promoters and their use are discussed in Sambrook et al., supra.

For expression of pest resistance polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*. Promoters suitable for use in eukaryotic host cells are well known to those of skill in the art.

A ribosome binding site (RBS) is conveniently included in the expression cassettes of the invention that are intended for use in prokaryotic host cells. An RBS in *E. coli*, for example, consists of a nucleotide sequence 3–9 nucleotides in length located 3–11 nucleotides upstream of the initiation codon (Shine and Dalgarno, *Nature* (1975) 254: 34; Steitz, In *Biological regulation and development: Gene expression* (ed. R. F. Goldberger), vol. 1, p. 349, 1979, Plenum Publishing, NY).

Translational coupling can be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See, Squires et. al. (1988) *J. Biol Chem.* 263: 16297–16302.

The pest resistance polypeptides can be expressed intracellularly, or can be secreted from the cell. Intracellular expression often results in high yields. If necessary, the amount of soluble, active pest resistance polypeptide may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the pest resistance polypeptides are secreted from the cell, either into the periplasm or into the extracellular medium, the DNA sequence is linked to a cleavable signal peptide sequence. The signal sequence directs translocation of the pest resistance polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad Sci. USA* (1985) 82: 7212; Talmadge et al., *Proc. Natl. Acad. Sci. USA* (1980) 77: 3988; Takahara et al., *J. Biol. Chem.* (1985) 260: 2670).

The pest resistance polypeptides of the invention can also be produced as fusion proteins. This approach often results in high yields, because normal prokaryotic control sequences direct transcription and translation. In *E. coli,* lacZ fusions are often used to express heterologous proteins. Suitable vectors are readily available, such as the pUR, pEX, and pMR100 series (see, e.g., Sambrook et al., supra.). For certain applications, it may be desirable to cleave the non-pest resistance polypeptide amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

A suitable system for obtaining recombinant proteins from *E. coli* which maintains the integrity of their N-termini has been described by Miller et al. (1989) *Biotechnology* 7:698–704. In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant pest resistance polypeptides can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology* Vol. 182: *Guide to Protein Purification.,* Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

One of skill would recognize that modifications can be made to the pest resistance polypeptides without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

The polypeptides encoded by the optimized pest resistance genes can be formulated for application to plants as is known to those of skill in the art. For Bt toxins, for example, one or more forms of the toxin (e.g., crystals, crystal proteins, protoxin, toxin, and insecticidally effective portions of the toxins) can be formulated for application to plants, or for assays of insecticidal activity. The active pest resistance polypeptide can be formulate with suitable carriers, diluents, emulsifiers and/or dispersants. This insecticide composition can be formulated in any of multiple forms, such as a wettable powder, pellets, granules or a dust, or as a liquid formulation with aqueous or non-aqueous solvents as a foam, gel, suspension, concentrate, etc. The concentration of the active ingredient in such a composition will depend upon the nature of the formulation and its intended mode of use. For extended protection (e.g., for a whole growing season), additional amounts of the composition can be applied periodically.

The pesticidal polypeptides can be formulated in a dry, solid unit dosage form, such as capsules, boluses or tablets that contain the desired amount of active compound. These dosage forms are prepared by mixing the active ingredient with suitable diluents, fillers, disintegrating agents and/or binders such as starch, lactose, talc, magnesium stearate, vegetable gums and the like. Such unit dosage formulations may be varied widely with respect to their total weight and content of the pesticidal agent, depending upon the factors such as the type of plant to be treated and the severity and type of infestation.

B. Treatment of Plants with Microorganisms that Express Optimized Pest Resistance Genes The optimized insect resistance genes, or insecticidally effective portions thereof, can be introduced into microorganisms that can colonize plants. Ingestion by a pest of a plant upon which the microorganisms are present results in the gene product of the pest resistance gene causing the death of the pest. Microbes capable of colonizing plant phytospheres are described in, for example, U.S. Pat. No. 5,281,532 and European Patent Application 0 200 344. Methods of introducing and expressing genes into microorganisms are described herein and are otherwise well known to those skilled in the art (see, e.g., U.S. Pat. No. 5,135,867).

Microorganism hosts are selected which are known to occupy the "phytosphere" of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the polypeptide from environmental degradation and inactivation. Host microorganisms of particular interest include prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae (including photobacterium), Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycete yeast, such as Rhodotorula, Aureobasidium, Sporobolomyces, and the like.

Application of microorganisms transformed with optimized pest resistance genes to plants can be accomplished using methods known to those of skill in the art (see, e.g., US Pat. No. 5,281,532. Typically, the transformed microorganism is applied to its natural habitat, such as the rhizosphere or phylloplane of the plant to be protected from the pest. The microorganisms grow in their natural habitat, and produce the pesticidal agent encoded by the pest resistance gene. The agent is absorbed and/or ingested by the larvae or adult pest, or have a toxic effect on the ova. Long-term protection of the plants is provided by the persistence of the microorganisms, but repetitive administrations may be required from time to time. The recombinant organisms can be applied by spraying, soaking, injection into the soil, seed coating, seedling coating or spraying, or the like. Where administered in the field, generally concentrations of the organism will be from $10^6$ to $10^{10}$ cells/ml, and the volume applied per hectare will be generally from about 0.1 oz to 2 lbs or more. Where administered to a plant part, the concentration of the organism will usually be from $10^3$ to $10^6$ cells/cm$^2$.

C. Introduction of Insect Resistance Genes into Plant Cells

In another embodiment, the optimized recombinant pest resistance genes produced as described herein are introduced into plant cells, including plant cells that are present in an intact plant or plant part. Expression of the recombinant resistance gene then confers resistance upon the plant or plant part.

The invention provides expression cassettes that are useful for expressing optimized pest resistance genes in plants. In addition to the optimized pest resistance gene, the expression cassettes include polynucleotide sequences that function to direct expression of the gene. The expression cassettes typically include proper transcriptional initiation regulatory regions, i.e., a promoter sequence, an intron, and a polyadenylation site region recognized in the host plant of interest, all linked in a manner which permits the transcription of the coding sequence and subsequent processing in the nucleus. These sequences can be derived from any source, such as, virus, plant or bacterial genes. One example of a preferred source for transcription promoters and terminators is plant viruses such as, for example, cauliflower mosaic virus (CaMV), which is described in Hohn et al. (1982) *Curr. Topics Microbiol. Immunol.* 96: 194–220 and Appendices A to G. CAMV has at least two promoters that are functional in plants, namely the 19S promoter, which results in transcription of gene VI of CaMV, and the promoter of the 35S transcript. The CaMV 35S or 19S promoters may be enhanced by the method described in Kay et al. (1987) *Science* 236: 1299–1302.

Promoters and other control sequences from plant genes are also suitable for use in the expression of pest resistance genes prepared using the methods of the invention. Examples include those from a gene that encode the small subunit of ribulose bisphosphate carboxylase, and from a gene that codes for chlorophyll a/b-binding protein. See, e.g., Morelli et al. (1985) *Nature* 315: 200–204. Other suitable promoters include the full-length transcript promoter from Figwort mosaic virus, ubiquitin promoters, actin promoters, histone promoters, tubulin promoters, or the mannopine synthase promoter (MAS). One can use a promoter that causes preferential expression in a particular tissue, such as leaves, stems, roots, or meristematic tissue, or the promoter may be inducible, such as by light, heat stress, water stress or chemical application or production by the plant. Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters. The promoter may also be a pith-specific promoter, such as the promoter isolated from a plant TrpA gene as described in International Publication No. WO93/07278.

Bacterial genes that are expressed in plants are another source of suitable control regions. These include those present in the T-DNA region of Agrobacterium plasmids such as, for example, Ti plasmid of *A. tumefaciens* and the Ri plasmid of *A. rhizogenes*. Particularly preferred Agrobacterium promoters and 5' and 3' untranslated regions for use in the expression of optimized pest resistance genes include, for example, those of the genes that code for octopine synthase and nopaline synthase. See, e.g., Bevan et al. (1983) *Nature* 304: 184–187.

A variety of techniques for introducing genes into plant cells and obtaining expression of the genes are known in the art. Methods are known for introduction and expression of heterologous genes in both monocot and dicot plants. In addition to Berger, Ausubel and Sambrook, useful general references for plant cell cloning, culture and regeneration include Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). Cell culture media are described in Atlas and Parks (eds) The Handbook of Microbiological Media (1993) CRC Press, Boca Raton, Fla. (Atlas). Additional information is found in commercial literature such as the Life Science Research Cell Culture catalogue (1998) from Sigma-Aldrich, Inc. (St Louis, Mo.) (Sigma-LSRCCC) and, e.g., the Plant Culture Catalogue and supplement (1997) also from Sigma-Aldrich, Inc (St Louis, Mo.) (Sigma-PCCS). See also, e.g., U.S. Pat. Nos. 5,633,446, 5,317,096, 5,689, 052, 5,159,135, and 5,679,558; Weising et al. (1988) *Ann. Rev. Genet.* 22:421–477. Examples of suitable methods include *Agrobacterium tumefaciens* mediated transformation, direct gene transfer into protoplasts, microprojectile bombardment, injection into protoplasts, cultured cells and tissues or meristematic tissues, and electroporation. Microinjection techniques are known in the art and well described in the scientific and patent literature. The introduction of DNA constructs using polyethylene glycol precipitation is described in Paszkowski et al. (1984) *EMBO J.* 3:2717–2722. Electroporation techniques are described in Fromm et al. (1985) *Proc. Nat'l. Acad Sci. USA* 82:5824. Ballistic transformation techniques are described in Klein et al. (1987) *Nature* 327:70–73; these methods involve penetration of cells by small particles with the nucleic acid either within the matrix of small beads or particles, or on the surface. Although typically only a single introduction of a new nucleic acid segment is required, this method particularly provides for multiple introductions. Transformation of monocots is known using various techniques including electroporation (e.g., Shimamoto et al. (1992) *Nature* 338:274–276; biolistics (e.g., European Patent Application 270,356); and Agrobacterium (e.g., Bytebier et al. (1987) *Proc. Nat'l. Acad. Sci. USA* 84:5345–5349).

Agrobacterium tumefaciens-meditated transformation techniques are well described in the scientific literature. See, for example, Horsch et al. (1984) *Science* 233:496–498, and Fraley et al. (1983) *Proc. Nat'l. Acad. Sci. USA* 80:4803. In these methods, a plant cell, an explant, a meristem or a seed is infected with *Agrobacterium tumefaciens* transformed with the segment. Under appropriate conditions known in the art, the transformed plant cells are grown to form shoots, roots, and develop further into plants. The insect resistance gene can be introduced into appropriate plant cells, for example, by means of the T-DNA-containing Ti plasmid of *Agrobacterium tumefaciens*. T-DNA of Agrobacterium is commonly used as a vector for introducing heterologous DNA into plants. Both binary and insertion vectors are known. See, e.g., European Patent 0 120 516, Hoekema (1985) In: *The binary plant vector system,* Offset-drukkerij Kanters B. V., Alblasserdam, Chapter 5; Fraley el al., *Crit. Rev. Plant Sci.* 4: 1–46; An et al. (1985) *EMBO J.* 4: 277–287. The Ti plasmid is transmitted to plant cells upon infection by *Agrobacterium tumefaciens*, and is stably integrated into the plant genome (Horsch et al. (1 984) *Science* 233:496–498; Fraley et al. (1983) *Proc. Nat'l. Acad Sci. USA* 80:4803.

Typically, the vector used to introduce the insect resistance gene into a plant will include a selection marker. Selection markers confer on the transformed plant cells resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

Pathogens of the pest can also be used to introduce an optimized pest resistance gene into the target pest. For example, foreign genes have been expressed in baculovirus (a virus that infects insects) in order to improve the viral performance as a sprayable insecticide. In one example, recombinant *Bombyx mori* (silkworm) nuclear polyhedrosis virus (BmNPV) expressing an insect diuretic hormone gene effectively disturbed the insect larval fluid metabolism causing earlier death than the original BmNPV (Maeda (1989) *Biochem. Biophys. Res. Comm.* 165: 1177–1183). A shuffled gene encoding any protein that can cause the host insect to die can be inserted into the baculovirus. Any pathogen of the target pest, not only viruses but also bacteria, fungi, nematodes, etc., can be used to introduce the shuffled insecticidal protein genes into the pest to enhance their pathogenicity.

As one example, shuffled Bt insecticidal protein genes are used. A membrane spanning portion of Bt crystal protein called "Domain I" is cloned from several cryl-type genes by PCR using proper sets of primers. These amplified genes are mixed and shuffled. The shuffled genes are then cloned into baculovirus (AcNPV) expression vectors including those containing an early stage promoter (e.g., p10, gp64) or a late stage promoter (e.g. polyhedron) along with viral genome DNA. When the vector constructs are individually used to cotransfect Sf9 cells with viral DNA, which is cut open at the vector integration site, the recombinant viruses are obtained. The viruses propagated in Sf9 cells are tested in T. ni for speed of kill. One set of clones, which contain the shuffled Bt cry1 Domain I under an early stage promoter, shows significant improvement in the kill speed.

Nematodes are also useful for delivery of an insecticidal protein. Particularly, Sterinernema spp. are suitable for this application, because they contain gram-negative symbiotic bacteria. In fact, these symbiotic bacteria do produce its own set of insecticidal proteins (Bowen et al. (1998) *Science,* 280: 2129–2132). The insecticidal genes from *Photorhabdus luminescens* can be shuffled to improve its specific activity and/or host specificity. When nematode carrying the symbiotic bacterium invades insect larvae, it releases the bacterium into the insect body cavity. The bacterium then grows in the insect and produces the insecticidal protein.

Plant cells transformed with the optimized pest resistance genes can be regenerated to obtain intact plants that contain the transformed cells. See, e.g., European patent publications 0,116,718 and 0,270,822, PCT publication WO 84/02, 913 and European patent application 87/400,544.0. The plants can form germ cells and transmit the pest resistance genes to progeny plants, which can be grown in a normal manner and crossed with other plants. Such regeneration techniques generally rely on manipulation of certain phytohormones in a tissue culture growth medium, typically relying on a biocide and/or herbicide marker which has been introduced together with the shuffled nucleotide sequences. Plant regeneration from cultured protoplasts is described in Evans et al., *Protoplasts Isolation and Culture, Handbook of Plant Cell Culture,* pp. 124–176, MacMillan Publishing Company, New York, 1983; and Binding, *Regeneration of Plants, Plant Protoplasts,* pp. 21–73, CRC Press, Boca Raton, 1985. Regeneration can also be obtained from plant callus, explants, organs, or parts thereof Such regeneration techniques are described generally in Klee et al. (1987) *Ann. Rev. of Plant Phys.* 38:467–486. To obtain plants that are homozygous for the improved gene, one can reproduce the plants and test those progeny that are resistant to the particular pathogen.

The invention includes plants, plant parts, and plant cells that contain an optimized pest resistance gene such as those prepared using the methods described herein. Progeny and other descendents of such plants are also within the scope of the invention.

D. Introduction of Pest Resistance Genes into Insect Viruses

The optimized pest resistance genes obtained using the methods described herein can also be introduced into viruses that infect pests. Introduction of a pest resistance gene into a virus can enhance the pathogenicity of the virus. Viruses that infect insects include, for example, baculoviruses and entomopoxviruses. Methods for inserting genes into insect viruses are well known and readily practiced by those skilled in the art (see, e.g., Merryweather et al. (1990) *J. Gen. Virol.* 71:1535–1544 and Martens et al. (1990) *Appl. Environmental Microbiol.* 56: 2764–2770.

Automation for Strain Improvement and Intergrated System

One aid to strain improvement is having an assay that can be dependably used to identify a few mutants out of thousands that have potentially subtle increases in product yield or insect resistance/toxicity activity. The limiting factor in many assay formats is the uniformity of library cell (or viral) growth. This variation is the source of baseline variability in subsequent assays. Inoculum size and culture environment (temperature/humidity) are sources of cell growth variation. Automation of all aspects of establishing initial cultures and state-of-the-art temperature and humidity controlled incubators are useful in reducing variability.

In one aspect, library members, e.g., cells, viral plaques, spores or the like, are separated on solid media to produce individual colonies (or plaques). Using an automated colony picker (e.g., the Q-bot, Genetix, U.K.), colonies are identified, picked, and 10,000 different mutants inoculated into 96 well microtiter dishes containing two 3 mm glass balls/well. The Q-bot does not pick an entire colony but rather inserts a pin through the center of the colony and exits with a small sampling of cells, (or mycelia) and spores (or viruses in plaque applications). The time the pin is in the colony, the number of dips to inoculate the culture medium, and the time the pin is in that medium each effect inoculum size, and each can be controlled and optimized. The uniform process of the Q-bot decreases human handling error and increases the rate of establishing cultures (roughly 10,000/4 hours). These cultures are then shaken in a temperature and humidity controlled incubator. The glass balls in the microtiter plates act to promote uniform aeration of cells and the dispersal of mycelial fragments similar to the blades of a fermenter.

A high throughput method for detecting analyte molecules from a complex biological matrix is by electrospray tandem mass spectrometry as taught in "HIGH THROUGHPUT MASS SPECTROMETRY" by Sun Ai Raillard, U.S. Pat. No. 60/119,766, filed Feb. 11, 1999. In the '766 application, methods which utilize off-line parallel sample purification and fast flow-injection analysis, typically reducing the time of analysis to 30 to 40 seconds per sample.

Generally, all steps starting from cell picking, cell growth, sample preparation and analysis are automated and can be carried out overnight by various robotic workstations. A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the present invention, e.g., for high-throughput screening of molecules assembled from the various oligonucleotide sets described herein. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like. A variety of commercially available peripheral equipment and software is available for digitizing, storing and analyzing data, e.g., using PC (Intel x86 or Pentium chip- compatible DOSE™, OS2™ WINDOWS™, WINDOWS NT™ or WINDOWS95–98™ based machines), MACINTOSH™, LINUX, or UNIX based (e.g., SUN™ work station) computers.

Integrated systems for assay analysis in the present invention typically include a digital computer with e.g., high-throughput liquid control software, data digitization software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature, an image scanner for digitizing signals from assay components and the like.

Of course, these assay systems can also include integrated systems incorporating nucleic acid selection elements for screening, such as a computer, database with nucleic acid sequences of interest, sequence alignment software and the like. In addition, this software can include components for ordering selected oligonucleotides (e.g., used in oligonucleotide mediated shuffling of insect resistance genes), and/or directing synthesis of oligonucleotides or genes by an operably linked oligonucleotide synthesis machine. Thus, the integrated system elements of the invention optionally include any of the above components to facilitate high throughput recombination and selection. It will be appreciated that these high-throughput recombination elements can be in systems separate from those for performing selection assays, or the two can be integrated.

In the high throughput assays of the invention, it is possible to screen up to several thousand different shuffled variants in a single day. In particular, each well of a microtiter plate can be used to run a separate assay, or, if concentration or incubation time effects are to be observed, every 5–10 wells can test a single variant. Thus, a single standard microtiter plate can assay about 100 (e.g., 96) reactions. If 1536 well plates are used, then a single plate can easily assay from about 100-about 1500 different reactions. It is possible to assay several different plates per day; assay screens for up to about 6,000–20,000 different assays (i.e., involving different nucleic acids, encoded proteins, concentrations, etc.) is possible using the integrated systems of the invention. More recently, microfluidic approaches to reagent manipulation have been developed, e.g., by Caliper Technologies (Mountain View, Calif.).

EXAMPLES

The following examples are offered solely for the purposes of illustration, and are intended neither to limit nor to define the invention.

EXAMPLE 1

Optimization of Cry1 Toxin by DNA Shuffling

The cry1C gene, including its own promoter (5' region up to −260 nt), is used as the substrate for DNA shuffling. After DNA shuffling, the protein coding region is cloned into an expression vector, and *E. coli* cells are transformed. The transformed cells are incubated in a bacterial culture medium (nutrient broth) at 30° C. for 72 hr, after which the cells formed inclusion bodies consisting of the Cry1C protein. The cells are then harvested by either centrifugation or filtration and lysed with lysozyme to release free inclusion body. Alternatively, lysis can be achieved by treatment with a detergent, sonication, or other methods known to those of skill in the art. The inclusion body is collected by either centrifugation or filtration and exposed to an alkaline solution (pH 10.5) with or without a disulfide bond reducing agent (e.g., 2-mercaptoethanol). The Cry1C protein dissolved in the alkaline solution is then activated by trypsin. Trypsin digests the Cry1C protein down to the 66 kDa core. This trypsin digested core, which is the active form of Cry1-type Bt insecticidal proteins such as Cry1C, is purified with DEAE ion exchange resin. The activated Cry1C protein is absorbed onto DEAE ion exchanger at pH 10.5 and then eluted with salt such as sodium chloride or ammonium acetate. Ammonium acetate is particularly desirable because it can be evaporated during the subsequent concentration process. The activated protein is then concentrated either by lyophilization or evaporation under vacuum and used in screening. All the protein isolation processes described above are done in 96-well plates by high throughput format using a robot. A robot which is designed for DNA/RNA isolation is modified to use for this purpose.

The cry1C gene is shuffled with other cry genes that are homologous to cry1C. To obtain the homologous genes, two oligonucleotide primers are synthesized based on the Cry1C 5' regions that contain the ribosome binding site and the trypsin activation site (approximately 1800 nucleotides into the Cry1C protein coding region). These primers are used to amplify the toxic portion of previously unknown cry genes from a B. thuringiensis isolate. Normally, a B. thuringiensis strain contains multiple cry genes (as many as seven or more) and these genes are often reasonably similar in sequence to cry1 C. From one B. thuringiensis isolate, four cry genes are amplified. The amplified clones are cloned into E. coli, and selected clones are tested for sequence diversity by restriction mapping. For mapping, restriction enzymes that have a 4 bp recognition sequence (e.g., Sau3A) are used. Those cloned genes having restriction maps that are similar to, but substantially different from, that of cry1C are selected for shuffling with cry1C. Alternatively, the cloned cry genes are analyzed for diversity by multiple primer PCR analysis as described in Kalman el al. (1993) *Appl. Environ. Microbiol.* 59: 1131–1137.

After DNA shuffling, host cells (*E. coli* or a bacillus) sometimes failed to produce the full length Cry proteins. This is due to undesirable mutations which make the Cry protein unstable even in *E. coli* cells. Unstable mutants of the Cry protein are normally inactive in insects, because insects can digest the proteins into non-active fragments. Therefore, it is desirable to preselect those unstable mutants. In order to find those which failed to produce the Cry protein, an immunoassay (e.g., ELISA) is performed. An antiserum made against a C-terminal portion of the Cry protein is used. When the Cry protein is not formed as a full length stable protein (i.e., 135 kDa), the antiserum made against the C-terminal Cry protein failed to react. The antiserum directed towards the C-terminal portion can be made by absorption of an antiserum which had been made against the full length Cry protein with an truncated Cry protein with its C-terminus missing. Alternatively, the C-terminus can be tagged with a common marker, such as histidine residues. Another alternative analysis method involves subjecting the mutant Cry proteins to SDS-PAGE.

EXAMPLE 2

Shuffling of Insecticidal Toxin Genes of Bacillus Popilliae

*Bacillus popilliae,* which is known to be a pathogen of scarab beetles such as Japanese beetle, produces an insecticidal protein called Cry18Aa (Zhang et al. (1997) *J. Bacteriol.* 179: 4336–4341). The insecticidal activity of this protein is not sufficiently high, however, for large-scale use to prevent crop damage caused by beetle infestation. This Example describes the optimization of Cry1 18Aa by shuffling the cry18Aa gene of *B. popilliae* and cry2, which is its homologous gene of *B. thuringiensis.*

The cry18Aa gene is amplified by polymerase chain reaction (PCR) from B. popilliae using two primers, which are designed according to the published sequence (GenBank accession number: X99049). The forward primer (5'-gaaggaggctattggCCatgGac-3': SEQ ID NO:1) is based on the sequence around the ribosome binding site and translation start signal. The sequence is modified as indicated with capital letters to include an NcoI site at the translation start site. The reverse primer (5'-ATATGGATCCTTAGTGATGGTGATG GTGATGataaagaggagtgtcatctgc-3': SEQ ID NO:2) is based on the sequence around the translation termination. This primer includes a coding sequence for six consecutive histidine residues and a BamHII restriction site (capital letters) at the end of the cry18Aa protein-coding region. The His tag is later used to purify the proteins produced by *E. coli* cells that contain the shuffled genes. The amplification is made from the lysed *B. popilliae* cell by using a standard PCR method as described in the case of cry2 genes below.

Several different gene libraries are produced by DNA shuffling between the cloned cry18Aa gene and its homologous genes. The cry2 genes of *B. thuringiensis* are known to be homologous to *B. popilliae* cry18Aa gene. The known cry2 genes are amplified by PCR from several strains of *B. thuringiensis* (e.g. Bt kurstaki HD1 strain). *B. thuringiensis* cells are lysed in a PCR tube at 100° C. and used as a template. The cry2 genes are amplified by PCR using a standard PCR protocol with appropriate primers that are designed based on published cry2A sequences (e.g., GenBank accession Nos: M31738, M23724, X57252, etc.). Additional genes homologous to cry18Aa are cloned and shuffled with cryl8Aa. Genomic libraries of several *B. thuringiensis* and *B. popilliae* strains are screened with the cloned cry18Aa gene by Southern hybridization. In order to make the genomic libraries, DNA from *B. thuringiensis* and B. popilliae is partially digested with Sau3A to produce 1–10 kb fragments. Fragments of about 4 kb (3 to 5 kb range) are isolated by gel electrophoresis and cloned in pBluescript (Stratagene). Several cry18Aa-homologous genes are cloned from various *B. popilliae* isolates and *B. thuringiensis* strains such as Bt kurstaki, Bt kenyae and Bt tolworthi subspecies.

The protein coding region of the shuffled genes is amplified by PCR and cloned into an expression vector as described by Sasaki el al. ((1996) *Curr. Microbiol.* 31, 195–200). For high expression in *E. coli,* a portion of the cry promoter between the ApaI and NdeI sites is removed from the original vector described by Sasaki et al. *E. coli* as well as cry⁻*B. thuringiensis* are transformed with the vector containing the shuffled genes. The transformants are screened by immunoassay with anti-6X-His-antiserum for the production of the insecticidal protein, and positive clones are saved for the screening as described below.

When shuffled cry genes are expressed in *E. coli,* the cells typically produce the toxin polypeptide as an inclusion body. The inclusion bodies are liberated by dissociating *E. coli* cells with a determent such as B-PER Bacterial Protein Extraction Reagent (Pierce) according to the manufacture's recommended procedure. The detergent is removed by filtration, and the inclusion body is dissolved with 0.02N NaOH. After pH of the solution is neutralized with 100 mM Tris-HCl, pH 8, the insecticidal protein encoded by the shuffled gene is purified by Ni-NTA agarose (Qiagen) in a 96-well filter plate. A sufficient amount of E. coli cells is used to produce an amount of the insecticidal proteins, which always exceed the capacity of Ni-NTA agarose regardless of the expression level. This is to obtain a roughly equal amount of the protein from each 96 wells.

The proteins produced by the shuffled genes are placed on insect diet and allowed to be consumed by cucumber beetle. Mortality is observed to assess the activity level of each protein sample. In order to increase the screening efficiency, 10 protein samples are pooled and tested for the activity. The amount of protein used in each test is reduced to a sublethal dose, which is determined with the wild-type Cry18Aa protein. Pooled samples showing some insect mortality are decoded into 10 individual components to pinpoint a sample or samples responsible for the mortality. Positive samples are selected for second round of shuffling.

Several rounds of shuffling are performed for substantially increased potency of the *B. popilliae* Cry18Aa insecticidal protein.

EXAMPLE 3

Cloning of Previously Unknown Genes From Insect Pathogens that Encode Insecticidal Proteins Genomic DNA is prepared from several insect pathogens such as *Pseudomonas aeruginosa* and *Serratia entomophila*. The DNA samples are digested with several enzymes, including NotI, BamHI and SphI. The fragments produced with these enzymes are fractionated by size and cloned in a cosmid vector, e.g., Supercos (Stratagene), or a lambda vector, e.g., Lambda Zap (Stratagene) depending on the size. *E. coli* libraries containing insect pathogen DNA are then screened for insecticidal activity using tomato hornworm and cucumber beetles. *E. coli* cells are cultured in LB broth for 48 hr at 30° C. and harvested by centrifugation. The precipitated cells are resuspended in a minimum amount of water and placed on insect diet. Insects are allowed to feed on this diet for 3 days. Several cosmid clones showing insecticidal activity are identified, and DNA is isolated.

The cosmid DNA from those cells that have insecticidal activity is partially digested with Sau3A to obtain fragments of about 4 kb. The fragments are end-repaired with Klenow and cloned into the SmaI site of pBluescript (Stratagene). After screening about 4000 pBluescript subclones from one insect pathogen, several clones showing insecticidal activity are typically obtained. These positive clones are used as probes to screen by Southern hybridization to find homologous insecticidal genes within the same genus.

Homologous genes from Pseudomonas and Serratia species showing insecticidal activity are combined in two groups and shuffled for higher activity as described in this invention. The shuffled genes are cloned in *E. coli* and selected for higher insecticidal activity as described in Example 2 for *B. popilliae* Cry18Aa.

EXAMPLE 4

Toxins with Improved Activity Against Corn Rootworm Obtained by DNA Shuffling

This Example describes a method by which a family of homologous genes are shuffled to obtain toxins that exhibit improved activity against corn rootworm. Several sets of Bt cry genes are shuffled. A number of Bt Cry proteins are said to be active against beetles (e.g., cry3Ba, cry3Bb, cry3Aa, cry3Ca, cry1Ia, cry1Ib, cry1Bc, cry1Bb, cry1Ba, cry1Ka, cry7Aa, cry7Ab, cry8Aa, cry8Ba, cry8Ca, cry9Da, cry2Aa, cry2Ab, cry18Aa and cry14Aa). Unfortunately the toxins encoded by these genes are known to be inactive or weakly active against corn rootworm, thus indicating that they are good candidates for DNA shuffling. When their sequences are compared, we find that they can be grouped by sequence homology in 4 families. The family 1 includes cry3Ba, cry3Bb, cry3Aa and cry3Ca; the family 2 includes cry1Ia, cry1Ib, cry1Bc, cry1Bb, cry1Ba and cry1Ka; the family 3 includes cry7Aa, cry7Ab, cry8Aa, cry8Ba, cry8Ca and cry9Da; and the family 4 includes cry2Aa, cry2Ab, cry18Aa and cry14Aa. These genes can be amplified by PCR from appropriate Bt strains. Or, new, undisclosed genes can be cloned from Bt by screening Bt isolates by Southern blotting using a DNA probe synthesized based on any of these published sequences.

Each of the families are individually shuffled. Since they all are active against beetles and some (e.g. cry3Bb) are active against corn rootworm, one can identify shuffled genes that encode toxins having improved activity against corn rootworm. Shuffling, gene expression, protein isolation, and screening are essentially done by the methods described herein.

EXAMPLE 5

Toxins with Improved Activity Against Nematodes

In this Example, a set of cry genes are shuffled to obtain genes that encode toxins having increased activity against nematodes. Genes that are shuffled include Bt cry5Aa, cry5Ab, cry5Ac, cry6Aa, cry6Ba, cry12Aa, cry13Aa and cry21Aa. They can be grouped and shuffled as described above. Toxins encoded by the shuffled genes are tested for activity against the target nematodes.

EXAMPLE 6

Use of Nematodes for Introducing an Optimized Gene Inot a Pest

This Example describes one method of using nematodes to introduce a shuffled gene into an insect. Cyt genes from Bt are shuffled for better cytolytic activity. Cyt proteins of Bt are known to recognize specific phospholipids on insect cells and insert the molecule into cell membrane to disrupt the membrane function. Its mode of action substantially differs from that of Cry proteins and also from that of Bt. There are several analogs within the cyt gene family (e.g., cyt1Aa, cyt1Ab, cyt1Ba, cyt2Aa, cyt2Ba and cyt2Bb). Some of these genes, including cyt1Aa, cyt1Ba and cyt2Ba, are cloned from appropriate Bt hosts using PCR techniques as described herein. The cloned genes are mixed and shuffled. The shuffled genes are cloned in a Bacillus expression vector as described by Sasaki et al. ((1996) *Curr. Microbiol.* 31: 195–200) and used to transform a cry-negative Bt strain. Cyt proteins expressed in Bt are tested for cytotoxicity using Sf9 cells.

Those clones that exhibit improved cytotoxicity can be introduced into *Xenorhabdus luminescens* (a symbiotic bacterium of an insecticidal nematode). Cyt genes are amplified from Bt clones showing improved cytotoxicity with primers made on vector portions, and the amplified genes are cut with one or more appropriate restriction enzymes to release the coding region and portions of flanking regions. This fragment is cloned into pTZ19R with the 20-kDa protein gene associated with cyt1A in *Bt israelensis* and used to transform *Xenorhabdus luminescens*. This 20-kDa protein preserves the viability of host cells and promotes expression of the shuffled cyt genes (Wu et al. (1 993) *J. Bacteriol.* 175: 5276–5280). Recombinant *X. luminescens* is cocultivated with nematode, *Steinernema glaseri*. When tested against scarab beetles, it is found that the nematode harboring the recombinant *X. luminescens* requires a much lower dose to kill the insect than that the nematode with non-recombinant *X. luminescens*.

EXAMPLE 7

Optimization of a Protease Inhibitor Gene

A cysteine protease inhibitor gene is amplified by PCR from corn c-DNA utilizing a reported DNA sequence (GenBank: D38130). There are a number of homologous genes found in rice, sorghum, cowpea, soybean, cabbage, potato, etc. DNA encoding a portion (from 25 aa to 100 aa) of rice, soybean and cabbage cysteine protease inhibitor genes is synthesized. These synthesized genes are mixed with the corn inhibitor gene and shuffled. The shuffled genes are then cloned in an *E. coli* expression system, pQE-60, from Qiagen. The shuffled genes are then expressed, and proteins are purified with Ni-NTA agarose in 96-well plates. Purified proteins are then tested for their protease activity using crude preparation of cysteine protease prepared from white grubs. Actively feeding white grubs are collected in the field and homogenized. After cell debris is removed by centrifugation, the supernatant is used as the protease preparation without further purification. The grub protease preparation is mixed with shuffled inhibitors and incubated for 20 min. The protease activity is determined by fluorescent assay using Enzchek from Molecular Probe. Enzchek utilizes fluorescent dye-labeled protein in which the dye molecules are arranged in the way that fluorescence is quenched. When protease digests the protein, the dye becomes fluorescent. A large number of shuffled inhibitor clones are identified as active by the protease assay. Those active clones are screened for insecticidal activity by Agrobacterium rhizogenes method as described in this invention.

EXAMPLE 8

Cytotoxicity Assay

Insecticidal proteins including those described in this invention are often cytotoxic. For example, Bt Cry and Cyt proteins are known to kill cultured insect cells when they are properly activated. In the examples below, we describe methods we used to screen shuffled insecticidal gene products.

When disrupted by the insecticidal proteins, the insect cells release a substantial amount of ATPase. The ATPase activity in the supernatant can be used as an indicator of the cytotoxicity of an insecticidal protein. The shuffled Bt Cry proteins that have been tagged with 6X-His are purified with Ni-NTA agarose as described before. The purified proteins are then digested with 1/100 volume (w/w) trypsin for 30 min to activate the protein. Several Lepidoptera insect cell lines, such as Sf9 and TN368 (Trichoplusia ni) are used. The trypsin-activated Cry proteins are mixed with the cells in 96-well plate at 0.1 to 1 ppm and incubated for 60 min. After the incubation, the cells are removed by filtration and ATPase activity is measured by luciferase-luciferin assay (Sigma). This ATPase method is more sensitive than other methods such as dye exclusion method in which the cell death is determined by staining with a dye like trypan blue. Dead cells are stained with trypan blue while live cells are not.

EXAMPLE 9

Shuffling the BT CRY Gene

In order to increase the diversity of the shuffled gene library, a Bt cry gene or genes (called the primary genes) are shuffled using synthetic oligonucleotide shuffling (See, Crameri et al. "OLIGONUCLEOTIDE MEDIATED NUCLEIC ACID RECOMBINATION" filed Feb. 5, 1999, U.S. Pat. No. 60/118,813). In brief, a family of homologous insect resistance nucleic acid sequences are first aligned, e.g. using available computer software to select regions of identity/similarity and regions of diversity. A plurality (e.g., 2, 5, 10, 20, 50, 75, or 100 or more) of oligonucleotides corresponding to at least one region of diversity are synthesized. These oligonucleotides can be shuffled directly, or can be recombined with one or more of the family of nucleic acids.

The oligonucleotide sequence can be taken from other genes called secondary genes. The secondary genes have a certain degree of homology to the primary genes. There are several ways to select parts of the secondary gene for the oligonucleotide synthesis. For example, portions of the secondary gene can be selected at random. The DNA shuffling process will select those oligonucleotides, which can be incorporated into the shuffled genes. The selected portions can be any lengths as long as they are suitable to synthesize. The oligonucleotides can also be designed based on the homology between the primary and secondary genes. A certain degree of homology is necessary for crossover, which must occur among DNA fragments during the shuffling. At the same time, strong heterogeneity is desired for the diversity of the shuffled gene library. Furthermore, a specific portion of the secondary genes can be selected for the oligonucleotide synthesis based on the knowledge in the protein sequence and function relationship. A large number of reports (extensively cited in a review article: "*Bacillus thuringiensis* and its pesticidal crystal proteins," Schnepf, E. et.al., 1998, Microbiology and Molecular Biology Reviews, vol. 62, page 775) indicate that the "domain II" which is normally the middle portion of the fully activated Bt crystal proteins is important for Bt In the case of Cry1A-type proteins, domain II starts at about the 200th amino acid resides and ends at about the 410th residue. This domain was found to be important for the insect specificity of the Bt toxins. When the insect specificity is modified by the current invention utilizing the DNA shuffling technology, the domain II portion of the nucleotide sequence of the secondary genes can be selected as a target region for synthesizing oligonucleotides used in an oligonucleotide shuffling procedure.

Domain I, which is the N-terminal portion of the fully activated Bt crystal protein proximal to domain H, is involved in the membrane spanning function (see the review of Schnepf et al.) of Cry. Since the insecticidal activity of the Bt crystal protein is, at least in part, dependent of this function, the domain I portion of the secondary genes can be selected for oligonucleotide shuffling for increased insecticidal activity. Domain III, which is the C-terminal portion of the fully activated Bt crystal protein after domain II, can also be selected for the oligonucleotide synthesis. This domain is occasionally involved in the insect specificity (see Schnepf et al.).

Figure 3:
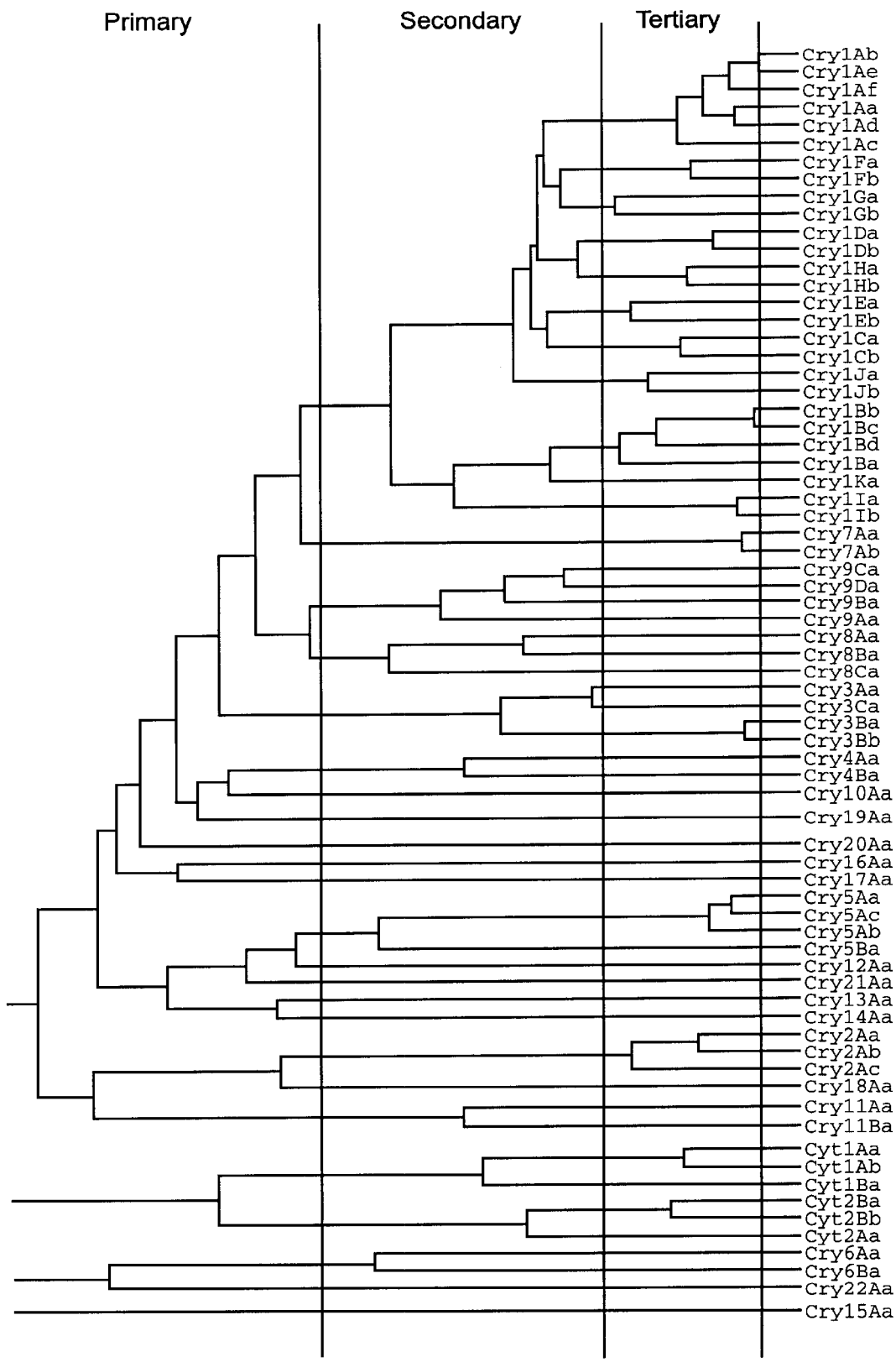
FIG. 3 shows a dendogram of a greater number of Bt toxin genes.
Figure 5:
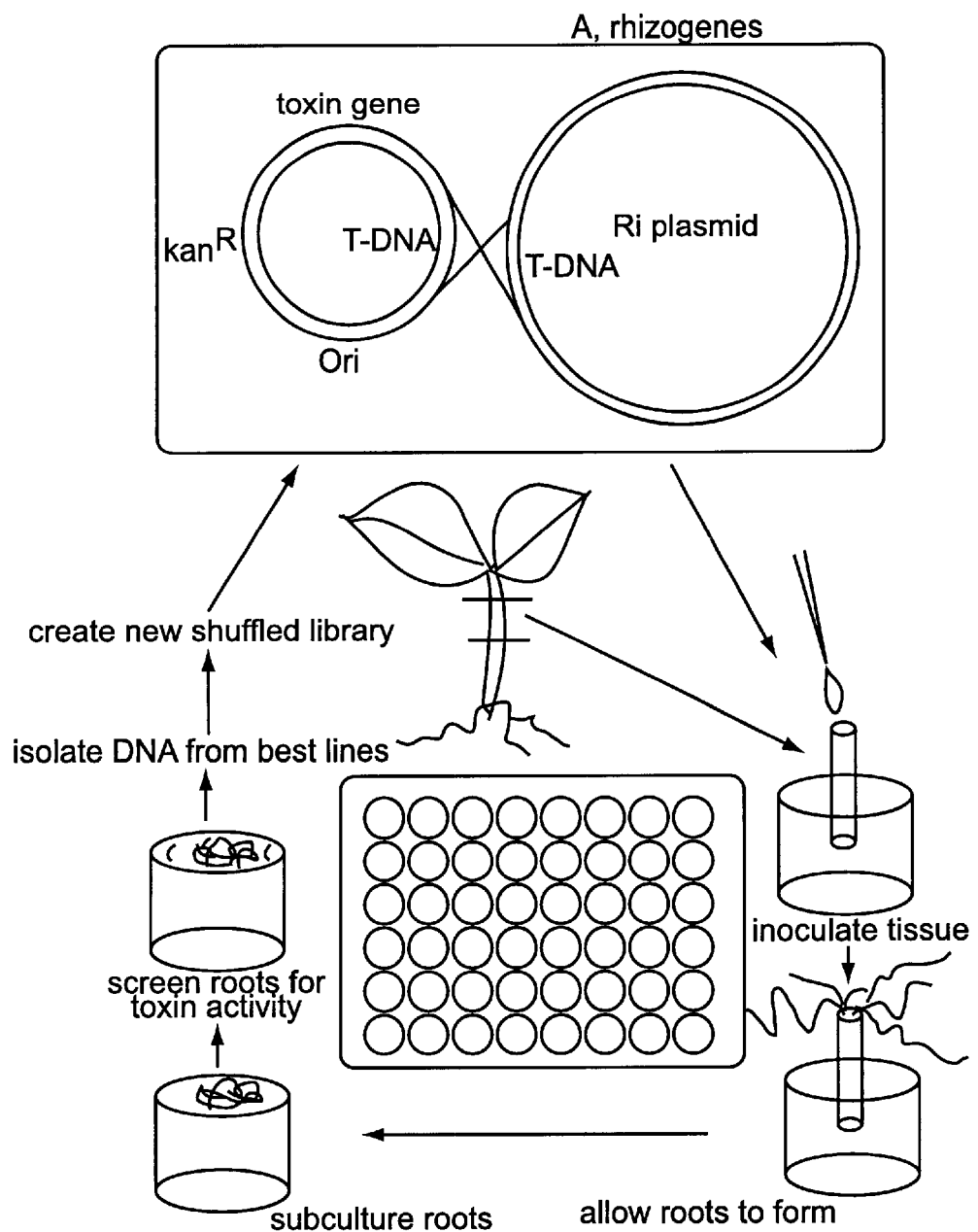
FIG. 5 shows a schematic of a method for using *A. rhizogenes* to insert a shuffled toxin gene into hairy roots, which are then screened for the presence of toxin activity against a pest of interest.

In one aspect, the primary cry2Aa and cry2Ab genes were shuffled with several oligonucleotides that were synthesized based on the secondary cry2Ac gene sequence. Cry2Aa and cry2Ab are highly homologous, but cry2Ac is substantially different from these genes (see, e.g., FIG. 3). Therefore, it was desirable to shuffle cry2Ac along with the cry2Aa and cry2Ab to increase the diversity of resulting shuffled recombinant nucleic acids. Portions of the cry2Ac sequence, which are substantially different from the corresponding portions of cry2Aa and cry2Ab, were selected, and a series of 50-mer oligonucleotides that cover these portions were synthesized. These oligonucleotides were shuffled with the protein-coding region of cry2Aa and cry2Ab. When a certain number of the clones were selected from the shuffled gene library and examined for the diversity by restriction mapping, good diversity was observed. The diversity was more than normally expected from the shuffling of cry2Aa and cry2Ab alone.

Alternatively, a portion of the secondary genes can be obtained by PCR amplification. The PCR amplified DNA can be shuffled with the primary genes. The selection criteria mentioned above for the oligonucleotides can be applied to the PCR amplification. The portions to be amplified can be randomly selected. Or, the selection can be based on the sequence homology and heterogeneity. Also, the selection can be made based on the seqeuence and function relationship. The PCR amplified portions can be domain I for higher insecticidal activity or domain II/III for different insect specificity. Like synthesized oligonucleotides, the PCR amplified portions of the secondary genes can be shuffled with the primary genes.

EXAMPLE 10

High-Throughput Screen for Insecticidal Actwjty

This example provides an example high throughput strategy for obtaining new insecticidal genes and proteins. First, the nucleic acids of choice (e.g., Bt genes or gene fragments) are recombined. The resulting recombinant nucleic acids are transformed into a strain of *Bacillus thuringiensis* that expresses the recombined nucleic acids in an active protein form. Colonies are picked with the Q-bot as described supra. Optionally, pools of transformed cells are grown in each well to increase the number of colonies which are screened in the initial screening round. For example, screening 100 colonies in a well for 10,000 wells provides a screen of $10^6$ colonies.

Sporulation is induced in a standard 96 (or more) well format. Several larvae are added to each well. The plate is covered with an air permeable membrane which retains the larvae in the wells in which they were placed. Larvae are allowed to feed until they receive a lethal dose from any spores expressing an insecticidal protein. The larvae are moved to an incubation chamber and allowed to mature into insects. Mature insects fly passively away, e.g., by using a chemoattractant, or chemorepellant. All of the dead larvae are harvested. The larvae contain insecticidal spores (there are typically some false positives at this stage due to larvae that die due to experimental manipulations, rather than insecticidal proteins). The DNA from the larvae are recovered and the shuffled genes are recovered by PCR. The genes are recloned and the process repeated (e.g., by limiting dilution of different positive clones) to further enrich for insecticidal proteins. A library of such genes enriched for insecticidal activity is constructed. This library can be screened, shuffled and otherwise manipulated by any of the techniques discussed herein.

Thus, this example utilizes the ability of a bolus of spores encoding a shuffled Bt gene to kill larvae. The enrichment is based on separating dead larvae from larvae that ingest innocuous shuffled Bt toxins. Bt genes are recovered and the process is repeated.

In related aspects, this assay could be adapted to batericidal or fungicidal proteins by infecting bacteria or fungi with shuffled genes and separating live cells from dead cells, e.g., by FACS.

Modifications can be made to the method and materials as hereinbefore described without departing from the spirit or scope of the invention as claimed, and the invention can be put to a number of different uses, including:

The use of an integrated system to test insect resistance of shuffled DNAs, including in an iterative process. The integrated system typically includes a computer with software directing manipulation of fluids and cells as described above for assays directed to assessing insect resistance or toxicity.

An assay, kit or system utilizing a use of any one of the selection strategies, materials, components, methods or substrates hereinbefore described. Kits will optionally additionally comprise instructions for performing methods or assays, packaging materials, one or more containers which contain assay, device or system components, or the like.

In an additional aspect, the present invention provides kits embodying the methods and apparatus herein. Kits of the invention optionally comprise one or more of the following: (1) a shuffled component as described herein; (2) instructions for practicing the methods described herein, and/or for operating the selection procedure herein; (3) one or more insect resistance or toxicity assay component; (4) a container for holding insecticidal proteins, nucleic acids, plants, insects, cells, or the like and, (5) packaging materials.

In a further aspect, the present invention provides for the use of any component or kit herein, for the practice of any method or assay herein, and/or for the use of any apparatus, composition, library or kit to practice any assay or method herein.

While the foregoing invention has been described in some detail for purposes of clarity and understanding, it will be clear to one skilled in the art from a reading of this disclosure that various changes in form and detail can be made without departing from the true scope of the invention. For example, all the techniques and materials described above can be used in various combinations. All publications and patent documents cited in this application are incorporated by reference in their entirety for all purposes to the same extent as if each individual publication or patent document were so individually denoted.

What is claimed is:

1. A method of obtaining an optimized recombinant pest resistance gene, the method comprising:
  (1) recombining a plurality of forms of a nucleic acid which comprise segments derived from a gene that confers resistance to a pest upon a plant in which the gene is effectively expressed, wherein the plurality of forms of the nucleic acid differ from each other in two or more nucleotides, to produce a library of recombinant genes, wherein the library includes at least one optmized recombinant pest resistance gene that confers resistance to a pest upon a plant in which the gene is effectively expressed, wherein the optimized recombinant pest resistance gene exhibits improved pest resistance capability compared to a non-recombinant pest resistance gene;
  (2) expressing members of the library of recombinant genes, thereby producing polypeptides encoded by the expressed members of the library of recombinant genes; and
  (3) assaying the polypeptides for the ability to confer pest resistance upon a plant, thereby identifying the optimized recombinant pest resistance gene;
  wherein the optimized recombinant pest resistance gene is identified by observation of the improved pest resistance capability of the polypeptide encoded by the optimized recombinant pest resistance gene compared to a polypeptide encoded by a non-recombinant pest resistance gene.

2. The method of claim 1, wherein the method further comprises:
  (4) recombining the optimized recombinant pest resistance gene with an additional form of the pest resistance gene, which is the same or different from one or more of the plurality of forms of a nucleic acid of (1), to produce an additional library of recombinant genes, wherein the library includes at least one additional optimized recombinant pest resistance gene that confers resistance to a pest upon a plant in which the gene is effectively expressed, wherein the additional optimized recombinant pest resistance gene exhibits improved pest resistance capability compared to a non-recombinant pest resistance gene;
  (5) expressing members of the additional library of recombinant genes, thereby producing additional polypeptides encoded by the expressed members of the additional library of recombinant genes; and
  (6) assaying the additional polypeptides for the ability to confer pest resistance upon a plant, thereby identifying the additional optimized recombinant pest resistance gene;
  wherein the additional optimized recombinant pest resistance gene is identified by observation of the improved pest resistance capability of the polypeptide encoded by the additional optimized recombinant pest resistance gene compared to a polypeptide encoded by a non-recombinant pest resistance gene.

3. The method of claim 1, wherein the improved pest resistance capability comprises increased potency against the pest.

4. The method of claim 1, wherein the plurality of forms of a nucleic acid comprises one or more nucleic acid derived from or corresponding to one or more of: cry1Aa, cry1Ab, cry1Ac, cry1Ad, cry1Ae, cry1Af, cry1Ag, cry1Ba, cry1Bb, cry1Bc, cry1Bd, cry1Ca, cry1Cb, cry1Da, cry1Db, cry1Ea, cry1be, cry1Fa, cry1Fb, cry1Ga, cry1Gb, cry1Ha, cry1Hb, cry1Ia, cry1Ib, cry1Ic, cry1Ja, cry1Jb, cry1Ka, cry1Jc, cry2Aa, cry2Ab, cry2Ac, cry3Aa, cry3Ba, cry3Bb, cry3Ca, cry4Aa, cry4Ba, cry5Aa, cry5Ab, cry5Ac, cry5Ba, cry6Aa, cry6Ba, cry7Aa, cry7Ab, cry8Aa, cry8Ba, cry8Ca, cry9Aa, cry9Ba, cry9Ca, cry9Da, cry9Ea, cry10Aa, cry11Aa, cry11Ba, cry11bb, cry12Aa, cry13Aa, cry14Aa, cry15Aa, cry16Aa, cry17Aa, cry18Aa, cry19Aa, cry20Aa, cry21Aa, cry22Aa, cry23Aa, cry24Aa, cry25Aa, cry26Aa, cry27Aa, cry28Aa, cyt1Aa, cyt1Ab, cyt1Ba, cyt2Aa, cyt2Ba or cyt2Bb.

5. The method of claim 1, wherein the improved pest resistance capability comprises an increase in the range of pests that are susceptible to the pest resistance gene.

6. The method of claim 1, wherein the improved pest resistance capability comprises a decreased ability of a pest population to develop resistance to the pest resistance gene.

7. The method of claim 1, wherein the improved pest resistance capability comprises an increased expression level of a polypeptide encoded by the pest resistance gene.

8. The method of claim 7, wherein the optimized recombinant pest resistance gene comprises an increase in G-C content compared to a naturally occurring form of the pest resistance gene.

9. The method of claim 1, wherein the improved pest resistance capability comprises a decrease in susceptibility of a polypeptide encoded by the pest resistance gene to protease cleavage, high pH or low pH.

10. The method of claim 1, wherein the improved pest resistance capability comprises a decrease in toxicity to a host plant of a polypeptide encoded by the optimized recombinant pest resistance gene.

11. The method of claim 1, wherein the pest is selected from the group consisting of a nematode, a virus, and a bacterium.

12. The method of claim 1, wherein the pest is an insect.

13. The method of claim 12, wherein the insect is a larvae.

14. The method of claim 12, wherein the plurality of forms of the nucleic acid are derived from a gene which encodes a Bacillus toxin.

15. The method of claim 14, wherein the Bacillus is *Bacillus thuringiensis*.

16. The method of claim 14, wherein the *Bacillus thuringiensis* toxin is an δ-endotoxin.

17. The method of claim 1, wherein the plurality of forms of the nucleic acid comprise segments derived from one or more genes that encode a protease inhibitor, a polyphenol oxidase, an insecticidal protease, a vegetative insecticidal protein, a lectin, or a biosynthetic pathway for an insecticide.

18. The method of claim 17, wherein the gene encodes a vegetative insecticidal protein of a Bacillus species.

19. The method of claim 18, wherein the Bacillus species is selected from the group consisting of *B. cereus, B. popillae,* and *B. thuringiensis*.

20. The method of claim 18, wherein the Bacillus species is *B. spheracus*.

21. The method of claim 1, wherein assaying the potypeptides for the ability to confer pest resistance upon a plant comprises feeding the polypeptides to target pests.

22. The method of claim 21, wherein a plurality of the polypeptides are pooled prior to feeding to the target pests.

23. The method of claim 1 further comprising:

(a) inserting members of the library of recombinant genes into a plasmid to produce a plasmid library;

(b) introducing the plasmid library into *A. rhizogenes* cells;

(c) screening the product of step (b) for *A. rhizogenes* cells transformed with recombinant genes;

(d) incubating a plant tissue with the transformed *A. rhizogenes* cells;

(e) detecting the presence of root formation from the plant tissues.

24. The method of claim 23, wherein the plant tissue is derived from a seedling.

25. The method of claim 1, wherein the nucleic acid comprises one or more nucleic acid selected from: cry1Aa1, cry1Aa2, cry1Aa3, cry1Aa4, cry1Aa5, cry1Aa6, cry1Ab1, cry1Ab2, cry1Ab3, cry1Ab4, cry1Ab5, cry1Ab6, cry1Ab7, cry1Ab8, cry1Ab9, cry1Ab10, cry1Ac1, cry1Ac2, cry1Ac3, cry1Ac4, cry1Ac5, cry1Ac6, cry1Ac7, cry1Ac8, cry1Ac9, cry1Ac10, cry1Ad1, cry1Ae1, cry1Af1, cry1Ba1, cry1Ba2, cry1Bb1, cry1Bc1, cry1Bd1, cry1Ca1, cry1Ca2, cry1Ca3, cry1Ca4, cry1Ca5, cry1Ca6, cry1Ca7, cry1Cb1, cry1Da1, cry1Db1, cry1Ea1, cry1Ea2, cry1Ea3, cry1Ea4, cry1Eb1, cry1Fa1, cry1Fa2, cry1Fb1, cry1Fb2, cry1Ga1, cry1Ga2, cry1Gb1, cry1Ha1, cry1Hb1, cry1Ia1, cry1Ia2, cry1Ia3, cry1Ia4, cry1Ia5, cry1Ib1, cry1Ic1, cry1Ja1, cry1Jb1, cry1Ka1, cry2Aa1, cry2Aa2, cry2Aa3, cry2Aa4, cry2Ab1, cry2Ab2, cry2Ac1, cry3Aa1, cry3Aa2, cry3Aa3, cry3Aa4, cry3Aa5, cry3Aa6, cry3Ba1, cry3Ba2, cry3Bb1, cry3Bb2, cry3Ca1, cry4Aa1, cry4Aa2, cry4Ba1, cry4Ba2, cry4Ba3, cry4Ba4, cry5Aa1, cry5Ab1, cry5Ac1, cry5Ba1, cry6Aa1, cry6Ba1, cry7Aa1, cry7Ab1, cry7Ab2, cry8Aa1, cry8Ba1, cry8Ca1, cry9Aa1, cry9Aa2, cry9Ba1, cry9Ca1, cry9Da1, cry9Da2, cry9Ea1, cry10Aa1, cry11Aa1, cry11Aa2, cry11Ba1, cry11Bb1, cry11Bb1, cry12Aa1, cry13Aa1, cry14Aa1, cry15Aa1, cry16Aa1, cry17Aa1, cry18Aa1, cry19Aa1, cry19Ba1, cry20Aa1, cry21Aa1, cry22Aa1, cry24Aa1, cry25Aa1, cry26Aa1, cry28Aa1, cyt1Aa1, cyt1Aa2, cyt1Aa3, cyt1Aa4, cyt1Ab1, cyt1Ba1, cyt2Aa1, cyt2Ba1, cyt2Ba2, cyt2Ba3, cyt2Ba4, cyt2Ba5, cyt2Ba6, cyt2Bb1, 40kDa, cryC35, cryTDK, cryC53, vip1A, vip2A, vip3A(a), vip3A(b), and p21med.

26. The method of claim 17, wherein the pest resistance gene encodes a cholesterol oxidase.

* * * * *

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gaaggaggct attggccatg gac                                    23

<210> SEQ ID NO 2
<211> LENGTH: 52
<212> TYPE: DNA
<213> ORGANISM: Artificial Sequence
<220> FEATURE:
<223> OTHER INFORMATION: Primer

<400> SEQUENCE: 2
atatggatcc ttagtgatgg tgatggtgat gataaagagg agtgtcatct gc     52